US012612661B2

(12) United States Patent
Whitaker et al.

(10) Patent No.: US 12,612,661 B2
(45) Date of Patent: Apr. 28, 2026

(54) COMPOSITIONS AND METHODS FOR ASSESSING THE EFFICACY OF INHIBITORS OF NEUROTRANSMITTER TRANSPORTERS

(71) Applicant: DENOVO BIOPHARMA LLC, San Diego, CA (US)

(72) Inventors: John W Whitaker, San Diego, CA (US); Zafrin Dhali, San Diego, CA (US); Hong Sun, San Diego, CA (US); Haiping Lu, San Diego, CA (US); Xiaojun Li, San Diego, CA (US); Wilson Wu, San Diego, CA (US); Wen Luo, San Diego, CA (US)

(73) Assignee: Denovo Biopharma, LLC, San Diego, CA (US)

( * ) Notice: Subject to any disclaimer, the term of this patent is extended or adjusted under 35 U.S.C. 154(b) by 810 days.

(21) Appl. No.: 17/905,511

(22) PCT Filed: Feb. 23, 2021

(86) PCT No.: PCT/US2021/019265
§ 371 (c)(1),
(2) Date: Sep. 2, 2022

(87) PCT Pub. No.: WO2021/178166
PCT Pub. Date: Sep. 10, 2021

(65) Prior Publication Data
US 2023/0193388 A1    Jun. 22, 2023

Related U.S. Application Data

(60) Provisional application No. 62/986,603, filed on Mar. 6, 2020.

(51) Int. Cl.
| | |
|---|---|
| *C12Q 1/68* | (2018.01) |
| *C12P 19/34* | (2006.01) |
| *C12Q 1/6883* | (2018.01) |
| *C12Q 1/6858* | (2018.01) |

(52) U.S. Cl.
CPC ......... *C12Q 1/6883* (2013.01); *C12Q 1/6858* (2013.01); *C12Q 2600/106* (2013.01); *C12Q 2600/156* (2013.01)

(58) Field of Classification Search
CPC ................ C12Q 1/6883; C12Q 1/6858; C12Q 2600/106; C12Q 2600/156
See application file for complete search history.

(56) References Cited

U.S. PATENT DOCUMENTS

| | | |
|---|---|---|
| 2011/0189663 A1 | 8/2011 | Cotterchio et al. |
| 2013/0132114 A1 | 5/2013 | Lombard |
| 2016/0145682 A1 | 5/2016 | Woodward et al. |

| | | |
|---|---|---|
| 2017/0029892 A1 | 2/2017 | Lombard |
| 2017/0051350 A1 | 2/2017 | Zhu et al. |
| 2017/0253928 A1 | 9/2017 | Zhu et al. |

FOREIGN PATENT DOCUMENTS

| | | |
|---|---|---|
| WO | 2008065544 A2 | 6/2008 |

OTHER PUBLICATIONS

Submitted SNP(ss) Details: ss536764342 (RefSNP(rs#) rs12217173) from https://www.ncbi.nlm.nih.gov/, Jun. 22, 2012. (Year: 2012).*
"A Biomarker-Guided, Randomized, Double-Blind, Placebo-Controlled Efficacy and Safety Study of Liafensine in Patients with Treatment Resistant Depression" Protocol No. DB104-01, from Denovo Biopharma LLC. Aug. 29, 2022, from https://cdn.clinicaltrials.gov/large-docs/71/NCT05113771/Prot_000.pdf (Year: 2022).*
Jeffrey D. Wall, et al. "Haplotype blocks and linkage disequilibrium in the human genome" Nature Reviews Genetics vol. 4, pp. 587-597 (Aug. 1, 2003) (Year: 2003).*
Submitted SNP(ss) Details: ss1751974789, May 27, 2015, from https://www.ncbi.nlm.nih.gov/projects/SNP/snp_ss.cgi?subsnp_id=ss1751974789 (Year: 2015).*
Wei Guo, et al. "Exploratory genome-wide association analysis of response to ketamine and a polygenic analysis of response to scopolamine in depression" Translational Psychiatry vol. 8, Article No. 280 (Dec. 14, 2018) (Year: 2018).*
Ana Elisa Castro Sotos, et al. "The Transitivity Misconception of Pearson's Correlation Coefficient", Nov. 2009, Statistics Education Research Journal 8(2):33-55. (Year: 2009).*
Elizabeth Pennisi, "A closer look at SNPs suggests difficulties" Science; Sep. 18, 1998; 281, 5384 p. 1787-1789. (Year: 1998).*
Jack Lucentini "Gene Association Studies Typically Wrong" The Scientist, Dec. 20, 2004 (Year: 2004).*
Submitted SNP(ss) Details: ss20615278 , RefSNP(rs#) rs12217173 (Mar. 18, 2004), from the dbSNP Short Genetic Variations database at https://www.ncbi.nlm.nih.gov/projects/SNP (Year: 2004).*
Lane RM. Antidepressant drug development: Focus on triple monoamine reuptake inhibition. Journal of Psychopharmacology. 2014;29(5):526-544. (Year: 2014).*
PCT/US2021/019265 International Search Report, May 13, 2021.
PCT/US2021/019265 Written Opinion of the International Searching Authority, May 13, 2021.
Naiyer A. Rizvi et al., A Phase I Study of LGD1069 in Adults with Advanced Cancer, Clinical Cancer Research Jul. 5, 1999, 1658-64.
Jeremy R Graff et al., The Protein Kinase CB-Selective Inhibitor, Enzastaurin (LY317615.HCl), Suppresses Signaling through the AKT Pathway, Induces Apoptosis, and Supresses Growth of Human Colon Cancer and Glioblastoma Xenografts, Cancer Res 2005, 65 (16), 7462-69.

(Continued)

*Primary Examiner* — Stephen T Kapushoc
(74) *Attorney, Agent, or Firm* — Vance Intellectual Property, PC

(57) ABSTRACT

The present invention relates to the field of pharmacogenomics, which applies one or more genomic biomarkers and the related diagnostic methods, devices, reagents, systems, and kits, for predicting varied individual responses such as, for example, efficacy or adverse effect, to therapeutic agents, e.g., inhibitors of certain neurotransmitter transporters such as liafensine.

14 Claims, 17 Drawing Sheets

Specification includes a Sequence Listing.

(56)        References Cited

OTHER PUBLICATIONS

Anne-Sophie Moreau et al., Protein kinase C inhibitor enzastaurin induces in vitro and in vivo antitumor activity in Waldenstrom macroglobulinemia, Blood 2007, 109 (11), 4964-72.

Klaus Podar et al., Targeting PKC in multiple myeloma: in vitro and in vivo effects of the novel orally available small-molecule inhibitor enzastaurin (LY317615.HCI), Blood 2007, 109 (4), 1669-77.

Mujahid A. Rizvi et al., Enzastaurin (LY317615), a protein kinase CB inhibitor, inhibits the AKT pathway and induces apoptosis in multiple myeloma cell lines, Mol Cancer Ther 2006, 5 (7), 1783-89.

Aaron C Spalding et al., Inhibition of Protein Kinase CB by Enzastaurin Enhances Radiation Cytotoxicity in Pancreatic Cancer, Clin Cancer Res 2007, 13 (22), 6827-33.

H L Mcleod et al., Selection of Markers to Predict Tumour Response or Survival: Description of a Novel Approach, European Journal of Cancer, 1999, 35 (12), 1650-52.

Kip A West et al., Activation of the PI3K/Akt pathway and chemo-therapeutic resistance, Drug Resistance Updates 2002, 5, 234-78.

Christiane Querfeld et al., The Selective Protein Kinase CB Inhibi-tor Enzastaurin Induces Apoptosis in Cutaneous T-Cell Lymphoma Cell Lines through the AKT Pathway, J Investigative Dermatology 2006, 126, 1641-47.

Office Action in Taiwan Application No. 110107927, mailed Nov. 6, 2024.

English Translation of the Office Action in Taiwan Application No. 110107927, mailed Nov. 6, 2024.

Porcelli, S. et al., Pharmacogenetics of antidepressant response, J Psychiatry Neurosci. 2011, 36(2), 87-113.

EP 21764344.4 supplementary European search report mailed Mar. 11, 2024.

Subbaiah, M. A. M., Triple Reuptake Inhibitors as Potential Thera-peutics for Depression and Other Disorders: Design Paradigm and Developmental Challenges, J. Med. Chem. 2018, 61, 2133-2165.

* cited by examiner

Figure 1A:
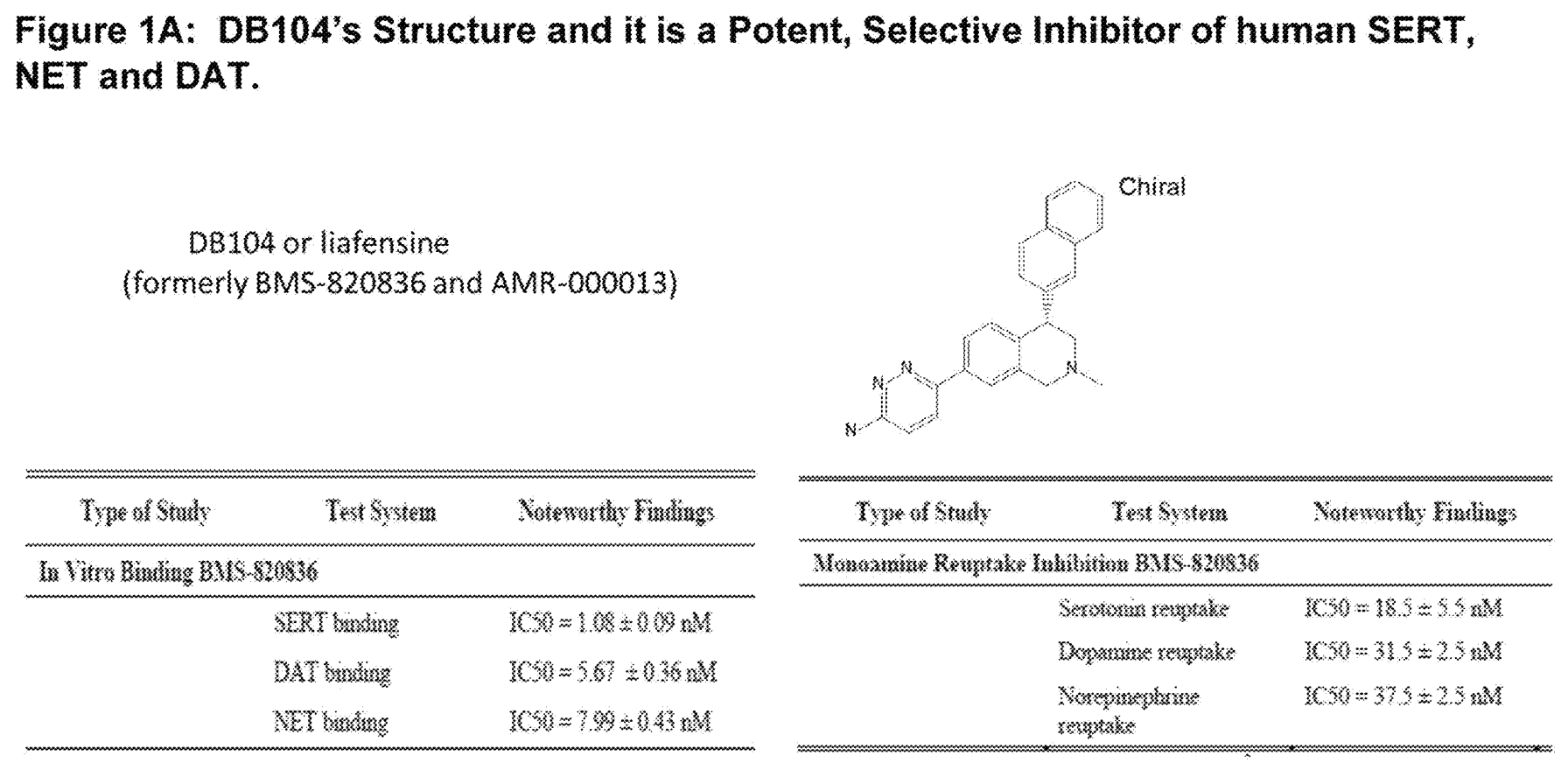

Figure 1A: DB104's Structure and it is a Potent, Selective Inhibitor of human SERT, NET and DAT.

DB104 or liafensine
(formerly BMS-820836 and AMR-000013)

Chiral

| Type of Study | Test System | Noteworthy Findings |
|---|---|---|
| In Vitro Binding BMS-820836 | | |
| | SERT binding | IC50 = 1.08 ± 0.09 nM |
| | DAT binding | IC50 = 5.67 ± 0.36 nM |
| | NET binding | IC50 = 7.99 ± 0.43 nM |

| Type of Study | Test System | Noteworthy Findings |
|---|---|---|
| Monoamine Reuptake Inhibition BMS-820836 | | |
| | Serotonin reuptake | IC50 = 18.5 ± 5.5 nM |
| | Dopamine reuptake | IC50 = 31.5 ± 2.5 nM |
| | Norepinephrine reuptake | IC50 = 37.5 ± 2.5 nM |

Figure 1B:  CN162-006 Design: Flexible-dose study

Figure 1C: CN162-007 Study Design Fixed-dose, dose-response study

DB104 Biomarker Discovery Set

Treatment duration (weeks)

Total MADRS change from baseline (mean ± SE)

DB104 AA 66
DB104 AG 75
DB104 GG 45
SOC 182

DB104 Biomarker All Data

DB104 AA 85
DB104 AG 94
DB104 GG 54
SOC AA 73
SOC AG 82
SOC GG 27

Total MADRS change from baseline (mean ± SE)

Treatment duration (weeks)

FIG.5

ANK3 Gene expression across different tissues
Gene expression for ANK3 (ENSG00000151150.21)

Figure 7
*Table 2A

MADRS Total Score Change from Baseline at Week 6 - Excluding 0.25 mg and 0.5 mg Dose Level Subjects with MADRS in Phase C

| | DB104 | SOC | Treatment Difference LS Mean (SE) or Rate Ratio | P-value |
|---|---|---|---|---|
| No. of Subjects at Baseline | 176 | 182 | | |
| Week 1 | | | | |
| LS Mean - Multivariable MMRM | -2.9 (0.79) | -2.9 (0.77) | -0.07 (0.57) | 0.8995 |
| MADRS Response Rate | 9 (5.2) | 4 (2.2) | 2.30 | 0.1457 |
| MADRS Remission Rate | 6 (3.4) | 4 (2.2) | 1.53 | 0.4977 |
| Week 2 | | | | |
| LS Mean - Multivariable MMRM | -5.1 (0.83) | -4.7 (0.81) | -0.36 (0.67) | 0.5895 |
| MADRS Response Rate | 20 (12.3) | 14 (8.4) | 1.46 | 0.2456 |
| MADRS Remission Rate | 15 (9.2) | 9 (5.4) | 1.71 | 0.1823 |
| Week 3 | | | | |
| LS Mean - Multivariable MMRM | -6.3 (0.85) | -5.6 (0.84) | -0.72 (0.73) | 0.3228 |
| MADRS Response Rate | 39 (23.1) | 22 (13.2) | 1.75 | 0.0185 |
| MADRS Remission Rate | 17 (10.1) | 12 (7.2) | 1.40 | 0.3483 |
| Week 4 | | | | |
| LS Mean - Multivariable MMRM | -7.0 (0.89) | -6.7 (0.88) | -0.31 (0.82) | 0.7092 |
| MADRS Response Rate | 40 (24.8) | 33 (20.0) | 1.24 | 0.2941 |
| MADRS Remission Rate | 28 (17.4) | 20 (12.1) | 1.43 | 0.1794 |

Figure 7 (continued)

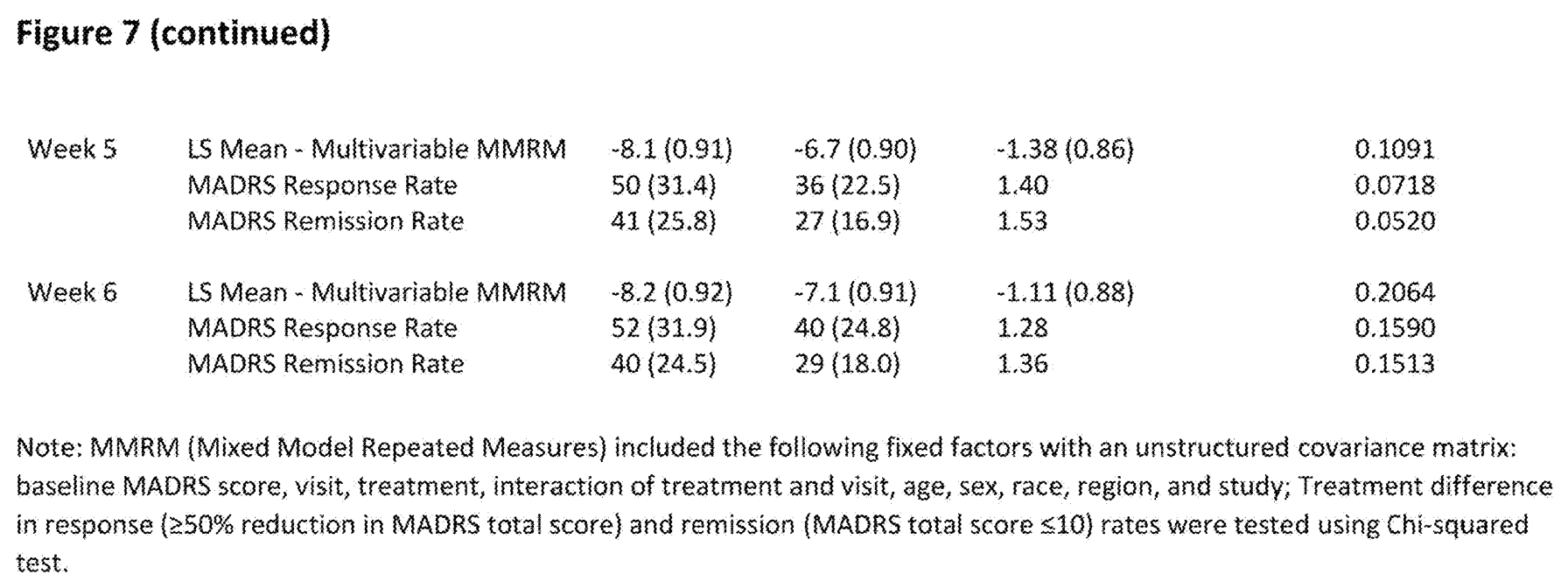

| Week 5 | LS Mean - Multivariable MMRM | -8.1 (0.91) | -6.7 (0.90) | -1.38 (0.86) | 0.1091 |
|---|---|---|---|---|---|
| | MADRS Response Rate | 50 (31.4) | 36 (22.5) | 1.40 | 0.0718 |
| | MADRS Remission Rate | 41 (25.8) | 27 (16.9) | 1.53 | 0.0520 |
| Week 6 | LS Mean - Multivariable MMRM | -8.2 (0.92) | -7.1 (0.91) | -1.11 (0.88) | 0.2064 |
| | MADRS Response Rate | 52 (31.9) | 40 (24.8) | 1.28 | 0.1590 |
| | MADRS Remission Rate | 40 (24.5) | 29 (18.0) | 1.36 | 0.1513 |

Note: MMRM (Mixed Model Repeated Measures) included the following fixed factors with an unstructured covariance matrix: baseline MADRS score, visit, treatment, interaction of treatment and visit, age, sex, race, region, and study; Treatment difference in response (≥50% reduction in MADRS total score) and remission (MADRS total score ≤10) rates were tested using Chi-squared test.

Figure 8
*Table 2B

MADRS Total Score Change from Baseline at Week 6 – Excluding 0.25 mg and 0.5 mg Dose Level Subjects with Genotype GG

| | DB104 | SOC | Treatment Difference LS Mean (SE) or Rate Ratio | P-value |
|---|---|---|---|---|
| No. of Subjects at Baseline | 47 | 27 | | |
| Week 1 | | | | |
| LS Mean – Multivariable MMRM | -4.0 (2.09) | -2.7 (1.99) | -1.24 (1.46) | 0.3998 |
| MADRS Response Rate | 4 (8.5) | 0 | | 0.1191 |
| MADRS Remission Rate | 3 (6.4) | 0 | | 0.1802 |
| Week 2 | | | | |
| LS Mean – Multivariable MMRM | -5.6 (2.09) | -3.9 (1.99) | -1.72 (1.47) | 0.2489 |
| MADRS Response Rate | 8 (17.8) | 1 (4.0) | 4.44 | 0.0989 |
| MADRS Remission Rate | 6 (13.3) | 0 | | 0.0562 |
| Week 3 | | | | |
| LS Mean – Multivariable MMRM | -9.3 (2.19) | -5.4 (2.16) | -3.94 (1.81) | 0.0333 |
| MADRS Response Rate | 19 (43.2) | 6 (25.0) | 1.73 | 0.1373 |
| MADRS Remission Rate | 10 (22.7) | 2 (8.3) | 2.73 | 0.1368 |
| Week 4 | | | | |
| LS Mean – Multivariable MMRM | -10.2 (2.23) | -6.9 (2.22) | -3.30 (1.92) | 0.0909 |
| MADRS Response Rate | 18 (42.9) | 4 (15.4) | 2.79 | 0.0186 |
| MADRS Remission Rate | 14 (33.3) | 4 (15.4) | 2.17 | 0.1030 |

Figure 8 (continued)

| | | | | |
|---|---|---|---|---|
| Week 5 | LS Mean - Multivariable MMRM | -11.8 (2.24) | -6.6 (2.24) | -5.24 (1.95) | 0.0090 |
| | MADRS Response Rate | 22 (51.2) | 6 (25.0) | 2.05 | 0.0374 |
| | MADRS Remission Rate | 22 (51.2) | 4 (16.7) | 3.07 | 0.0055 |
| Week 6 | LS Mean - Multivariable MMRM | -12.4 (2.27) | -7.7 (2.30) | -4.74 (2.06) | 0.0246 |
| | MADRS Response Rate | 26 (59.1) | 8 (32.0) | 1.85 | 0.0305 |
| | MADRS Remission Rate | 19 (43.2) | 5 (20.0) | 2.16 | 0.0520 |

Note: MMRM (Mixed Model Repeated Measures) included the following fixed factors with an unstructured covariance matrix: baseline MADRS score, visit, treatment, interaction of treatment and visit, age, sex, race, region, and study; Treatment difference in response ($\geq$50% reduction in MADRS total score) and remission (MADRS total score $\leq$10) rates were tested using Chi-squared test.

Figure 9

\* Table 3A. rs12217173 Genotype frequencies in different ethnic groups (HAP Maps)

| Population | ssID | Submitter | Allele: frequency (count) | | Genotype: frequency (count) | | |
|---|---|---|---|---|---|---|---|
| CSHL-HAPMAP: HapMap-HCB | ss39708910 | CSHL-HAPMAP | A: 0.611 (55) | G: 0.389 (35) | A\|A: 0.400 (18) | A\|G: 0.422 (19) | G\|G: 0.178 (8) |
| CSHL-HAPMAP: HapMap-CEU | ss39708910 | CSHL-HAPMAP | A: 0.567 (68) | G: 0.433 (52) | A\|A: 0.300 (18) | A\|G: 0.533 (32) | G\|G: 0.167 (10) |
| CSHL-HAPMAP: HapMap-JPT | ss39708910 | CSHL-HAPMAP | A: 0.557 (49) | G: 0.443 (39) | A\|A: 0.318 (14) | A\|G: 0.477 (21) | G\|G: 0.205 (9) |
| CSHL-HAPMAP: HapMap-YRI | ss39708910 | CSHL-HAPMAP | A: 0.817 (98) | G: 0.183 (22) | A\|A: 0.650 (39) | A\|G: 0.333 (20) | G\|G: 0.017 (1) |

Figure 10

*Table 3B. rs12217173 Genotype frequencies in different ethnic groups (1000 Genomes)

| Population | Allele: frequency (count) | | Genotype: frequency (count) | | |
|---|---|---|---|---|---|
| 1000GENOMES:phase_3:ALL | A: 0.641 (3210) | G: 0.359 (1798) | A\|A: 0.421 (1055) | A\|G: 0.439 (1100) | G\|G: 0.139 (349) |
| 1000GENOMES:phase_3:AFR | A: 0.806 (1066) | G: 0.194 (256) | A\|A: 0.648 (428) | A\|G: 0.318 (210) | G\|G: 0.035 (23) |
| 1000GENOMES:phase_3:ACB | A: 0.755 (145) | G: 0.245 (47) | A\|A: 0.604 (58) | A\|G: 0.302 (29) | G\|G: 0.094 (9) |
| 1000GENOMES:phase_3:ASW | A: 0.779 (95) | G: 0.221 (27) | A\|A: 0.574 (35) | A\|G: 0.410 (25) | G\|G: 0.016 (1) |
| 1000GENOMES:phase_3:ESN | A: 0.833 (165) | G: 0.167 (33) | A\|A: 0.697 (69) | A\|G: 0.273 (27) | G\|G: 0.030 (3) |
| 1000GENOMES:phase_3:LWK | A: 0.758 (150) | G: 0.242 (48) | A\|A: 0.545 (54) | A\|G: 0.424 (42) | G\|G: 0.030 (3) |
| 1000GENOMES:phase_3:MAG | A: 0.836 (189) | G: 0.164 (37) | A\|A: 0.690 (78) | A\|G: 0.292 (33) | G\|G: 0.018 (2) |
| 1000GENOMES:phase_3:MSL | A: 0.835 (142) | G: 0.165 (28) | A\|A: 0.706 (60) | A\|G: 0.259 (22) | G\|G: 0.035 (3) |
| 1000GENOMES:phase_3:YRI | A: 0.833 (180) | G: 0.167 (36) | A\|A: 0.685 (74) | A\|G: 0.296 (32) | G\|G: 0.019 (2) |
| 1000GENOMES:phase_3:AMR | A: 0.719 (499) | G: 0.281 (195) | A\|A: 0.527 (183) | A\|G: 0.383 (133) | G\|G: 0.089 (31) |
| 1000GENOMES:phase_3:CLM | A: 0.617 (116) | G: 0.383 (72) | A\|A: 0.415 (39) | A\|G: 0.404 (38) | G\|G: 0.181 (17) |
| 1000GENOMES:phase_3:MXL | A: 0.750 (96) | G: 0.250 (32) | A\|A: 0.547 (35) | A\|G: 0.406 (26) | G\|G: 0.047 (3) |
| 1000GENOMES:phase_3:PEL | A: 0.876 (149) | G: 0.124 (21) | A\|A: 0.765 (65) | A\|G: 0.224 (19) | G\|G: 0.012 (1) |
| 1000GENOMES:phase_3:PUR | A: 0.663 (138) | G: 0.337 (70) | A\|A: 0.423 (44) | A\|G: 0.481 (50) | G\|G: 0.096 (10) |
| 1000GENOMES:phase_3:EAS | A: 0.569 (574) | G: 0.431 (434) | A\|A: 0.317 (160) | A\|G: 0.504 (254) | G\|G: 0.179 (90) |

Figure 10 (continued)

| | A | G | A\|A | A\|G | G\|G |
|---|---|---|---|---|---|
| 1000GENOMES:phase_3:CDX | A: 0.575 (107) | G: 0.425 (79) | A\|A: 0.312 (29) | A\|G: 0.527 (49) | G\|G: 0.161 (15) |
| 1000GENOMES:phase_3:CHB | A: 0.534 (110) | G: 0.466 (96) | A\|A: 0.282 (29) | A\|G: 0.505 (52) | G\|G: 0.214 (22) |
| 1000GENOMES:phase_3:CHS | A: 0.533 (112) | G: 0.467 (98) | A\|A: 0.276 (29) | A\|G: 0.514 (54) | G\|G: 0.210 (22) |
| 1000GENOMES:phase_3:JPT | A: 0.582 (121) | G: 0.418 (87) | A\|A: 0.356 (37) | A\|G: 0.452 (47) | G\|G: 0.192 (20) |
| 1000GENOMES:phase_3:KHV | A: 0.626 (124) | G: 0.374 (74) | A\|A: 0.364 (36) | A\|G: 0.525 (52) | G\|G: 0.111 (11) |
| 1000GENOMES:phase_3:EUR | A: 0.556 (559) | G: 0.444 (447) | A\|A: 0.292 (147) | A\|G: 0.527 (265) | G\|G: 0.181 (91) |
| 1000GENOMES:phase_3:CEU | A: 0.556 (110) | G: 0.444 (88) | A\|A: 0.283 (28) | A\|G: 0.545 (54) | G\|G: 0.172 (17) |
| 1000GENOMES:phase_3:FIN | A: 0.606 (120) | G: 0.394 (78) | A\|A: 0.343 (34) | A\|G: 0.525 (52) | G\|G: 0.131 (13) |
| 1000GENOMES:phase_3:GBR | A: 0.522 (95) | G: 0.478 (87) | A\|A: 0.209 (19) | A\|G: 0.626 (57) | G\|G: 0.165 (15) |
| 1000GENOMES:phase_3:IBS | A: 0.579 (124) | G: 0.421 (90) | A\|A: 0.336 (36) | A\|G: 0.486 (52) | G\|G: 0.178 (19) |
| 1000GENOMES:phase_3:TSI | A: 0.514 (110) | G: 0.486 (104) | A\|A: 0.280 (30) | A\|G: 0.467 (50) | G\|G: 0.252 (27) |
| 1000GENOMES:phase_3:SAS | A: 0.524 (512) | G: 0.476 (466) | A\|A: 0.280 (137) | A\|G: 0.487 (238) | G\|G: 0.233 (114) |
| 1000GENOMES:phase_3:BEB | A: 0.576 (99) | G: 0.424 (73) | A\|A: 0.360 (31) | A\|G: 0.430 (37) | G\|G: 0.209 (18) |
| 1000GENOMES:phase_3:GIH | A: 0.553 (114) | G: 0.447 (92) | A\|A: 0.311 (32) | A\|G: 0.485 (50) | G\|G: 0.204 (21) |
| 1000GENOMES:phase_3:ITU | A: 0.495 (101) | G: 0.505 (103) | A\|A: 0.245 (25) | A\|G: 0.500 (51) | G\|G: 0.255 (26) |
| 1000GENOMES:phase_3:PJL | A: 0.505 (97) | G: 0.495 (95) | A\|A: 0.240 (23) | A\|G: 0.531 (51) | G\|G: 0.229 (22) |
| 1000GENOMES:phase_3:STU | A: 0.495 (101) | G: 0.505 (103) | A\|A: 0.255 (26) | A\|G: 0.480 (49) | G\|G: 0.265 (27) |

COMPOSITIONS AND METHODS FOR ASSESSING THE EFFICACY OF INHIBITORS OF NEUROTRANSMITTER TRANSPORTERS

RELATED APPLICATION

The present application claims priority to PCT Application No. PCT/US2021/019265, filed Feb. 23, 2021, which claims priority to U.S. provisional patent application No. 62/986,603, filed on Mar. 6, 2020, the disclosures of which is incorporated herein by reference in their entirety for all purposes.

SUBMISSION OF SEQUENCE LISTING ON ASCII TEXT FILE

The contents of the electronic sequence listing (DB-104-US ST25.xml; Size: 20 KB; and Date of Creation: 24 Oct. 2025) is herein incorporated by reference in its entirety.

TECHNICAL FIELD

The present invention relates to the field of pharmacogenomics, which applies one or more genomic biomarkers and the related diagnostic methods, devices, reagents, systems, and kits, for predicting varied individual responses such as, for example, efficacy or adverse effect, to therapeutic agents, e.g., inhibitors of certain neurotransmitter transporters such as liafensine.

BACKGROUND

Pharmacogenomics is the study of inheritable traits affecting subject response to drug treatment. Differential responses to drug treatment may be due to underlying genetic polymorphisms (genetic variations sometimes called mutations) that affect drug metabolism. Testing subjects for these genetic polymorphisms may help to prevent or minimize adverse drug reactions and facilitate appropriate drug dosing regimens.

In the clinical setting, pharmacogenomics may enable physicians to select the appropriate pharmaceutical agents, and the appropriate dosage of these agents, for each individual subject. That is, pharmacogenomics can identify those subjects with the right genetic makeup to respond to a given therapy. In addition, pharmacogenomics can identify those subjects with genetic variations in the genes that control the metabolism of pharmaceutical compounds, so that the proper treatment (or no treatment) decision can be made, and the proper dosage can be administered.

DB104 or liafensine (formerly BMS-820836 and AMR-000013) is a potent and selective inhibitor of the reuptake of some or all of the three monoamines; serotonin (5-HT), norepinephrine (NE) and dopamine (DA) by targeting the serotonin transporter (SERT), norepinephrine transporter (NET) and/or the dopamine transporter (DAT) respectively. DB104 has been evaluated as monotherapy for the treatment of major depressive disorder (MDD) in adults who have experienced inadequate response to separate trials of adequate dose and duration of two antidepressants from different classes in the current episode. DB104 was developed to incrementally advance antidepressant treatment by synergizing the individual, though complementary, mono-aminergic treatments for depression to maximize antidepressant efficacy and tolerability.

DB104 was taken through significant preclinical research, early development and subsequently multiple phase 2 clinical studies in treatment-resistant depression were conducted. DB104 was well tolerated, with no evidence of dose-dependent discontinuations due to adverse events. The program, however, was not continued beyond phase 2 studies due to unsatisfactory results from the phase 2 studies. (Bhagwagar Z. et al. 2015)

There is a need for new and alternative compositions and methods to determine drug sensitivity or monitor response in patients to allow the development of individualized treatment for diseases and disorders based on patient response at a molecular level. Pharmacogenomics may be used to discover and/or develop new and improved compositions and methods for treatment and prognosis of central nervous system (CNS) diseases or disorders, e.g., major depressive disorder (MDD). The present disclosure meets this and the related needs.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, the present disclosure describes one or more genomic biomarkers that correlate with different responses (e.g., efficacy, adverse effect, and other end points) among patients receiving a treatment regime using an inhibitor of a serotonin transporter (SERT), a norepinephrine transporter (NET) and/or a dopamine transporter (DAT), e.g., liafensine (formerly BMS-820836 and AMR-000013), for treating CNS diseases or disorders, such as a major depressive disorder (MDD). The biomarker or biomarkers can be used in companion diagnostic tests which can help to predict drug responses and apply drugs only to those who will be benefited, and/or exclude those who might have negative outcome and/or adverse effects due to the treatment.

In one aspect, the present disclosure provides for an isolated polynucleotide comprising, consisting of, or consisting essentially of a single nucleotide polymorphism (SNP) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof.

In another aspect, the present disclosure provides for a panel of isolated polynucleotides comprising, consisting of, or consisting essentially of two or more, three or more, four or more, or five or more of the above isolated polynucleotides.

In still another aspect, the present disclosure provides for a kit comprising the above isolated polynucleotide or panel, which kit optionally comprises an instruction for use.

In yet another aspect, the present disclosure provides for a microarray comprising a substrate and the above isolated polynucleotide or panel directly or indirectly immobilized on the substrate.

In yet another aspect, the present disclosure provides for a reagent for detecting one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof.

A kit comprising the above reagent is also provided, which kit optionally comprises an instruction for use. A kit comprising the above isolated polynucleotide or panel of any one of and the above reagent is further provided, which kit optionally comprises an instruction for use. A microarray comprising a substrate and the above reagent directly or indirectly immobilized on the substrate is further provided. A microarray comprising a substrate and the above isolated polynucleotide or panel and the above reagent directly or indirectly immobilized on the substrate is further provided.

In yet another aspect, the present disclosure provides for a companion diagnostic method, comprising: a) assaying a biological sample from a subject that is undergoing a treatment or is considered for a treatment for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof; and/or b) generating an output, e.g., a score, for example with a computer algorithm based on the assay results of said SNP or SNPs, in order to determine the likely responsiveness of said subject to said treatment.

In yet another aspect, the present disclosure provides for a method for classifying a subject for eligibility for a treatment, comprising: b) assaying a biological sample from a subject that is undergoing a treatment or is considered for a treatment for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof; and/or b) generating an output, e.g., a score, for example with a computer algorithm based on the assay results of said SNP or SNPs, in order to classify the subject as eligible or ineligible for the treatment or continued treatment.

In yet another aspect, the present disclosure provides for a method for screening a subject or a population of subjects for a treatment, comprising: a) assaying a biological sample(s) from a subject or a population of subjects that is undergoing a treatment or is considered for a treatment for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof; and/or b) generating an output, e.g., a score, for example with a computer algorithm based on the assay results of said SNP or SNPs, in order to determine whether the subject or the population is likely to benefit from the treatment or continued treatment, and/or to determine whether the subject or the population is likely to experience an adverse effect from the treatment or continued treatment.

In yet another aspect, the present disclosure provides for a method for monitoring a subject during a treatment, comprising: a) assaying a biological sample from a subject undergoing a treatment for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof; and/or b) generating an output, e.g., a score, for example with a computer algorithm based on the assay results of said SNP or SNPs, in order to determine whether the subject should receive continued treatment.

In yet another aspect, the present disclosure provides for a method for treating a central nervous system (CNS) disease or disorder in a subject, which method comprises administering an effective amount of: a) liafensine (BMS-820836 or AMR-000013), BMS-866949 (CSTI-500 or AMR-001181), or an analogue or derivative thereof; or b) an inhibitor of a serotonin transporter (SERT), a norepinephrine transporter (NET) and/or a dopamine transporter (DAT), to a subject that is in need for the treatment and has homozygous minor allele for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof.

In yet another aspect, the present disclosure provides for an use of an effective amount of: a) liafensine (BMS-820836 or AMR-000013), BMS-866949 (CSTI-500 or AMR-001181), or an analogue or derivative thereof; or b) an inhibitor of a serotonin transporter (SERT), a norepinephrine transporter (NET) and/or a dopamine transporter (DAT), for the manufacture of a medicament for treating a central nervous system (CNS) disease or disorder in a subject that is in need for the treatment and has homozygous minor allele for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof.

In some embodiments, the present disclosure provides a panel of biomarkers comprising single nucleotide polymorphisms (SNPs) selected from the group consisting of rs12217173, or other SNPs from Table 1 (Table 1A-1E), or complimentary sequences thereof, and/or in linkage disequilibrium therewith. In some embodiments, the biomarkers may comprise the nucleotide sequences set forth in SEQID NO:51, respectively or complimentary sequences thereof, and/or in linkage disequilibrium therewith (Table 1 or Table 1A-1E).

```
SEQ ID NO: 51: rs12217173) Immediate Flanking
Sequence:
TTCTTTTTGTCGCGGTTTAAGCCCATTTTCTATTGTGCTAACCTCAGCAA

AAAAGGACATCAGCTAGTTACCATTCTCCTCATGATTAAAACTAATTAAG

[A/G]

CATCCTTCCATCTCTGTCATTAGAAGCACATGCAAATGGGCATGTTTCCT

TAATTTCTGATTCTAAATTGAGAAAAGTATAAAGAAGCAATTCTGGGCTT
```

In some embodiments, provided herein is a reagent for the assessment of the biomarkers disclosed herein, which may comprise one or more molecules for assaying the SNP. In some embodiments, the molecules may be oligonucleotides or polypeptides. In some embodiments, the oligonucleotides may comprise the nucleotide sequences set forth in SEQID NO:51, or complimentary sequences thereof. In some embodiments, the SNP may be assayed by PCR, sequencing, capillary electrophoresis, mass spectrometry, single-strand conformation polymorphism (SSCP), electrochemical analysis, denaturing HPLC and gel electrophoresis, restriction fragment length polymorphism, hybridization analysis, single-base extension, and/or microarray.

In some embodiments, provided herein is a kit for the assessment of a panel of isolated biomarkers, which comprises the reagent disclosed herein, wherein the biomarkers may comprise one SNP rs12217173, or in linkage disequilibrium therewith. In some embodiments, the kit may further comprise instructions for using the biomarker to conduct a companion diagnostic test.

In some embodiments, provided herein is a companion diagnostic test for a treatment using a panel of isolated biomarkers comprising rs12217173, or in linkage disequilibrium therewith. In some embodiments, the companion diagnostic test may comprise: a) obtaining a biological sample from a subject that is undergoing a treatment or is considered for a treatment; b) isolating genomic DNA from said biological sample; c) assaying the biomarker or a panel of biomarkers; d) generating an output with a computer algorithm based on the assay results of said biomarker or panel of biomarkers; and/or e) determining the likely responsiveness of said subject to said treatment. In some embodiments, the SNPs may be assayed by PCR, sequencing, capillary electrophoresis, mass spectrometry, single-strand conformation polymorphism (SSCP), electrochemical analysis, denaturing HPLC and gel electrophoresis, restriction fragment length polymorphism, hybridization analysis, single-base extension, and/or microarray.

Further provided is a method of prognosticating responsiveness of a subject to a disease treatment using the companion diagnostic test disclosed herein. In some embodiments, the treatment may comprise a therapeutic regimen using DB104 or other inhibitors to SERT, and/or NET, and/or DAT. In some embodiments, the disease may be selected from the group consisting of major resistant depression, depression, bipolar, and other mental disorders. In some embodiments, the method may be used for selecting a patient who is most likely to benefit from the treatment or who is most likely to experience an adverse effect from the treatment.

In some embodiments, provided herein is a method of identifying a new biomarker using the panel of isolated biomarkers disclosed herein. In some embodiments, the new biomarker may be a DNA, a RNA, a polypeptide, a siRNA or another form of biomarker. Further provided herein is a method of identifying a drug target using an isolated biomarker a panel of isolated biomarkers disclosed herein. In some embodiments, the drug target may be identified based on a biological pathway related to a biomarker, wherein the biological pathway may be selected from the genes related to or regulated by the genomic regions affected by rs12217173.

BRIEF DESCRIPTION OF THE DRAWINGS

FIG. 1A shows DB104's structure and that it is a potent, selective inhibitor of human SERT, NET and DAT. In vitro Binding Result: Competition binding experiments were utilized to determine the in vitro binding potencies (IC50 values) of BMS-820836 for SERT, DAT, and NET. Membranes prepared from human embryonic kidney (HEK) cell lines overexpressing each transporter were employed in the assays. Radioligands were used at their respective affinity constant (Kd) concentrations for each transporter to enable direct comparisons of the IC50 values between assays. BMS-820836 completely saturated SERT, DAT, and NET binding sites with IC50 values listed in the table. Monoamine Reupdate inhibition: Cell-based assays were used to determine the ability of BMS-820836 to inhibit reuptake of 3H-labeled dopamine ([$^3$H]DA), norepinephrine ([$^3$H]NE), and serotonin ([$^3$H]5-HT). BMS-820836 potently and completely inhibited uptake of [$^3$H]DA into HEK293/hDAT cells with an IC50 listed in the table.

FIG. 1B illustrates CN162-006 Trial Design: Flexible-dose study.

FIG. 1C illustrates CN162-007 Study Design: Fixed-dose, dose-response study.

FIG. 7 (Table 2A) shows MADRS Total Score Change from Baseline at Week 6-Excluding 0.25 mg and 0.5 mg Dose Level (Subjects with MADRS in Phase C). Note: MMRM(Mixed Model Repeated Measures)included the following fixed factors with an unstructured covariance matrix:

Figure 1:
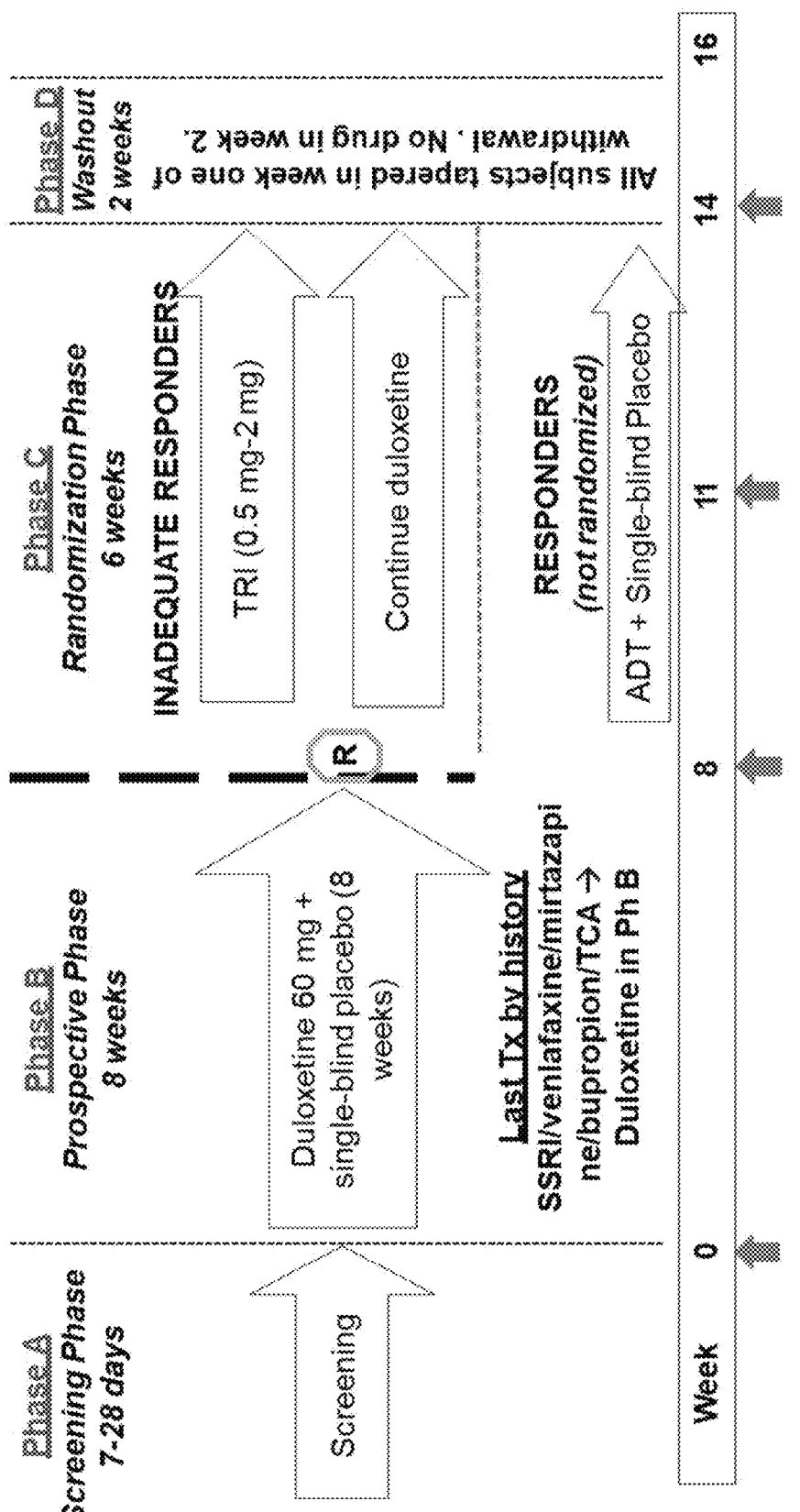
FIG. 1 depicts exemplary DB104 structure, preclinical result, and clinical trial design.

baseline MADRS score, visit, treatment, interaction of treatment and visit, age, sex, race, region, and study; Treatment difference in response (≥50% reduction in MADRS total score) and remission (MADRS total score ≤10) rates were tested using Chi-squared test.

FIG. 8 (Table 2B) shows MADRS Total Score Change from Baseline at Week 6-Excluding 0.25 mg and 0.5 mg Dose Level (Subjects with Genotype GG). Note: MMRM (Mixed Model Repeated Measures)included the following fixed factors with an unstructured covariance matrix: baseline MADRS score, visit, treatment, interaction of treatment and visit, age, sex, race, region, and study; Treatment difference in response (≥50% reduction in MADRS total score) and remission (MADRS total score ≤10) rates were tested using Chi-squared test.

FIG. 9 (Table 3A) shows Genotype frequencies in different ethnic groups (HAP Maps).

FIG. 10 (Table 3B) shows rs12217173 Genotype frequencies in different ethnic groups (1000 Genomes).

DETAILED DESCRIPTION OF THE INVENTION

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications referred to in this application are incorporated by reference in their entireties for all purposes to the same extent as if each individual publication were individually incorporated by reference.

All headings are for the convenience of the reader and should not be used to limit the meaning of the text that follows the heading, unless so specified.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

A. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

B. Definitions

Unless defined otherwise, all technical and scientific terms used herein have the same meaning as is commonly understood by one of ordinary skill in the art to which this invention belongs. All patients, applications, published applications and other publications referred to herein are incorporated by reference in their entireties. If a definition set forth in this section is contrary to or otherwise inconsistent with a definition set forth in the patients, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

The term "biomarker" or "marker" as used herein refers generally to a molecule, including a gene, protein, carbohydrate structure, or glycolipid, the expression of which in or on a mammalian tissue or cell or secreted can be detected by known methods (or methods disclosed herein) and is predictive or can be used to predict (or aid prediction) for a mammalian cell's or tissue's sensitivity to, and in some embodiments, to predict (or aid prediction) an individual's responsiveness to treatment regimens.

As used herein, a "pharmacogenomic biomarker" is an objective biomarker which correlates with a specific clinical drug response or susceptibility in a subject (see, e.g., McLeod et al., *Eur. J. Cancer* (1999) 35:1650-1652). It may be a biochemical biomarker, or a clinical sign or symptom. The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of DNA, RNA, or protein for specific tumor markers in a subject, a drug or course of treatment may be selected that is optimized for the treatment of a CNS disease or disorder likely to be present in the subject. Similarly, the presence or absence of a specific sequence mutation or polymorphism may correlate with drug response. The use of pharmacogenomic biomarkers therefore permits the application of the most appropriate treatment for each subject without having to administer the therapy. Methods for discovering pharmacogenomic biomarkers are known, for example, as disclosed in U.S. 2014/0031242 A1 or U.S. 2015/0368720 A1, which is incorporated herein by reference.

As used herein, the term "polymorphic locus" refers to a region in a nucleic acid at which two or more alternative nucleotide sequences are observed in a significant number of nucleic acid samples from a population of individuals. A polymorphic locus may be a nucleotide sequence of two or more nucleotides, an inserted nucleotide or nucleotide sequence, a deleted nucleotide or nucleotide sequence, or a microsatellite, for example. A polymorphic locus that is two or more nucleotides in length may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. A polymorphic locus is often one nucleotide in length, which is referred to herein as a "single nucleotide polymorphism" or a "SNP." In some embodiments, the high-density genotyping may be conducted by using SNPs. In some embodiments, about 1,000-5,000,000 or more SNPs, may be used. In some embodiments, the high-density genotyping may be array-based. In some embodiments, the high-density genotyping may be conducted by using sequencing, such as high-throughput sequencing.

Where there are two, three, or four alternative nucleotide sequences at a polymorphic locus, each nucleotide sequence is referred to as a "polymorphic variant" or "nucleic acid variant." Where two polymorphic variants exist, for example, the polymorphic variant represented in a minority of samples from a population is sometimes referred to as a "minor allele" and the polymorphic variant that is more prevalently represented is sometimes referred to as a "major allele." Many organisms possess a copy of each chromosome (e.g., humans), and those individuals who possess two major alleles or two minor alleles are often referred to as being "homozygous" with respect to the polymorphism, and those individuals who possess one major allele and one minor allele are normally referred to as being "heterozygous" with respect to the polymorphism. Individuals who are homozygous with respect to one allele are sometimes predisposed to a different phenotype as compared to individuals who are heterozygous or homozygous with respect to another allele.

Single-nucleotide polymorphisms may fall within coding sequences of genes, non-coding regions of genes, or in the intergenic regions (regions between genes). SNPs within a coding sequence do not necessarily change the amino acid sequence of the protein that is produced, due to degeneracy of the genetic code.

SNPs in the coding region are of two types, synonymous and nonsynonymous SNPs. Synonymous SNPs do not affect the protein sequence while nonsynonymous SNPs change the amino acid sequence of protein. The nonsynonymous SNPs are of two types: missense and nonsense. SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene.

In genetic analysis that identifies one or more pharmacogenomic biomarkers, samples from individuals having different values in a relevant phenotype often are allelotyped and/or genotyped. The term "allelotype" as used herein refers to a process for determining the allele frequency for a polymorphic variant in pooled DNA samples from cases and controls, and/or in separate DNA samples from each individual subject. By genotyping DNA from each group, an allele frequency for each locus in each group is calculated. These allele frequencies are then compared to one another. In some embodiments, DNA samples are genotyped using whole genome SNP arrays, such as those manufactured by Affymetrix (Santa Clara, Calif) and/or Illumina (San Diego, Calif), such as the Affymetrix 500K array. In addition to Affymetrix arrays, Illumina chips and Sequenom MassArray can also be used. Any suitable genotype calling algorithm(s) may be used. in some embodiments, the genotype calls are generated using the Robust Linear Model with the Mahalanobis Distance Classifier (RLMM) algorithm, the RI MM with a Bayesian step (BRI MM) algorithm, the Axiom™ GT1 algorithm, the BRLMM using perfect-match probes (131U,MM-P) algorithm, or the Birdseed algorithm (Rabbee et al., *Bioinformatics* (2006) 22:7-12; Korn et al., *Nat Genet* (2008) 40:1253-60).

A genotype or polymorphic variant may be expressed in terms of a "haplotype," which as used herein refers to a set of DNA variations, or polymorphisms, that tend to be inherited together. A haplotype can refer to a combination of alleles or to a set of SNPs found on the same chromosome. For example, two SNPs may exist within a gene where each SNP position includes a cytosine variation and an adenine variation. Certain individuals in a population may carry one allele (heterozygous) or two alleles (homozygous) having the gene with a cytosine at each SNP position. As the two cytosines corresponding to each SNP in the gene travel together on one or both alleles in these individuals, the individuals can be characterized as having a cytosine/cytosine haplotype with respect to the two SNPs in the gene.

Sometimes, a polymorphic variant is reported in a database without determining whether the variant is represented in a significant fraction of a population. Because a subset of these reported polymorphic variants are not represented in a statistically significant portion of the population, some of them are sequencing errors and/or not biologically relevant. Thus, it is often not known whether a reported polymorphic variant is statistically significant or biologically relevant until the presence of the variant is detected in a population of individuals and the frequency of the variant is determined. A polymorphic variant is statistically significant (and optionally often biologically relevant) if it is represented in 1% or more of a population, sometimes 5% or more, 10% or more, 15% or more, or 20% or more of a population, and often 25% or more, 30% or more, 35% or more, 40% or more, 45% or more, or 50% or more of a population. For certain genetic diseases and/or rare diseases, however, a variant may represent a very small percentage of a population and yet is still biologically relevant.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "clinical sample" or "disease sample" and variations thereof refer to any sample obtained from a subject of interest that would be expected or is known to contain the cellular and/or molecular entity that is to be characterized.

The term "tissue or cell sample" refers to a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds that are not naturally intermixed with the tissue in nature such as preservatives, anticoagulants, buffers, fixatives, nutrients, antibiotics, or the like.

The biological sample herein can be a plasma, serum, whole blood, or dried blood spot sample. "Plasma," or "blood plasma," as used herein, refers to the intravascular fluid part of extracellular fluid (all body fluid outside of cells). It is mostly water and contains dissolved proteins, glucose, clotting factors, mineral ions, hormones and carbon dioxide (plasma being the main medium for excretory product transportation). Blood plasma is prepared by spinning a tube of fresh blood containing an anti-coagulant in a centrifuge until the blood cells fall to the bottom of the tube. The blood plasma is then poured or drawn off "Blood serum" is blood plasma without fibrinogen or the other clotting factors (i.e., whole blood minus both the cells and the clotting factors).

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, $\alpha$-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "array" or "microarray", as used herein refers to an ordered arrangement of hybridizable array elements, such as polynucleotide probes (e.g., oligonucleotides), beads, or binding reagents (e.g., antibodies), on a substrate. The substrate can be a solid substrate, such as a glass or silica slide, a fiber optic binder, or a semi-solid substrate, such as nitrocellulose membrane. The nucleotide sequences can be DNA, RNA, or any permutations thereof.

As used herein, the term "phenotype" refers to a trait which can be compared between individuals, such as presence or absence of a condition, a visually observable difference in appearance between individuals, metabolic variations, physiological variations, variations in the function of biological molecules, and the like. A phenotype can be qualitative or quantitative. An example of a phenotype is responsiveness to a treatment, such as a drug.

"Responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) relief, to some extent, of one or more symptoms associated with the disorder; (7) increase in the length of disease-free presentation following treatment; (8) decreased mortality at a given point of time following treatment; and/or (9) lack of adverse effects following treatment. Responsiveness can also be assessed using any endpoint indicating side effect and/or toxicity to the patient.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. For example, increase in length of remission, and/or relief to some extent, one or more of the symptoms associated with a CNS disease or disorder; reduced morbidity and mortality, and improvement in quality of life issues. Reduction of the signs or symptoms of a CNS disease or disorder may also be felt by the patient. Treatment can achieve a complete response, defined as disappearance of all signs of a CNS disease or disorder, or a partial response, preferably reduction by more than 50 percent, more preferably by 75% of signs of a CNS disease or disorder. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "prediction" or "prognosis" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc.

As used herein, the term "specifically binds" refers to the binding specificity of a specific binding pair. Recognition by an antibody of a particular target in the presence of other potential targets is one characteristic of such binding. Specific binding involves two different molecules wherein one of the molecules specifically binds with the second molecule through chemical or physical means. The two molecules are related in the sense that their binding with each other is such that they are capable of distinguishing their binding partner from other assay constituents having similar characteristics. The members of the binding component pair are referred to as ligand and receptor (anti-ligand), specific binding pair (SBP) member and SBP partner, and the like. A molecule may also be an SBP member for an aggregation of molecules; for example an antibody raised against an immune complex of a second antibody and its corresponding antigen may be considered to be an SBP member for the immune complex.

As used herein, the term "homologue" is used to refer to a nucleic acid which differs from a naturally occurring nucleic acid (i.e., the "prototype" or "wild-type" nucleic acid) by minor modifications to the naturally occurring nucleic acid, but which maintains the basic nucleotide structure of the naturally occurring form. Such changes include, but are not limited to: changes in one or a few nucleotides, including deletions (e.g., a truncated version of the nucleic acid) insertions and/or substitutions. A homologue can have enhanced, decreased, or substantially similar properties as compared to the naturally occurring nucleic acid. A homologue can be complementary or matched to the naturally occurring nucleic acid. Homologues can be produced using techniques known in the art for the production of nucleic acids including, but not limited to, recombinant DNA techniques, chemical synthesis, etc.

As used herein, "complementary" or "matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C.

Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art.

As used herein, the term "output" refers to a value or score generated from a computer algorithm. The output may be generated based on assay results using the biomarkers disclosed herein as inputs to the computer algorithm. An "output" can be either quantitative or qualitative, and can be used for determining the likely responsiveness of a subject to a treatment in a companion diagnostic test.

A companion diagnostic test or method generally provides information that is essential for the safe and effective use of a corresponding drug or biological product. The test helps a health care professional determine whether a particular therapeutic product's benefits to patients will outweigh any potential serious side effects or risks. In certain aspects, a companion diagnostic test disclosed herein can identify patients who are most likely to benefit from a particular therapeutic agent, such as liafensine, BMS-866949, or an analogue or derivative thereof; identify patients likely to be at increased risk for serious side effects as a result of treatment with a particular therapeutic agent; and/or monitor response to treatment with a particular therapeutic agent for the purpose of adjusting treatment to achieve improved safety or effectiveness. Companion diagnostics may be co-developed with one or more drugs (or a combination therapy such as a cocktail) to aid in selecting or excluding patient groups for treatment with that particular drug on the basis of their biological characteristics that determine responders and non-responders to the therapy. In some aspects, companion diagnostics are developed based on companion biomarker(s), biomarkers that prospectively help predict likely response or severe toxicity. In some embodiments, the present disclosure provides a companion biomarker comprising one or more, for example, 1, 2, 3, 4, 5, 6, 7, 8, 9, 10, or more of the SNPs disclosed herein.

The term "pharmaceutically acceptable salt" means a salt which is acceptable for administration to a patient, such as a mammal, particularly a human, i.e., salts with counterions having acceptable mammalian safety for a given dosage regime. Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

C. Isolated Polynucleotides, Biomarkers, Related Compositions and Uses Thereof In one aspect, the present disclosure provides for an isolated polynucleotide comprising, consisting of, or consisting essentially of a single nucleotide polymorphism (SNP) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof.

In some embodiments, the SNP is rs12217173, one or more SNP listed in any of Tables 1A-1E, or a complementary SNP thereof In other embodiments, the SNP is rs12217173, rs12219340, rs4612751, rs12572120, or a complementary SNP thereof. In still other embodiments, the SNP is rs12217173, or a complementary SNP thereof.

In another aspect, the present disclosure provides for a panel of isolated polynucleotides comprising, consisting of, or consisting essentially of two or more, three or more, four or more, or five or more of the above isolated polynucleotides. In some embodiments in the panel comprises two, three or all of rs12217173, rs12219340, rs4612751, rs12572120, or a complementary SNP thereof.

The isolated polynucleotide or the isolated polynucleotides in the panel can comprise, consist of, or consist essentially of any of the suitable sequence(s). For example, the isolated polynucleotide or the isolated polynucleotides in the panel can comprise, consist of, or consist essentially of any of the sequences set forth in SEQ ID NOs: 1-51, a complementary sequence thereof, or a sequence in linkage disequilibrium therewith. In another example, the isolated polynucleotide or the isolated polynucleotides in the panel can comprise, consist of, or consist essentially of a sequence set forth in SEQ ID NOs: 51, 1, 2, or 5, a complementary sequence thereof, or a sequence in linkage disequilibrium therewith. In still another example, the isolated polynucleotide or the isolated polynucleotides in the panel can comprise, consist of, or consist essentially of a sequence set forth in SEQ ID NO:51, a complementary sequence thereof, or a sequence in linkage disequilibrium therewith.

In still another aspect, the present disclosure provides for a kit comprising the above isolated polynucleotide or panel, which kit optionally comprises an instruction for use.

In yet another aspect, the present disclosure provides for a microarray comprising a substrate and the above isolated polynucleotide or panel directly or indirectly immobilized on the substrate.

In yet another aspect, the present disclosure provides for a reagent for detecting one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof.

The present reagent can be used to detect any suitable single nucleotide polymorphism(s) or SNPs. In some embodiments, the present reagent can be used to detect one or more of rs12217173, a SNP listed in any of Tables 1A-1E, or a complementary SNP thereof. In some embodiments, the present reagent can be used to detect rs12217173, rs12219340, rs4612751, rs12572120, or a complementary SNP thereof. In some embodiments, the present reagent can be used to detect rs12217173, or a complementary SNP thereof.

The SNP or SNPs can comprise any suitable sequence(s). In some embodiments, the SNP or SNPs comprise a sequence set forth in of any of the sequences set forth in SEQ ID NOs: 1-51, a complementary sequence thereof, or a sequence in linkage disequilibrium therewith. In some embodiments, the SNP or SNPs comprise a sequence set forth in SEQ ID NOs: 51, 1, 2, or 5, a complementary sequence thereof, or a sequence in linkage disequilibrium therewith. In some embodiments, the SNP or SNPs comprise a sequence set forth in SEQ ID NO:51, a complementary sequence thereof, or a sequence in linkage disequilibrium therewith.

The present reagent can comprise one or more molecules for assaying the SNP or SNPs. The present reagent can comprise any suitable type(s) of molecule(s). In some embodiments, the one or more molecules in the present reagent can comprise an oligonucleotide and/or a polypeptide. The oligonucleotide(s) in the present reagent can comprise any suitable sequence(s). In some embodiments, the oligonucleotide(s) in the present reagent comprises a sequence set forth in any of the sequences set forth in SEQ ID NOs: 1-51, or a complementary sequence thereof In some embodiments, the oligonucleotide(s) in the present reagent comprises one or more primers for genotyping the SNP or SNPs.

In yet another aspect, the present disclosure provides for a kit comprising the above reagent, which kit optionally comprises an instruction for use.

In yet another aspect, the present disclosure provides for a kit comprising the above isolated polynucleotide or panel and the above reagent, which kit optionally comprises an instruction for use.

The present kit can comprise any suitable isolated polynucleotide or panel of polynucleotides. In some embodiments, isolated polynucleotide or panel of polynucleotides in the present kit comprises a SNP selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof, and the reagent is capable of detecting the SNP(s). In some embodiments, isolated polynucleotide or panel of polynucleotides in the present kit comprises rs12217173, a SNP listed in any of Tables 1A-1E, and/or a complementary SNP thereof, and the reagent is capable of detecting the SNP(s). In some embodiments, isolated polynucleotide or panel of polynucleotides in the present kit comprises rs12217173, rs12219340, rs4612751, rs12572120, and/or a complementary SNP thereof, and the reagent is capable of detecting the SNP(s). In some embodiments, isolated polynucleotide or panel of polynucleotides in the present kit comprises rs12217173, or a complementary SNP thereof, and the reagent is capable of detecting the SNP.

In the present kit, the reagent, the isolated polynucleotide or panel of polynucleotides can be used for any suitable purpose or function. For example, in the present kit, the reagent is capable of detecting the SNP(s), and the isolated polynucleotide or panel serves as a control for a detection assay.

In yet another aspect, the present disclosure provides for a microarray comprising a substrate and the above reagent directly or indirectly immobilized on the substrate.

In yet another aspect, the present disclosure provides for a microarray comprising a substrate and the above isolated polynucleotide, or panel of the isolated polynucleotides, and the reagent directly or indirectly immobilized on the substrate.

In the present microarray, the reagent, the isolated polynucleotide or panel of polynucleotides can be used for any suitable purpose or function. For example, the reagent is capable of detecting the SNP(s) and the isolated polynucleotide or panel serves as a control for a detection assay.

The present kit, reagent, or microarray can be used for any suitable purpose or function. For example, the present kit, reagent, or microarray can be used for the assessment of an isolated biomarker or a panel of isolated biomarkers, wherein the biomarker or biomarkers comprise a single nucleotide polymorphism (SNP) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof.

The isolated biomarker or panel can be assayed using any suitable techniques or procedures. For example, the isolated biomarker or panel can be assayed by sequencing, polymerase chain reaction (PCR), capillary electrophoresis, mass spectrometry, single-strand conformation polymorphism (SSCP), electrochemical analysis, denaturing HPLC and gel electrophoresis, restriction fragment length polymorphism, hybridization analysis, single-base extension (SBE), allele specific primer extension (ASPE), restriction enzyme digestion, strand displacement amplification (SDA), transcription mediated amplification (TMA), ligase chain reaction (LCR), nucleic acid sequence based amplification (NASBA), primer extension, rolling circle amplification (RCA), self sustained sequence replication (3 SR), loop-mediated isothermal amplification (LAMP), hybridization, nucleic acid sequencing, and/or microarray. Any suitable nucleic acid sequencing techniques or procedures can be used. For example, the nucleic acid sequencing can be Maxam-Gilbert sequencing, a chain-termination method, shotgun sequencing, bridge PCR, single-molecule real-time sequencing, ion semiconductor (ion torrent sequencing), sequencing by synthesis, sequencing by ligation (SOLiD sequencing), chain termination (Sanger sequencing), massively parallel signature sequencing (1MPSS), polony sequencing, 454 pyrosequencing, Illumina (Solexa) sequencing, DNA nanoball sequencing, heliscope single molecule sequencing, single molecule real time (SMRT) sequencing, nanopore DNA sequencing, tunnelling currents DNA sequencing, sequencing by hybridization, sequencing with mass spectrometry, microfluidic Sanger sequencing, a microscopy-based technique, RNAP sequencing, and/or in vitro virus high-throughput sequencing.

The present kit, reagent, or microarray can further comprise an instruction for using the isolated biomarker or panel to conduct a companion diagnostic test for a treatment, e.g., a treatment for a CNS disease or disorder such as depression.

The companion diagnostic test for the treatment can be conducted using any suitable biomarker or panel of biomarkers. In some embodiments, the companion diagnostic test for the treatment is conducted using rs12217173, a SNP listed in any of Tables 1A-1E, or a complementary SNP thereof. In some embodiments, the companion diagnostic test for the treatment is conducted using rs12217173, rs12219340, rs4612751, rs12572120, or a complementary SNP thereof. In some embodiments, the companion diagnostic test for the treatment is conducted using rs12217173, or a complementary SNP thereof.

The companion diagnostic test can be conducted for assessing any suitable treatment. For example, the treatment can be a treatment for major depressive disorder (MDD or depression) or a disease or disorder associated with abnormal level(s) of serotonin (5-HT), norepinephrine (NE) and/or dopamine (DA). In some embodiments, the disease or disorder is a central nervous system (CNS) disease or disorder.

The companion diagnostic test can be conducted for assessing a treatment for any suitable the CNS disease or disorder. For example, the CNS disease or disorder can be a major depressive disorder (MDD), e.g., a subtype of MDD, or a major depression with psychotic feature(s) and/or depression with peri- or postpartum onset, a post-traumatic stress disorder (PTSD), a bipolar disorder, an obsessive-compulsive disorder (OCD), an eating disorder, attention-deficit hyperactivity disorder (ADHD), a sleep disorder, e.g., narcolepsy, a substance use disorder, Tourette syndrome (TS), schizophrenia, epilepsy, migraine, and an autism spectrum disorder. The neurodegenerative disorder can be Alzheimer's disease (AD), Huntington's disease, or Parkinson's disease (PD). In some embodiments, the treatment is a treatment for major depressive disorder (MDD or depression).

The companion diagnostic test can be conducted for assessing a treatment using any suitable medication. For example, the treatment can comprise administering to a subject in need thereof a pharmaceutically effective amount of a medication for treating major depressive disorder (MDD or depression) or a medication for modulating level(s) of serotonin (5-HT), norepinephrine (NE) and/or dopamine (DA) in a subject.

The treatment can comprise administering to a subject in need thereof any suitable medication for treating major depressive disorder (MDD or depression) or a medication for modulating level(s) of serotonin (5-HT), norepinephrine (NE) and/or dopamine (DA). For example, the medication can comprise liafensine (BMS-820836 or AMR-000013), BMS-866949 (CSTI-500 or AMR-001181), or an analogue or derivative thereof. In another example, the medication can comprise an inhibitor of a serotonin transporter (SERT), a norepinephrine transporter (NET) and/or a dopamine transporter (DAT).

Any suitable inhibitor of a serotonin transporter can be used. For example, the inhibitor of a serotonin transporter can have: a) a binding affinity $IC_{50}$ to the serotonin transporter ranging from about 0.1 nm to about 1 μm, e.g., from about 0.1 nm to about 60 nm; and/or b) a functional potency $IC_{50}$ to the serotonin transporter ranging from about 0.1 nm to about 1 μm, e.g., from about 2 nm to about 200 nm. In some embodiments, the inhibitor of a serotonin transporter has a binding affinity $IC_{50}$ to the serotonin transporter at about 0.1 nm, 1 nm, 10 nm, 100 nm, or 1 μm, or any subrange thereof. In some embodiments, the inhibitor of a serotonin transporter has a binding affinity $IC_{50}$ to the serotonin transporter at about 0.1 nm, 1 nm, 10 nm, 20 nm, 30 nm, 40 nm, 50 nm, 60 nm, or any subrange thereof. In some embodiments, the inhibitor of a serotonin transporter has a functional potency $IC_{50}$ to the serotonin transporter at about 0.1 nm, 1 nm, 10 nm, 100 nm, or 1 μm, or any subrange thereof. In some embodiments, the inhibitor of a serotonin transporter has a functional potency $IC_{50}$ to the serotonin transporter at about 2 nm, 10 nm, 20 nm, 30 nm, 40 nm, 50 nm, 60 nm, 70 nm, 80 nm, 90 nm, 100 nm, 150 nm, 200 nm, or any subrange thereof.

Any suitable inhibitor of a norepinephrine transporter can be used. For example, the inhibitor of a norepinephrine transporter can have: a) an binding affinity $IC_{50}$ to the norepinephrine transporter ranging from about 1 nm to about 1 μm, e.g., from about 0.8 nm to about 80 nm; and/or b) a functional potency $IC_{50}$ to the norepinephrine transporter ranging from about 0.1 nm to about 1 μm, e.g., from about 4 nm to about 400 nm. In some embodiments, the inhibitor of a norepinephrine transporter has a binding affinity $IC_{50}$ to the norepinephrine transporter at about 0.1 nm, 1 nm, 10 nm, 100 nm, or 1 μm, or any subrange thereof. In some embodiments, the inhibitor of a norepinephrine transporter has a binding affinity $IC_{50}$ to the norepinephrine transporter at about 0.8 nm, 1 nm, 10 nm, 20 nm, 30 nm, 40 nm, 50 nm, 60 nm, 70 nm, 80 nm, or any subrange thereof. In some embodiments, the inhibitor of a norepinephrine transporter has a functional potency $IC_{50}$ to the norepinephrine transporter at about 0.1 nm, 1 nm, 10 nm, 100 nm, or 1 μm, or any subrange thereof. In some embodiments, the inhibitor of a norepinephrine transporter has a functional potency $IC_{50}$ to the norepinephrine transporter at about 4 nm, 10 nm, 20 nm, 30 nm, 40 nm, 50 nm, 60 nm, 70 nm, 80 nm, 90 nm, 100 nm, 200 nm, 300 nm, 400 nm, or any subrange thereof.

Any suitable inhibitor of a dopamine transporter can be used. For example, the inhibitor of a dopamine transporter can have: a) an binding affinity $IC_{50}$ to the dopamine transporter ranging from about 1 nm to about 1 μm, e.g., from about 0.6 nm to about 60 nm; and/or b) a functional potency $IC_{50}$ to the dopamine transporter ranging from about 0.1 nm to about 1 μm, e.g., from about 3 nm to about 300 nm. In some embodiments, the inhibitor of a dopamine transporter has an binding affinity $IC_{50}$ to the dopamine transporter at about 0.1 nm, 1 nm, 10 nm, 100 nm, or 1 μm, or any subrange thereof. In some embodiments, the inhibitor of a dopamine transporter has an binding affinity $IC_{50}$ to the dopamine transporter at about 0.6 nm, 1 nm, 10 nm, 20 nm, 30 nm, 40 nm, 50 nm, 60 nm, or any subrange thereof. In some embodiments, the inhibitor of a dopamine transporter has a functional potency $IC_{50}$ to the dopamine transporter at about 0.1 nm, 1 nm, 10 nm, 100 nm, or 1 μm, or any subrange thereof. In some embodiments, the inhibitor of a dopamine transporter has a functional potency $IC_{50}$ to the dopamine transporter at about 3 nm, 10 nm, 20 nm, 30 nm, 40 nm, 50 nm, 60 nm, 70 nm, 80 nm, 90 nm, 100 nm, 200 nm, 300 nm, or any subrange thereof.

In some embodiments, the medication can comprise a norepinephrine reuptake inhibitor (NRI), e.g., atomoxetine or reboxetine, a dopamine reuptake inhibitor, e.g., bupropion or methylphenidate, a selective serotonin and norepinephrine reuptake inhibitor (SSNRI or SNRI), e.g., venlafaxine, desvenlafaxine, or duloxetine, or a selective serotonin reuptake inhibitor (SSRI), e.g., fluoxetine, citalopram, or escitalopram.

The medication can comprise a serotonin-norepinephrine-dopamine reuptake inhibitor (SNDRL a triple reuptake inhibitor or TRI). Any suitable serotonin-norepinephrine-dopamine reuptake inhibitor can be used. For example, the serotonin-norepinephrine-dopamine reuptake inhibitor can be a compound of Formula (I):

(I)

wherein:
the chiral center to which X is attached is in the R or S configuration;
X is selected from the group consisting of indenyl, indanyl, naphthyl, dihydronaphthyl, tetrahydronaphthyl, benzocycloheptenyl, dihydrobenzocycloheptenyl, and tetrahydrobenzocycloheptenyl;
$R^1$ is H or methyl, preferably, R1 is methyl;
$R^2$ is H;
$R^3$ is H
$R^4$ is selected from the group consisting of pyridazin-3-yl, 6-methylpyridazin-3-yl, 6-dimethylamino-pyridin-3-yl, 6-methylamino-pyridazin-3-yl, 6-amino-pyridazin-3-yl, 6-morpholino-4-yl-pyridazin-3-yl, 6-trifluoromethyl-pyridazin-3-yl, 6-cyano-pyridazin-3-yl, and pyridazin-4-yl;

$R^5$ is H or F;

$R^6$ is H, F or methoxy;

$R^7$ is H; and $R^8$ is H, OH, $OCH_3$, —CN, F, Cl, or $CH_3$;

or an oxide thereof;

or a pharmaceutically acceptable salt thereof .

In some embodiments, $R^4$ is 6-amino-pyridazin-3-yl; or a pharmaceutically acceptable salt thereof.

In some embodiments, X is naphthalen-2-yl; or a pharmaceutically acceptable salt thereof.

In some embodiments, the chiral center to which X is attached is in the S configuration; or a pharmaceutically acceptable salt thereof.

In some embodiments, the compound is a (+) stereoisomer; or a pharmaceutically acceptable salt thereof.

In some embodiments, the compound is of the formula:

or a pharmaceutically acceptable salt thereof.

In some embodiments, the compound is of the formula:

or a pharmaceutically acceptable salt thereof.

In some embodiments, the compound is des-methyl metabolite (BMS-821007).

In some embodiments, the serotonin-norepinephrine-dopamine reuptake inhibitor is a compound of the formula (II):

(II)

or a pharmaceutically acceptable salt thereof, e.g., a HCl salt thereof.

In some embodiments, the serotonin-norepinephrine-dopamine reuptake inhibitor is liafensine, BMS-866949, or an analogue or derivative thereof, or a pharmaceutically acceptable salt thereof.

In some embodiments, the serotonin-norepinephrine-dopamine reuptake inhibitor is Mazindol, Nefazodone, sibutramine, Venlafaxine, Esketamine, Ketamine, Phencyclidine (PCP), Tripelennamine, Mepiprazole, Amitifadine, AN-788, Ansofaxine hydrochloride, Centanafadine, Dasotraline, Lu. AA34893, Lu AA37096, NS-2360, Tedatioxetine Tesofensine, Bicifadine (DOV-220,075), BMS 866, 949, Bra.sofensine, Diclofensine (Ro 8-4650), DOV 216, 303, EXP-561, NS-2359, RG-7166, SEP-227,162, SEP-228, 425, SEP-228.432, 3-Methyl-PCPy, Naphyrone, 3,3,-Diphenylcyclobutanatnine, 3,4-Dichlorotametraline, D-161, Desmethylsertraline (DMS), N,O-Dimethyl-4β-(2-naphthyl)piperidine-3β-carboxylate (DMNPC), DONT-102,677, Fezolamine (Win-4L528-2), GSK1360707F, Indatraline (Lu 19-005), JNJ-7925476, LR-5182, HDMP-28 (methylnaphthida.te), MI-4, PRC200-SS, SKY-83,959, TP1. NS9775, a phenyltropane, SEP-225289, GSK372475, or a herbal substance. Any suitable phenyltropane can be used. For example, the phenyltropane can be WF-23, Dichloropane or RTI-55. Any suitable herbal substance can be used. For example, the herbal substance can comprise Coca flour, Ginkgo biloba extract, Hypericuin performatum, (St John's wort), Oregano extract, rosemary extract, or Hederagenin.

The present kit, reagent, or microarray can further comprise a medication for treating major depressive disorder (MDD or depression) or a medication for modulating level(s) of serotonin (5-HT), norepinephrine (NE) and/or dopamine (DA) in a subject. The present kit, reagent, or microarray can further comprise any suitable medication for treating major depressive disorder (MDD or depression) or a medication for modulating level(s) of serotonin (5-HT), norepinephrine (NE) and/or dopamine (DA) in a subject, e.g., any of the medication described above. In some embodiments, the medication comprises: a) liafensine (BMS-820836 or AMR-000013), BMS-866949 (CSTI-500 or AMR-001181), or an analogue or derivative thereof; or b) an inhibitor of a serotonin transporter (SERT), a norepinephrine transporter (NET) and/or a dopamine transporter (DAT), e.g., a serotonin-norepinephrine-dopamine reuptake inhibitor.

D. Companion Diagnostic and Other Methods

In yet another aspect, the present disclosure provides for a companion diagnostic method, comprising: a) assaying a biological sample from a subject that is undergoing a treatment or is considered for a treatment for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the r² value between said SNP and rs12217173 being equal to or greater than about 0.800, and a complementary SNP thereof; and/or b) generating an output, e.g., a score, for example with a computer algorithm based on the assay results of said SNP or SNPs, in order to determine the likely responsiveness of said subject to said treatment.

In yet another aspect, the present disclosure provides for a method for classifying a subject for eligibility for a treatment, comprising: a) assaying a biological sample from a subject that is undergoing a treatment or is considered for a treatment for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the r² value between said SNP and rs12217173 being equal to or greater than about 0.800, and a complementary SNP thereof; and/or b) generating an output, e.g., a score, for example with a computer algorithm based on the assay results of said SNP or SNPs, in order to classify the subject as eligible or ineligible for the treatment or continued treatment.

In yet another aspect, the present disclosure provides for a method for screening a subject or a population of subjects for a treatment, comprising: a) assaying a biological sample(s) from a subject or a population of subjects that is undergoing a treatment or is considered for a treatment for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the r² value between said SNP and rs12217173 being equal to or greater than about 0.800, and a complementary SNP thereof; and/or b) generating an output, e.g., a score, for example with a computer algorithm based on the assay results of said SNP or SNPs, in order to determine whether the subject or the population is likely to benefit from the treatment or continued treatment, and/or to determine whether the subject or the population is likely to experience an adverse effect from the treatment or continued treatment.

In yet another aspect, the present disclosure provides for a method for monitoring a subject during a treatment, comprising: a) assaying a biological sample from a subject undergoing a treatment for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the r² value between said SNP and rs12217173 being equal to or greater than about 0.800, and a complementary SNP thereof and/or b) generating an output, e.g., a score, for example with a computer algorithm based on the assay results of said SNP or SNPs, in order to determine whether the subject should receive continued treatment.

In some embodiments, the present methods can further comprise obtaining a biological sample from a subject that is undergoing a treatment or is considered for a treatment.

In some embodiments, the present methods can further comprise isolating genomic DNA from a biological sample from a subject that is undergoing a treatment or is considered for a treatment.

In some embodiments, the present methods can further comprise subjecting the subject to the treatment, e.g., a treatment for a CNS disease or disorder such as a major depressive disorder (MDD).

In some embodiments, the present methods can further comprise continuing the treatment on the subject, e.g., a treatment for a CNS disease or disorder such as a major depressive disorder (MDD).

In some embodiments, the present methods can further comprise not recommending the treatment on the subject, modifying the treatment on the subject, or withdrawing the subject from the treatment, e.g., a treatment for a CNS disease or disorder such as a major depressive disorder (MDD).

The present methods can comprise assaying a biological sample from a subject that is undergoing a treatment or is considered for a treatment for any suitable one or more single nucleotide polymorphisms (SNPs). In some embodiments, the present methods comprise assaying a biological sample from a subject for the one or more SNPs selected from the group consisting of rs12217173, a SNP listed in any of Tables 1A-1E, or a complementary SNP thereof. In some embodiments, the present methods comprise assaying a biological sample from a subject for the one or more SNPs selected from the group consisting of rs12217173, rs12219340, rs4612751, rs12572120, or a complementary SNP thereof. In some embodiments, the present methods comprise assaying a biological sample from a subject for rs12217173 or a complementary SNP thereof. In some embodiments, the present methods comprise assaying a biological sample from a subject for the one or more SNPs comprising a sequence set forth in any of the sequences set forth in SEQ ID NOs: 1-51, a complementary sequence thereof, or a sequence in linkage disequilibrium therewith. In some embodiments, the present methods comprise assaying a biological sample from a subject for the one or more SNPs comprising a sequence set forth in SEQ ID NOs: 51, 1, 2, or 5, a complementary sequence thereof, or a sequence in linkage disequilibrium therewith. In some embodiments, the present methods comprise assaying a biological sample from a subject for the one or more SNPs comprising a sequence set forth in SEQ ID NO:51, a complementary sequence thereof, or a sequence in linkage disequilibrium therewith.

The isolated biomarker or panel can be assayed using any suitable techniques or procedures. For example, the isolated biomarker or panel can be assayed by sequencing, polymerase chain reaction (PCR), capillary electrophoresis, mass spectrometry, single-strand conformation polymorphism (SSCP), electrochemical analysis, denaturing HPLC and gel electrophoresis, restriction fragment length polymorphism, hybridization analysis, single-base extension (SBE), allele specific primer extension (ASPE), restriction enzyme digestion, strand displacement amplification (SDA), transcription mediated amplification (TMA), ligase chain reaction (LCR), nucleic acid sequence based amplification (NASBA), primer extension, rolling circle amplification (RCA), self sustained sequence replication (3 SR), loop-mediated isothermal amplification (LAMP), hybridization, nucleic acid sequencing, and/or microarray. Any suitable nucleic acid sequencing techniques or procedures can be used. For example, the nucleic acid sequencing can be Maxam-Gilbert sequencing, a chain-termination method, shotgun sequencing, bridge PCR, single-molecule real-time sequencing, ion semiconductor (ion torrent sequencing), sequencing by synthesis, sequencing by ligation (SOLiD sequencing), chain termination (Sanger sequencing), massively parallel signature sequencing (1MPSS), polony sequencing, 454 pyrosequencing, Illumina (Solexa) sequencing, DNA nanoball sequencing, heliscope single molecule sequencing, single molecule real time (SMRT) sequencing, nanopore DNA sequencing, tunnelling currents DNA sequencing, sequencing by hybridization, sequencing with mass spectrometry, microfluidic Sanger sequencing, a microscopy-based technique, RNAP sequencing, and/or in vitro virus high-throughput sequencing.

The present methods can be used to assess any suitable treatment. For example, the present methods can be used to assess a treatment for major depressive disorder (MDD or depression) or a disease or disorder associated with abnormal level(s) of serotonin (5-HT), norepinephrine (NE) and/or dopamine (DA). The disease or disorder can be a central nervous system (CNS) disease or disorder. In some embodiments, the CNS disease or disorder is a major depressive disorder (MDD), e.g., a subtype of MDD, or a major depression with psychotic feature(s) and/or depression with peri- or postpartum onset, a post-traumatic stress disorder (PTSD), a bipolar disorder, an obsessive-compulsive disorder (OCD), an eating disorder, attention-deficit hyperactivity disorder (ADHD), a sleep disorder, e.g., narcolepsy, a substance use disorder, Tourette syndrome (TS), schizophrenia, epilepsy, migraine, or an autism spectrum disorder. The neurodegenerative disorder can be Alzheimer's disease (AD) Huntington's disease, or Parkinson's disease (PD). In some embodiments, the present methods can be used to assess a treatment for major depressive disorder (MDD or depression), or a subtype of MDD, e.g., major depression with psychotic feature(s) and/or depression with peri- or postpartum onset.

The present methods can be used to assess a treatment using any suitable medication. For example, the present methods can be used to assess a treatment that comprises administering to the subject in need thereof a pharmaceutically effective amount of a medication for treating major depressive disorder (MDD or depression) or a medication for modulating level(s) of serotonin (5-HT), norepinephrine (NE) and/or dopamine (DA) in a subject. In some embodiments, the present methods can be used to assess a treatment for major depressive disorder or for modulating level(s) of serotonin, norepinephrine and/or dopamine using liafensine (BMS-820836 or AMR-000013), BMS-866949 (CSTI-500 or AMR-001181), or an analogue or derivative thereof. In some embodiments, the present methods can be used to assess a treatment for major depressive disorder or for modulating level(s) of serotonin, norepinephrine and/or dopamine using an inhibitor of a serotonin transporter (SERT), a norepinephrine transporter (NET) and/or a dopamine transporter (DAT).

Any suitable inhibitor of a serotonin transporter can be used. For example, the inhibitor of a serotonin transporter can have: a) a binding affinity $IC_{50}$ to the serotonin transporter ranging from about 0.1 nm to about 1 μm, e.g., from about 0.1 nm to about 60 nm; and/or b) a functional potency $IC_{50}$ to the serotonin transporter ranging from about 0.1 nm to about 1 μm, e.g., from about 2 nm to about 200 nm. In some embodiments, the inhibitor of a serotonin transporter has a binding affinity $IC_{50}$ to the serotonin transporter at about 0.1 nm, 1 nm, 10 nm, 100 nm, or 1 μm, or any subrange thereof. In some embodiments, the inhibitor of a serotonin transporter has a binding affinity $IC_{50}$ to the serotonin transporter at about 0.1 nm, 1 nm, 10 nm, 20 nm, 30 nm, 40 nm, 50 nm, 60 nm, or any subrange thereof. In some embodiments, the inhibitor of a serotonin transporter has a functional potency $IC_{50}$ to the serotonin transporter at about 0.1 nm, 1 nm, 10 nm, 100 nm, or 1 μm, or any subrange thereof. In some embodiments, the inhibitor of a serotonin transporter has a functional potency $IC_{50}$ to the serotonin transporter at about 2 nm, 10 nm, 20 nm, 30 nm, 40 nm, 50 nm, 60 nm, 70 nm, 80 nm, 90 nm, 100 nm, 150 nm, 200 nm, or any subrange thereof.

Any suitable inhibitor of a norepinephrine transporter can be used. For example, the inhibitor of a norepinephrine transporter can have: a) an binding affinity $IC_{50}$ to the norepinephrine transporter ranging from about 1 nm to about 1 μm, e.g., from about 0.8 nm to about 80 nm; and/or b) a functional potency $IC_{50}$ to the norepinephrine transporter ranging from about 0.1 nm to about 1 μm, e.g., from about 4 nm to about 400 nm. In some embodiments, the inhibitor of a norepinephrine transporter has a binding affinity $IC_{50}$ to the norepinephrine transporter at about 0.1 nm, 1 nm, 10 nm, 100 nm, or 1 μm, or any subrange thereof. In some embodiments, the inhibitor of a norepinephrine transporter has a binding affinity $IC_{50}$ to the norepinephrine transporter at about 0.8 nm, 1 nm, 10 nm, 20 nm, 30 nm, 40 nm, 50 nm, 60 nm, 70 nm, 80 nm, or any subrange thereof. In some embodiments, the inhibitor of a norepinephrine transporter has a functional potency $IC_{50}$ to the norepinephrine transporter at about 0.1 nm, 1 nm, 10 nm, 100 nm, or 1 μm, or any subrange thereof. In some embodiments, the inhibitor of a norepinephrine transporter has a functional potency $IC_{50}$ to the norepinephrine transporter at about 4 nm, 10 nm, 20 nm, 30 nm, 40 nm, 50 nm, 60 nm, 70 nm, 80 nm, 90 nm, 100 nm, 200 nm, 300 nm, 400 nm, or any subrange thereof.

Any suitable inhibitor of a dopamine transporter can be used. For example, the inhibitor of a dopamine transporter can have: a) an binding affinity $IC_{50}$ to the dopamine transporter ranging from about 1 nm to about 1 μm, e.g., from about 0.6 nm to about 60 nm; and/or b) a functional potency $IC_{50}$ to the dopamine transporter ranging from about 0.1 nm to about 1 μm, e.g., from about 3 nm to about 300 nm. In some embodiments, the inhibitor of a dopamine transporter has an binding affinity $IC_{50}$ to the dopamine transporter at about 0.1 nm, 1 nm, 10 nm, 100 nm, or 1 μm, or any subrange thereof. In some embodiments, the inhibitor of a dopamine transporter has an binding affinity $IC_{50}$ to the dopamine transporter at about 0.6 nm, 1 nm, 10 nm, 20 nm, 30 nm, 40 nm, 50 nm, 60 nm, or any subrange thereof. In some embodiments, the inhibitor of a dopamine transporter has a functional potency $IC_{50}$ to the dopamine transporter at about 0.1 nm, 1 nm, 10 nm, 100 nm, or 1 μm, or any subrange thereof. In some embodiments, the inhibitor of a dopamine transporter has a functional potency $IC_{50}$ to the dopamine transporter at about 3 nm, 10 nm, 20 nm, 30 nm, 40 nm, 50 nm, 60 nm, 70 nm, 80 nm, 90 nm, 100 nm, 200 nm, 300 nm, or any subrange thereof.

In some embodiments, the present methods can be used to assess a treatment for major depressive disorder or for modulating level(s) of serotonin, norepinephrine and/or dopamine using a norepinephrine reuptake inhibitor (NRI), e.g., atomoxetine or reboxetine, a dopamine reuptake inhibitor, e.g., bupropion or methylphenidate, a selective serotonin and norepinephrine reuptake inhibitor (SSNRI or SNRI), e.g., venlafaxine, desvenlafaxine, or duloxetine, or a selective serotonin reuptake inhibitor (SSRI), e.g., fluoxetine, citalopram, or escitalopram.

In some embodiments, the present methods can be used to assess a treatment for major depressive disorder or for modulating level(s) of serotonin, norepinephrine and/or dopamine using a serotonin-norepinephrine-dopamine reuptake inhibitor (SNDRI, a triple reuptake inhibitor or TRI). Any suitable serotonin-norepinephrine-doparn in e reuptake inhibitor can be used. For example, the serotonin-norepi-nephrine-dopamine reuptake inhibitor can be a compound of Formula (I):

(I)

wherein:

the chiral center to which X is attached is in the R or S configuration;

X is selected from the group consisting of indenyl, indanyl, naphthyl, dihydronaphthyl, tetrahydronaphthyl, benzocy-cloheptenyl, dihydrobenzocycloheptenyl, and tetrahyd-robenzocycloheptenyl;

$R^1$ is H or methyl, preferably, R1 is methyl;

$R^2$ is H;

$R^3$ is H $R^4$ is selected from the group consisting of pyridazin-3-yl, 6-methylpyridazin-3-yl, 6-dimethylamino-pyridin-3-yl, 6-methylamino-pyridazin-3-yl, 6-amino-pyridazin-3-yl, 6-morpholino-4-yl-pyridazin-3-yl, 6-trifluoromethyl-pyridazin-3-yl, 6-cyano-pyridazin-3-yl, and pyridazin-4-yl;

$R^5$ is H or F;

$R^6$ is H, F or methoxy;

$R^7$ is H; and $R^8$ is H, OH, $OCH_3$, —CN, F, Cl, or $CH_3$;

or an oxide thereof;

or a pharmaceutically acceptable salt thereof.

In some embodiments, $R^4$ is 6-amino-pyridazin-3-yl; or a pharmaceutically acceptable salt thereof.

In some embodiments, X is naphthalen-2-yl; or a phar-maceutically acceptable salt thereof.

In some embodiments, the chiral center to which X is attached is in the S configuration; or a pharmaceutically acceptable salt thereof.

In some embodiments, the compound is a (+) stereoiso-mer; or a pharmaceutically acceptable salt thereof.

In some embodiments, the compound is of the formula:

or a pharmaceutically acceptable salt thereof.

In some embodiments, the compound is of the formula:

or a pharmaceutically acceptable salt thereof.

In some embodiments, the compound is des-methyl metabolite (BMS-821007).

In some embodiments, the serotonin-norepinephrine-do-pamine reuptake inhibitor is a compound of the formula (II):

(II)

or a pharmaceutically acceptable salt thereof, e.g., a HCl salt thereof.

In some embodiments, the present methods can be used to assess a treatment for major depressive disorder or for modulating level(s) of serotonin, norepinephrine and/or dop-amine using liafensine, BMS-866949, or an analogue or derivative thereof; or a pharmaceutically acceptable salt thereof.

In some embodiments, the present methods can be used to assess a treatment for major depressive disorder or for modulating level(s) of serotonin, norepinephrine and/or dop-amine using Mazindol, Nefazodone, sibutramirie, Venlafax-ine, Esketamine, Ketamine, Phencyclidine (PCP), Tripelennarnine, Mepiprazole, Amitifadine, AN-788, Anso-faxine hydrochloride, Centanafadine, Dasotraline, Lu AA34893, Lu AA37096, NS-2360, Tedatioxetine, Tes-ofensine, Bicifadine (DOV-220,075), BMS 866,949, Brasofensine, Diclofensine (Ro 8-4650), DOV 216,303, EXP-561, NS-2359, RG-7166, SEP-227,162, SEP-228,425, SEP-228,432, 3-Methyl-PCPy, Naphyrone, 3,3,-Diphenyl-cyclobutanamine, 3,4-Dichlorotametraline, D-161, Desm-ethylsertraline (DMS), N,O-Dimethyl-4β-(2-naphthyl)pip-eridine-3β-carboxylate (DMNPC), DOV-102,677, Fezolamine (Win-41,528-2), GSK1360707F, Indatraline (Lu 19-005), JNJ-7925476, LR-5182, HDMP-28 (methylriaph-thidate), MI-4, PRC200-SS, SKF-83,959, TP1, NS9775, a phenyltropane, SEP-225289, GSK372475, or a herbal sub-stance. Any suitable phenyltropane can be used, e.g., WF-23, Dichloropane, or RTI-55. Any suitable herbal substance can be used, e.g., Coca flour, Ginkgo bilobci extract, Hypericum perforatum, (St John's wort), Oregano extract, rosemary extract, or Hederagenin.

The present methods can be used to assess a treatment for major depressive disorder or for modulating level(s) of serotonin, norepinephrine and/or dopamine that further comprises administering another medication to a subject for treating major depressive disorder (MDD or depression) or a disease or disorder associated with abnormal level(s) of serotonin (5-HT), norepinephrine (NE) and/or dopamine (DA). Any suitable other medication can be used. In some embodiments, the other medication can be an antidepressant, Omega-3 fatty acids, vitamin D, a COX-2 inhibitor, e.g., Celecoxib, a lithium compound, a thyroid hormone, a stimulant (or a psychostimulant), e.g., Amphetamine or Modafinil, fol ate, or testosterone.

In yet another aspect, the present disclosure provides for a method of identifying a new biomarker using one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof. Any suitable SNP(s) can be used in the present methods, e.g., the SNP(s) disclosed in the present disclosure. For example, rs12217173, or a complementary SNP thereof can be used in the present methods. The new biomarker can be any suitable type of substance. For example, the new biomarker can be a DNA, a RNA, a polypeptide, a siRNA or another form of biomarker.

In yet another aspect, the present disclosure provides for a method of identifying a drug target using one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof. Any suitable SNP(s) can be used in the present methods, e.g., the SNP(s) disclosed in the present disclosure. For example, rs12217173, or a complementary SNP thereof can be used in the present methods. The drug target can be identified based on any suitable type of parameter. For example, the drug target can be identified based on a biological pathway related to the one or more SNPs.

E. Methods of Treatment

In yet another aspect, the present disclosure provides for a method for treating a central nervous system (CNS) disease or disorder in a subject, which method comprises administering an effective amount of: a) liafensine (BMS-820836 or AMR-000013), BMS-866949 (CSTI-500 or AMR-001181), or an analogue or derivative thereof; or b) an inhibitor of a serotonin transporter (SERT), a norepinephrine transporter (NET) and/or a dopamine transporter (DAT), to a subject that is in need for the treatment and has homozygous minor allele for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof.

The present methods can be used on a subject that is in need for the treatment and has homozygous minor allele for any suitable one or more SNPs. In some embodiments, the present methods can be used on a subject that is in need for the treatment and has homozygous minor allele for one or more SNPs are selected from the group consisting of rs12217173, a SNP listed in any of Tables 1A-1E, or a complementary SNP thereof. In some embodiments, the present methods can be used on a subject that is in need for the treatment and has homozygous minor allele for one or more SNPs are selected from the group consisting of rs12217173, rs12219340, rs4612751, rs12572120, or a complementary SNP thereof. In some embodiments, the present methods can be used on a subject that is in need for the treatment and has homozygous minor allele for one or more SNPs that is rs12217173, or a complementary SNP thereof, and the homozygous minor allele is GG. In some embodiments, the present methods can be used on a subject that is in need for the treatment and has homozygous minor allele for the SNP or SNPs that comprise a sequence set forth in any of the sequences set forth in SEQ ID NOs: 1-51, a complementary sequence thereof, or a sequence in linkage disequilibrium therewith. In some embodiments, the present methods can be used on a subject that is in need for the treatment and has homozygous minor allele for the SNP or SNPs that comprise a sequence set forth in SEQ ID NOs: 51, 1, 2, or 5, a complementary sequence thereof, or a sequence in linkage disequilibrium therewith. In some embodiments, the present methods can be used on a subject that is in need for the treatment and has homozygous minor allele for the SNP or SNPs that comprise a sequence set forth in SEQ ID NO:51, a complementary sequence thereof, or a sequence in linkage disequilibrium therewith, and the homozygous minor allele is GG.

The present methods can be used to treat any suitable CNS diseases or disorders. For example, the present methods can be used to treat a CNS disease or disorder that is associated with abnormal level(s) of serotonin (5-HT), norepinephrine (NE) and/or dopamine (DA) in a subject, e.g., in the synapse of the subject. The the CNS disease or disorder can be a major depressive disorder (MDD), e.g., a subtype of MDD, or a major depression with psychotic feature(s) and/or depression with peri- or postpartum onset, a posttraumatic stress disorder (PTSD), a bipolar disorder, an obsessive-compulsive disorder (OCD), an eating disorder, attention-deficit hyperactivity disorder (ADHD), a sleep disorder, e.g., narcolepsy, a substance use disorder, Tourette syndrome (TS), schizophrenia, epilepsy, migraine, or an autism spectrum disorder. The neurodegenerative disorder can be Alzheimer's disease (AD) Huntington's disease, or Parkinson's disease (PD). In some embodiments, the present methods can be used to treat a major depressive disorder (MDD or depression) or a subtype of MDD, e.g., major depression with psychotic feature(s) and/or depression with peri- or postpartum onset.

Any suitable inhibitor of a serotonin transporter can be used. For example, the inhibitor of a serotonin transporter can have: a) a binding affinity $IC_{50}$ to the serotonin transporter ranging from about 0.1 nm to about 1 μm, e.g., from about 0.1 nm to about 60 nm; and/or b) a functional potency $IC_{50}$ to the serotonin transporter ranging from about 0.1 nm to about 1 μm, e.g., from about 2 nm to about 200 nm. In some embodiments, the inhibitor of a serotonin transporter has a binding affinity $IC_{50}$ to the serotonin transporter at about 0.1 nm, 1 nm, 10 nm, 100 nm, or 1 μm, or any subrange thereof. In some embodiments, the inhibitor of a serotonin transporter has a binding affinity $IC_{50}$ to the serotonin transporter at about 0.1 nm, 1 nm, 10 nm, 20 nm, 30 nm, 40 nm, 50 nm, 60 nm, or any subrange thereof. In some embodiments, the inhibitor of a serotonin transporter has a functional potency $IC_{50}$ to the serotonin transporter at about 0.1 nm, 1 nm, 10 nm, 100 nm, or 1 μm, or any subrange thereof. In some embodiments, the inhibitor of a serotonin transporter has a functional potency $IC_{50}$ to the serotonin transporter at about 2 nm, 10 nm, 20 nm, 30 nm, 40 nm, 50 nm, 60 nm, 70 nm, 80 nm, 90 nm, 100 nm, 150 nm, 200 nm, or any subrange thereof.

Any suitable inhibitor of a norepinephrine transporter can be used. For example, the inhibitor of a norepinephrine transporter can have: a) an binding affinity $IC_{50}$ to the norepinephrine transporter ranging from about 1 nm to about 1 μm, e.g., from about 0.8 nm to about 80 nm; and/or b) a functional potency $IC_{50}$ to the norepinephrine transporter ranging from about 0.1 nm to about 1 μm, e.g., from about 4 nm to about 400 nm. In some embodiments, the inhibitor of a norepinephrine transporter has a binding affinity $IC_{50}$ to the norepinephrine transporter at about 0.1 nm, 1 nm, 10 nm, 100 nm, or 1 μm, or any subrange thereof. In some embodiments, the inhibitor of a norepinephrine transporter has a binding affinity $IC_{50}$ to the norepinephrine transporter at about 0.8 nm, 1 nm, 10 nm, 20 nm, 30 nm, 40 nm, 50 nm, 60 nm, 70 nm, 80 nm, or any subrange thereof. In some embodiments, the inhibitor of a norepinephrine transporter has a functional potency $IC_{50}$ to the norepinephrine transporter at about 0.1 nm, 1 nm, 10 nm, 100 nm, or 1 μm, or any subrange thereof. In some embodiments, the inhibitor of a norepinephrine transporter has a functional potency $IC_{50}$ to the norepinephrine transporter at about 4 nm, 10 nm, 20 nm, 30 nm, 40 nm, 50 nm, 60 nm, 70 nm, 80 nm, 90 nm, 100 nm, 200 nm, 300 nm, 400 nm, or any subrange thereof.

Any suitable inhibitor of a dopamine transporter can be used. For example, the inhibitor of a dopamine transporter can have: a) an binding affinity $IC_{50}$ to the dopamine transporter ranging from about 1 nm to about 1 μm, e.g., from about 0.6 nm to about 60 nm; and/or b) a functional potency $IC_{50}$ to the dopamine transporter ranging from about 0.1 nm to about 1 μm, e.g., from about 3 nm to about 300 nm. In some embodiments, the inhibitor of a dopamine transporter has an binding affinity $IC_{50}$ to the dopamine transporter at about 0.1 nm, 1 nm, 10 nm, 100 nm, or 1 μm, or any subrange thereof. In some embodiments, the inhibitor of a dopamine transporter has an binding affinity $IC_{50}$ to the dopamine transporter at about 0.6 nm, 1 nm, 10 nm, 20 nm, 30 nm, 40 nm, 50 nm, 60 nm, or any subrange thereof. In some embodiments, the inhibitor of a dopamine transporter has a functional potency $IC_{50}$ to the dopamine transporter at about 0.1 nm, 1 nm, 10 nm, 100 nm, or 1 μm, or any subrange thereof. In some embodiments, the inhibitor of a dopamine transporter has a functional potency $IC_{50}$ to the dopamine transporter at about 3 nm, 10 nm, 20 nm, 30 nm, 40 nm, 50 nm, 60 nm, 70 nm, 80 nm, 90 nm, 100 nm, 200 nm, 300 nm, or any subrange thereof.

In some embodiments, the present methods can use a norepinephrine reuptake inhibitor (NRI), e.g., atomoxetine or reboxetine, a dopamine reuptake inhibitor, e.g., bupropion or methylphenidate, a selective serotonin and norepinephrine reuptake inhibitor (SSNRI or SNRI), e.g., venlafaxine, desvenlafaxine, or duloxetine, or a selective serotonin reuptake inhibitor (SSRI), e.g., fluoxetine, citalopram, or escitalopram.

In some embodiments, the present methods can use a serotonin-norepinephrine-dopamine reuptake inhibitor (SN-DRI, a triple reuptake inhibitor or TRI). Any suitable serotonin-norepinephrine-dopamine reuptake inhibitor can be used. For example, the serotonin-norepinephrine-dopamine reuptake inhibitor can be a compound of Formula (I):

(I)

wherein:

the chiral center to which X is attached is in the R or S configuration;

X is selected from the group consisting of indenyl, indanyl, naphthyl, dihydronaphthyl, tetrahydronaphthyl, benzocycloheptenyl, dihydrobenzocycloheptenyl, and tetrahydrobenzocycloheptenyl;

$R^1$ is H or methyl, preferably, R1 is methyl;

$R^2$ is H;

$R^3$ is H $R^4$ is selected from the group consisting of pyridazin-3-yl, 6-methylpyridazin-3-yl, 6-dimethylamino-pyridin-3-yl, 6-methylamino-pyridazin-3-yl, 6-amino-pyridazin-3-yl, 6-morpholino-4-yl-pyridazin-3-yl, 6-trifluoromethyl-pyridazin-3-yl, 6-cyano-pyridazin-3-yl, and pyridazin-4-yl;

$R^5$ is H or F;

$R^6$ is H, F or methoxy;

$R^7$ is H; and $R^8$ is H, OH, $OCH_3$, —CN, F, Cl, or $CH_3$;

or an oxide thereof;

or a pharmaceutically acceptable salt thereof. Preferably, R1 is methyl.

In some embodiments, $R^4$ is 6-amino-pyridazin-3-yl; or a pharmaceutically acceptable salt thereof.

In some embodiments, X is naphthalen-2-yl; or a pharmaceutically acceptable salt thereof.

In some embodiments, the chiral center to which X is attached is in the S configuration; or a pharmaceutically acceptable salt thereof.

In some embodiments, the compound is a (+) stereoisomer; or a pharmaceutically acceptable salt thereof.

In some embodiments, the compound is of the formula:

or a pharmaceutically acceptable salt thereof.

In some embodiments, the compound is of the formula:

or a pharmaceutically acceptable salt thereof.

In some embodiments, the compound is des-methyl metabolite (BMS-821007).

In some embodiments, the serotonin-norepinephrine-dopamine reuptake inhibitor is a compound of the formula (II):

(II)

or a pharmaceutically acceptable salt thereof, e.g., a HCl salt thereof.

In some embodiments, the present methods can use liafensine, BMS-866949, or an analogue or derivative thereof, or a pharmaceutically acceptable salt thereof.

In some embodiments, the present methods can use a serotonin-norepinephrine-dopamine reuptake inhibitor that is Mazindol, Nefazodone, sibutramine, Venlafaxine, Esketamine, Ketamine, Phencyclidine (PCP), Tripelennamine, Mepiprazole, Amitifadine, AN-788, Ansofaxine hydrochloride, Centanafadine, Dasotraline, Lu AA34893, Lu AA37096, NS-2360, Tedatioxetine, Tesofensine, Bicifadine (DOV-220,075), BMS 866,949, Brasofensine, Diclofensine (Ro 8-4650), DOV 216,303, EXP-561, NS-2359, RG-7166, SEP-227,162, SEP-228,425, SEP-228,432, 3-Methyl-PCPy, Naphyrone, 3,3,-Diphenylcyclobutanamine, 3,4-Dichlorotametraline, D-161 Desmethylsertraline (DMS), N,O-Dimethyl-4β-(2-naphthyl)piperidine-3β-carboxylate (DMNPC), DOV-102,677, Fezolamine (Win-41,528-2), GSK1360707F, Indatraline (Lu 19-005), JNJ-7925476, LR-5182, EIDMP-28 (methylnaphthidate), MI-4, PRC200-SS, SKF-83,959, TP1, NS9775, a phenyltropane, SEP-225289, GSK372475, or a herbal substance. Any suitable phenyltropane can be used, e.g., WF-23, Dichloropane or RTI-55. Any suitable herbal substance can be used, e.g., Coca flour, Ginkgo biloba extract, Ilypericinn per:fon:num, (St John's wort), Oregano extract, rosemary extract, or Hederagenin.

The present methods can further comprise administering another medication to a subject for treating major depressive disorder (MDD or depression) or a disease or disorder associated with abnormal level(s) of serotonin (5-HT), norepinephrine (NE) and/or dopamine (DA). Any suitable other medication can be used, e.g., an antidepressant, Omega-3 fatty acids, vitamin D, a COX-2 inhibitor, e.g., Celecoxib, a lithium compound, a thyroid hormone, a stimulant (or a psychostirnulant), e.g., Amphetamine or Modafinil, folate, or testosterone.

The present methods can be used to treat any suitable subject. For example, the present methods can comprise administering an effective amount of: a) liafensine (BMS-820836 or AMR-000013), BMS-866949 (CSTI-500 or AMR-001181), or an analogue or derivative thereof; orb) an inhibitor of a serotonin transporter (SERT), a norepinephrine transporter (NET) and/or a dopamine transporter (DAT), to a subject that has been treated with another inhibitor of a serotonin transporter, a norepinephrine transporter and/or a dopamine transporter and has not responded or has not responded well to the other inhibitor of a serotonin transporter, a norepinephrine transporter and/or a dopamine transporter. The other inhibitor can be a norepinephrine reuptake inhibitor (NM), e.g., atomoxetine or reboxetine, a dopamine reuptake inhibitor, e.g., bupropion or methylphenidate, a selective serotonin and norepinephrine reuptake inhibitor (SSNRI or SNRI), e.g., venlafaxine, desvenlafaxine, or duloxetine, or a selective serotonin reuptake inhibitor (SSRI), e.g., fluoxetine, citalopram, or escitalopram.

The present methods can comprise administering an effective amount of the drug substance in any suitable dosage(s). For example, the present methods can comprise administering an effective amount of: a) liafensine (BMS-820836 or AMR-000013), BMS-866949 (CSTI-500 or AMR-001181), or an analogue or derivative thereof; or b) an inhibitor of a serotonin transporter (SERT), a norepinephrine transporter (NET) and/or a dopamine transporter (DAT), to a subject in a dosage ranging from about 0.1 mg/day to about 10 mg/day, e.g., at about 0.1 mg/day, 0.5 mg/day, 1 mg/day, 2 mg/day, 3 mg/day, 4 mg/day, 5 mg/day, 6 mg/day, 7 mg/day, 8 mg/day, 9 mg/day, 10 mg/day, or any subrange thereof. In another example, the present methods can comprise administering an effective amount of liafensine to a subject in a dosage ranging from about 0.1 mg/day to about 10 mg/day, e.g., at about 0.1 mg/day, 0.5 mg/day, 1 mg/day, 2 mg/day, 3 mg/day, 4 mg/day, 5 mg/day, 6 mg/day, 7 mg/day, 8 mg/day, 9 mg/day, 10 mg/day, or any subrange thereof.

The present methods can comprise administering an effective amount of the drug substance via any suitable administration route. For example, the present methods can comprise administering an effective amount of: a) liafensine (BMS-820836 or AMR-000013), BMS-866949 (CSTI-500 or AMR-001181), or an analogue or derivative thereof; or b) an inhibitor of a serotonin transporter (SERT), a norepinephrine transporter (NET) and/or a dopamine transporter (DAT), to a subject via a route selected from the group consisting of oral, nasal, inhalational, parental, intravenous, intraperitoneal, subcutaneous, intramuscular, intradermal, topical, and rectal route.

The present methods can be used to treat any suitable subject. For example, the subject can be a human.

In yet another aspect, the present disclosure provides for an use of an effective amount of: a) liafensine (BMS-820836 or AMR-000013), BMS-866949 (CSTI-500 or AMR-001181), or an analogue or derivative thereof; or b) an inhibitor of a serotonin transporter (SERT), a norepinephrine transporter (NET) and/or a dopamine transporter (DAT), for the manufacture of a medicament for treating a central nervous system (CNS) disease or disorder in a subject that is in need for the treatment and has homozygous minor allele for one or more single nucleotide polymorphisms (SNPs) selected from the group consisting of rs12217173, a SNP in linkage disequilibrium with rs12217173 with the D' value of linkage equilibrium of said SNP being equal to or greater than about 0.900 or with the $r^2$ value between said SNP and rs12217173 being equal to or greater than about 0.800, and a complementary SNP thereof.

The use can be used for the manufacture of a medicament for treating a central nervous system (CNS) disease or disorder in any suitable subject. For example, the subject can be a human.

F. Exemplary Embodiments and Examples

In some embodiments, the present disclosure describes genomic biomarkers that have been discovered to correlate with different responses (efficacy, adverse effect, and other endpoints) among patients receiving treatment regime including DB104, in treating diseases such as depressive disorders and other central nervous system diseases. The newly discovered biomarkers can be used in companion diagnostic tests which can help to predict drug responses and apply drugs only to those who will be benefited or exclude those who might have negative outcome and/or adverse effects, by the treatment.

In some embodiments, the present disclosure comprises a method of predicting responders to therapeutic regime which includes DB104 or other inhibitors to SERT, and/or NET, and/or DAT, by using results generated by genotyping the genetic biomarkers.

The monoamine hypothesis of depression postulated a primary dysfunction in 5-HT, NE and DA systems and has guided the development of antidepressants for over forty years. Drug classes such as the tricyclic antidepressants, selective serotonin reuptake inhibitors (SSRI) and, more recently, dual (serotonin and norepinephrine) reuptake inhibitors (SNRIs) act primarily by inhibiting SERT and NET (Lane RM. 2015). DB104 is a triple reuptake inhibitor targeting SERT, NET, and DAT respectively (FIG. 1A). DB104 is being developed as monotherapy for the treatment of MDD in adults who have experienced inadequate response to separate trials of adequate dose and duration of two antidepressants from different classes in the current episode (i.e., "adults with MDD with inadequate response"). These inadequate responses are a common clinical presentation responsible for much of the disability and cost associated with MDD. It has been estimated that approximately 50% of the cost and disease burden of MDD is associated with inadequate responders to previous antidepressant treatment in the current episode. Due to the high rates of morbidity, mortality, and medical and economic costs associated with inadequate response, aggressive identification and management of inadequate responder patients is critical.

Figure 1C:
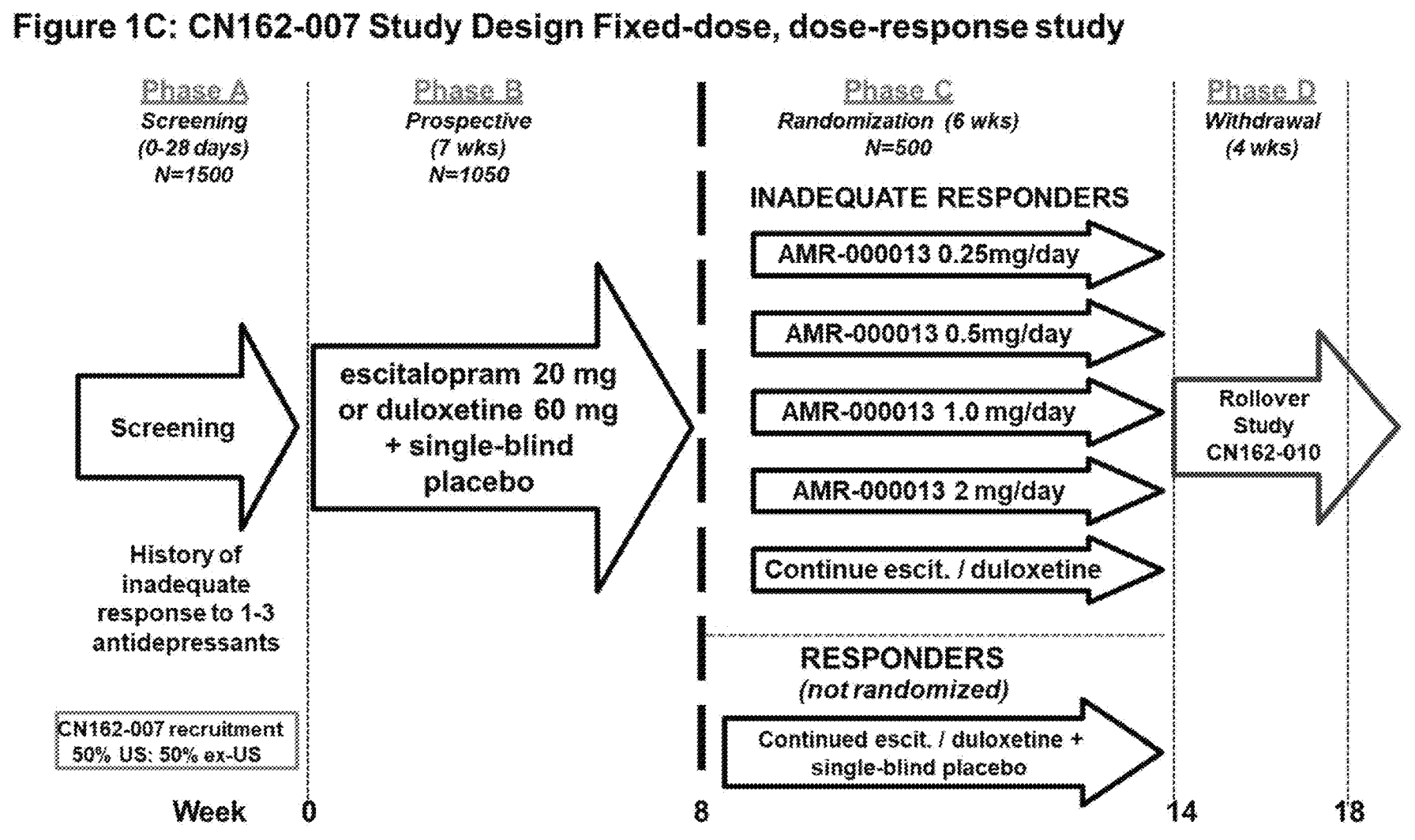

The Phase 2b program for DB104 consists of two efficacy studies (CN162006 and CN162007), and both efficacy studies have a similar design and include patients with MDD. CN162006 is flexible-dose study where patients with a history of inadequate response to at least one but less than four antidepressants and one prospective treatment (duloxetine) are switched to flexibly-dosed DB104 (0.5-2 mg/d) or remain on duloxetine (Bhagwagar Z. et al. 2015). CN162007 is a fixed dose, dose-response study where patients with a history of inadequate response to at least one but less than four antidepressants and one prospective treatment (duloxetine/escitalopram) are switched to fixed doses of DB104 (0.25, 0.5, 1, 2 mg/day) or remain on duloxetine/escitalopram (FIG. 1B and 1C). Primary endpoint is Montgomery-Asberg Depression Rating Scale (MADRS) total score change from baseline at week 6 for both studies, but neither study demonstrated significant improvement DB104 vs. continuation of duloxetine/escitalopram in primary endpoint. (Bhagwagar Z. et al. 2015.)

Figure 2:
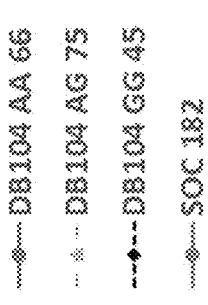
FIG. 2 illustrates exemplary correlations of different rs12217173's genotypes with DB104 efficacy inpatients from the discovery set. The mean change in MADRS total score for DB104 and standard of care (SOC) (duloxetine/escitalopram) treated patients is shown for weeks 1-6 post the baseline treatment. The error bars show the standard error of the mean. For DB104 treatment group, 186 patients that were used in the genome wide scan, and the results of the identified biomarker rs12217173 are shown. Three possible genotypes of rs12217173 were represented by different grayscales and the numbers next to the genotype label are patient numbers carrying the respective genotype. For (SOC) treatment arm, the result from 182 patients, who are no-responder in phase B but completed phase C and with clinical samples, are shown in dark blue line.

We believe germline genetic polymorphisms also contribute to the various response to the same drug in different patients, even for the drugs failed to demonstrate efficacy in overall population. We were provided with a large number of whole blood samples that were collected from the above phase II clinical trials (CN162-006 and CN162-007), and these samples corresponded to 233 unique patients that had received DB104 and completed the trial adequately to measure their response to treatment. Thus, germline DNA samples extracted from blood of patients enrolled in these two trials were used to identify pharmacogenetic biomarker for DB104. For the discovery phase, 188 samples were selected, and the remaining 45 samples would be left for validating any potential SNPs using PCR. The discover and validation datasets were balanced for race and dose/trial number. In discovery phase, 188 samples from DB104 treatment group were genotyped using the Illumina 4.5 million whole genome SNP arrays. Two (2) out of the 188 samples failed QC and were excluded from the genome-wide analysis but added to the validation set. From this genome wide screen from 186 samples, we have identified SNP rs12217173 which has a p-value of $6.609 \times 10^{-8}$, which is very close to genome-wide significance cut-off of $5 \times 10^{-8}$, especially given the limited sample size of this study. FIG. 2. shows that patients carrying GG allele of 12217173 exhibited much better improvement on MADRS change from the baseline than patients carrying AA or AG genotype as well as patients receiving standard of care treatment (Duloxetine/escitalopram).

Figure 3:
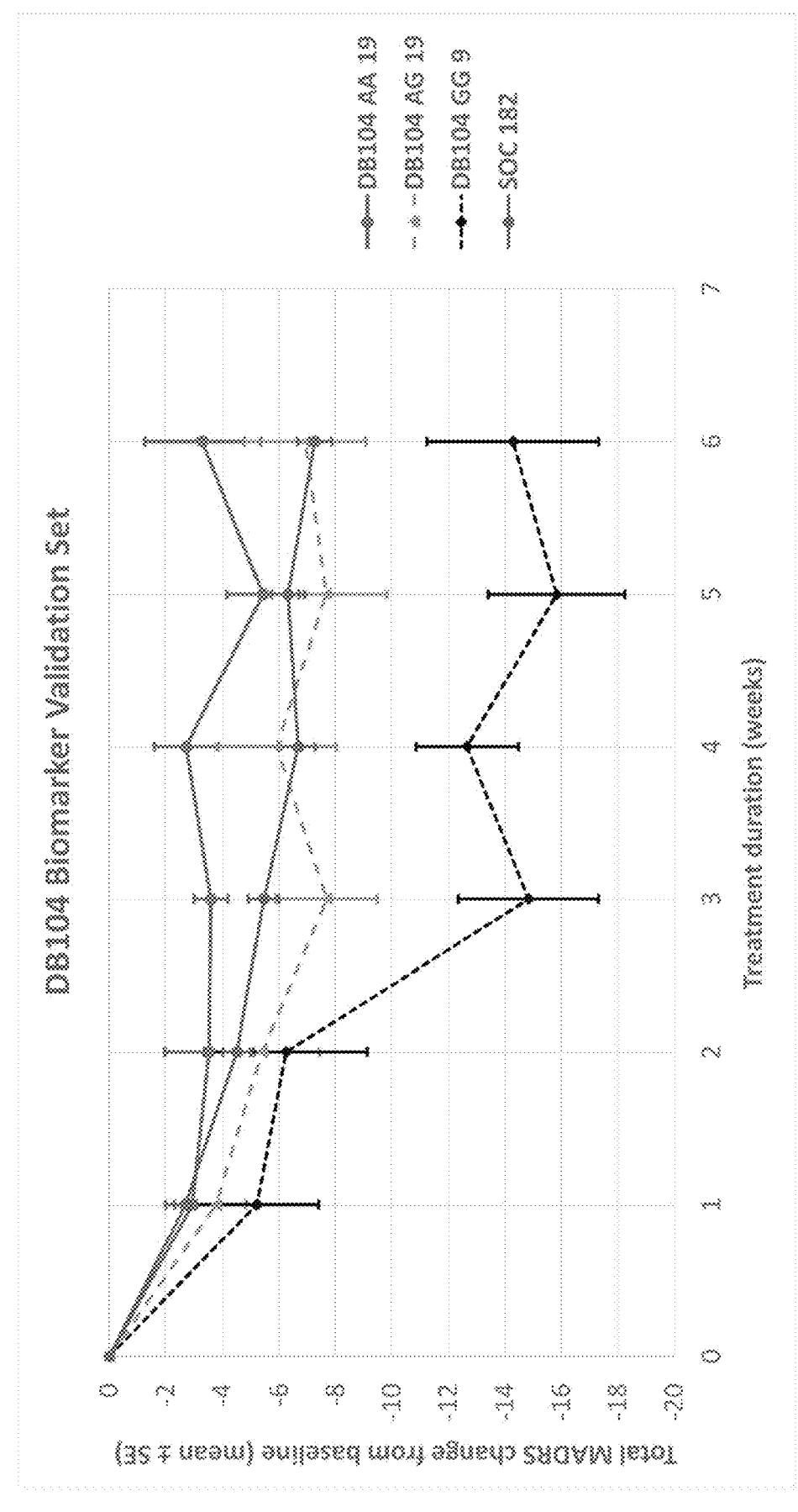
FIG. 3 illustrates exemplary correlation of rs12217173's genotypes with DB104 efficacy in the validation set. The mean change in MADRS total score for DB104 and SOC (duloxetine/escitalopram) treated patients is shown for weeks 1-6 post the baseline treatment, and the error bars represent the standard error of the mean. For DB104 treatment arm, 47 patients, who were not used in the genome wide scan, were used as validation set and their genotype-efficacy correlation results are shown here. For (SOC) treatment arm, the result from 182 patients, who are no-responder in phase B but completed phase C and with clinical samples, are shown in dark blue line.

To confirm the finding of rs12217173 as possible pharmacogenetic biomarker to predict DB104 efficacy, we next measured its genotype with Taqman SNP assay using the validation set which consists 47 patients, including two additional samples failed in genome-wide scan QC but passed real time PCR QC. FIG. 3 shows the result of validation dataset where patients carrying GG at rs12217173 had their MADRS score reduced to almost 16 points from the baseline comparing to patients carrying AA or AG genotype as well as patients receiving standard of care treatment (Duloxetine/escitalopram), who only experienced eight points or less MADRS score reduction. When we combined both discovery dataset and validation dataset together, patient carrying GG at rs12217173 still exhibited much improved MADRS score change comparing to patients carrying AA or AG genotype. Thus, patients with GG genotype were defined as the responders and patients carrying AA or AG genotype are defined as non-responders to DB104 treatment.

Figure 4:
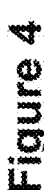
FIG. 4 illustrates exemplary correlation of rs12217173's genotypes with DB104 and SOC efficacy in combined dataset. The mean change in MADRS total score for DB104 and SOC (duloxetine/escitalopram) treated patients is shown for weeks 1-6 post the baseline treatment, and the error bars show the standard error of the mean. For DB104, all 233 patients that had available samples for genotyping are shown. For SOC, all 182 patients that failed to respond to SOC in trial phase B but were randomized to SOC in phase C and had samples available for genotyping are shown.

To examine whether rs12217173 is merely a prognostic biomarker for the disease instead of specific pharmacogenomic biomarker for DB104, DNA samples from 182 patients from the control group treated with duloxetine/escitalopram were genotyped using the Taqman SNP assays. FIG. 4 shows that there is no significant difference in MADRS score changes among patients carrying genotypes of rs12217173 when treated with SOC (duloxetine/escitalopram), as well as patients (non-responders) carrying AA and AG genotype in DB104 treated group. Therefore, rs12217173 associated improvement in MADRS is related to DB104 treatment, and rs12217173 appears to be a pharmacogenomics biomarker for predicting DB104's anti-depression activity, and thus it is named as DGM4 (Denovo Genomic Marker 4).

CN162006 is flexible-dose study where DB104 doses ranged from 0.5-2 mg/d, and CN162007 is a fixed dose, dose-response study where patients were treated with doses of DB104 at 0.25, 0.5, 1, or 2 mg/day. Due to the limitation on samples available for the genome-wide study, the analysis described in previous section was not treating patients taking different doses of DB104 differently. In order to refine our analysis, we have further evaluated the effect of DB104 dose in these two studies. In CN162006, the mean and median average dose per day is 1.5 mg, and 94% patients received doses of 1 to 2 mg per day. In CN162007 study, when we examined DB104 efficacy in patients carrying GG genotype at rs12217173, 1 mg and 2 mg group exhibited similar efficacy, and both are much better than 0.25 mg and 0.5 mg group. Thus, it is justifiable to pool patients in 006 and patients in 007 at 1 mg and 2 mg dose levels together, and as expected there is no significant differences between DB104 treatment group vs SOC treatment group at any time point (FIG. 7, Table 2A). However the patients carrying GG genotype at rs12217173 in DB104 treatment group exhibited statistical significance in MADRS total score reduction, MADRS Response Rate, and MADRS Remission Rate at week 5 and 6 compared to those of SOC treatment group (FIG. 8, Table 2B).

Figure 5:
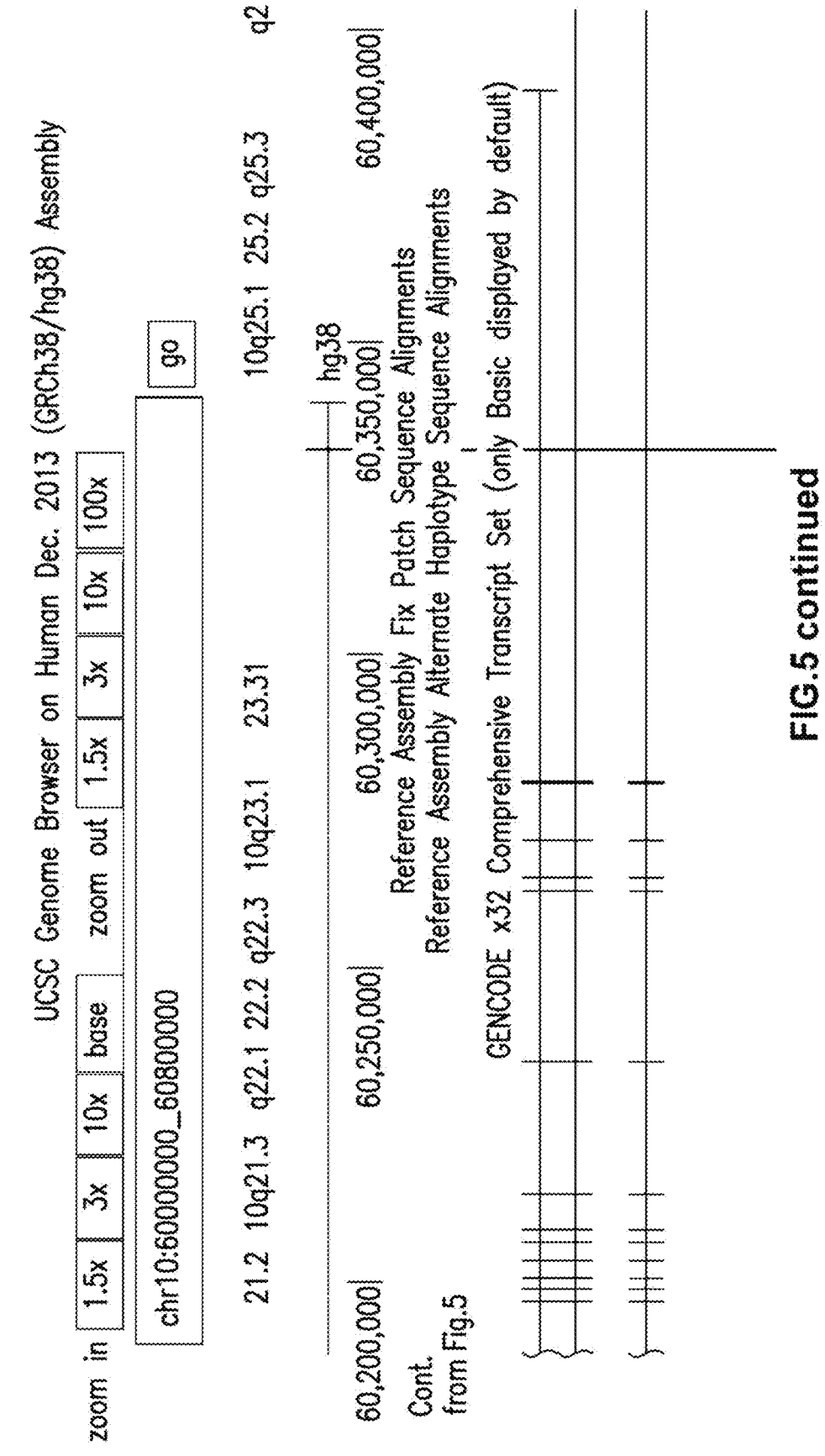
FIG. 5 shows that DGM4 (rs12217173) overlaps with ANK3 gene. DGM4 and its location, chr10:61,750,000-62,500,000, on human genome is shown by genome browser Chr10:61,750,000-62,500,000, and the vertical red line in the middle illustrates the DGM4 SNP position.
Figure 6:
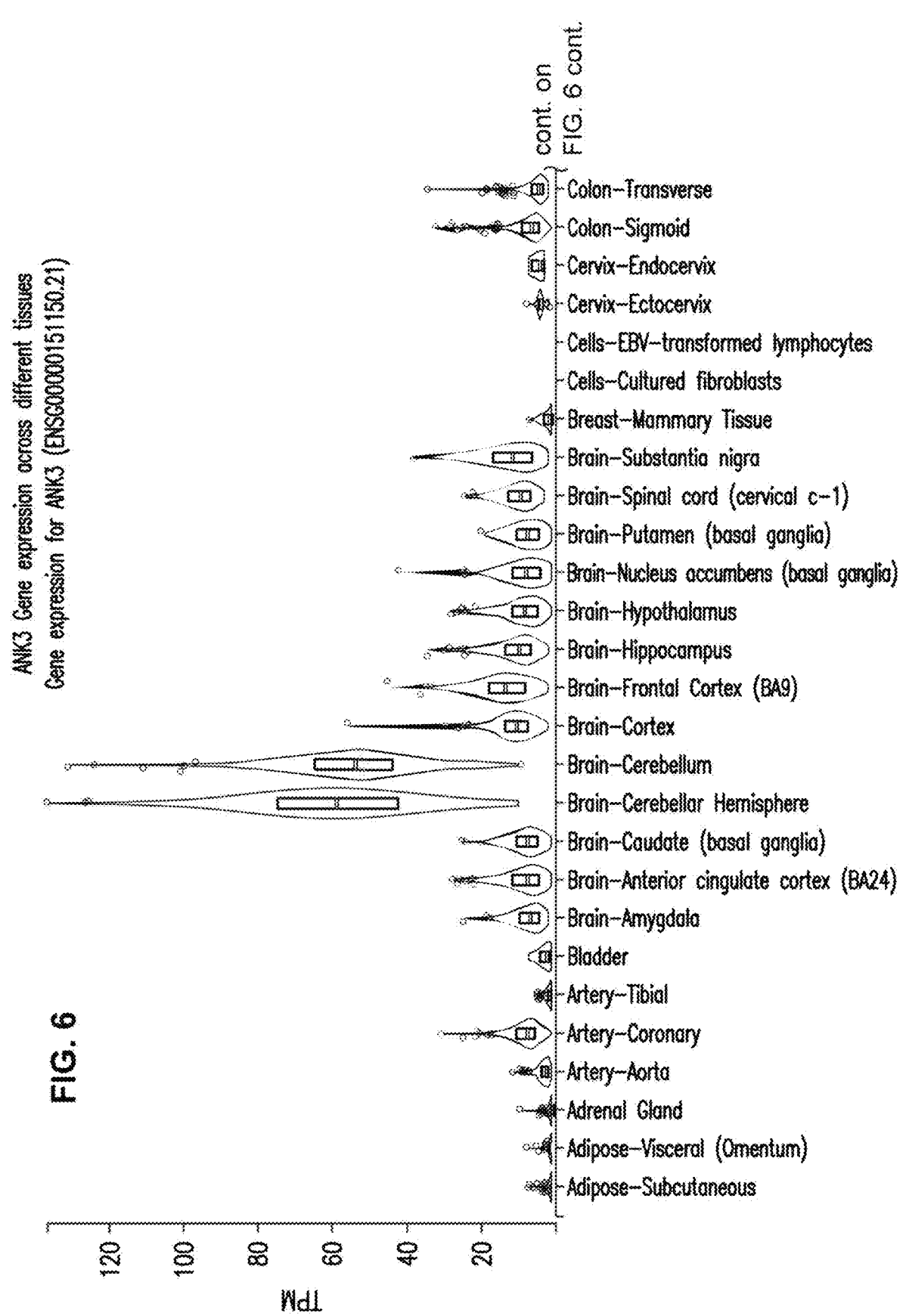
FIG. 6 shows ANK3 gene expression in 54 human tissues surveyed by the GTEx consortium, and that ANK3 is preferentially expressed in the cerebellum and cerebellar hemisphere regions of the brain.
Figure 6:
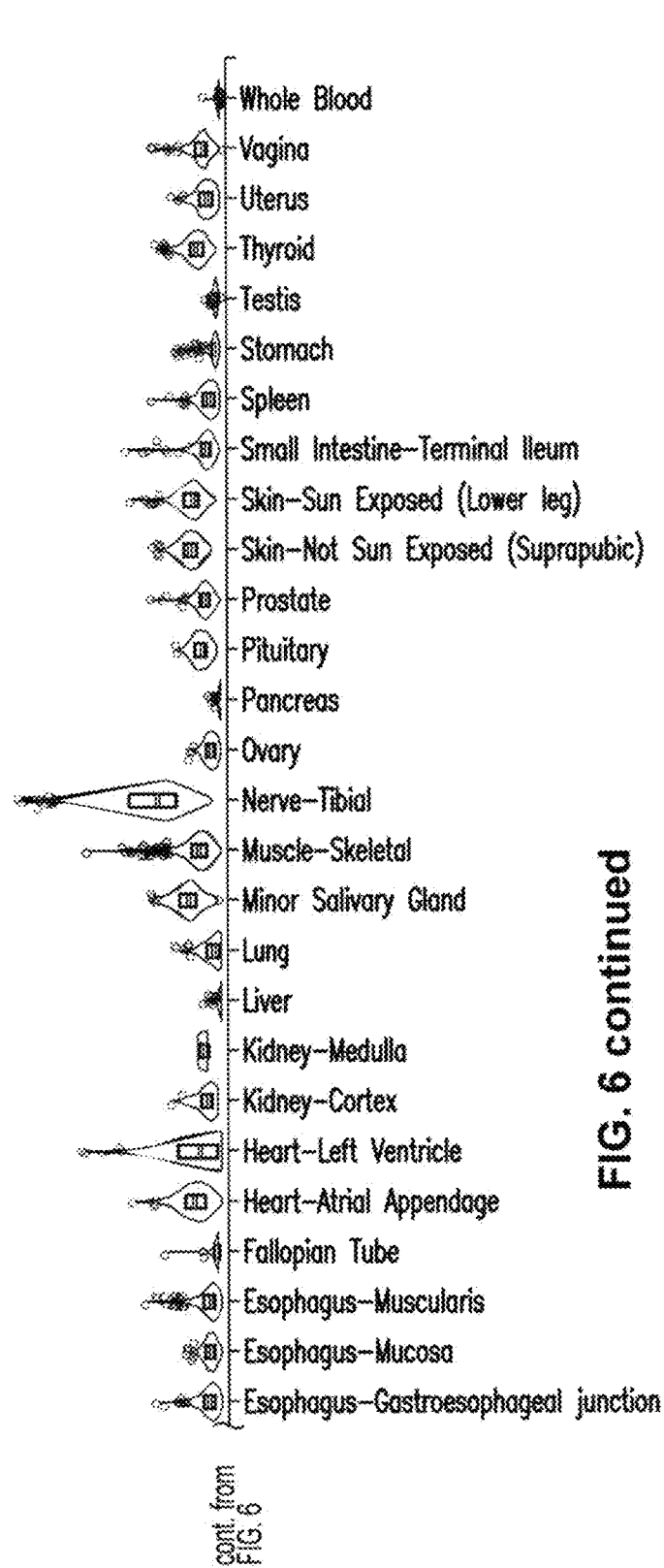

The prevalence of rs12217173 genotypes varies in different ethnic groups, and 17.8% of Chinese, 16.7% of Caucasian, and 20.5% of Japanese carries GG genotype, and only 1.7% African carries GG genotype (FIG. 9, Table 3A). Table 3B (FIG. 10) shows frequencies of rs12217173 genotypes varies in broader ethnic groups from 1000 Genomes project. Annotation of rs12217173 and its Potential Role in Depression Annotation of rs12217173 found it to be located at an intron of ANK3 (FIG. 5) and is most highly expressed in the brain (FIG. 6). Upon searching the EBI GWAS catalog, we identified that ANK3 has previous associations with many depression related traits; including eight associations with bipolar disorder and three associations with schizophrenia.

ANK3 functions as an adaptor protein in axon initial segments and regulates voltage-gated sodium channels (Kordeli et al. 1995; Poliak & Peles, 2003) and there are several lines of evidence linking it with depression and related diseases. In mouse studies of bipolar disorder, knocking down of ANK3 in the hippocampal dentate gyms through RNA interference reduced anxiety related symptoms and increased light phase activity; these affects were reversed upon treatment with the mood stabilizer lithium (Leussis et al. 2012). Similar effects were observed when an ANK3 +/−knockout was compared to the wild type; however, after chromic stress the ANK3 +/−mice transitioned to depression-related phenotype. Together the evidence suggests a gene-environment interaction between ANK3, stress and depression, which can be modified through pharmaceutical intervention. When studying C. elegans ANK3/unc-44 inactivating mutant, it was observed that ANK3 expression was necessary for the antidepressant mianserin to increase lifespan in conditions of oxidative stress (Rangaraju et al. 2016). In humans, ANK3 expression is lower in younger individuals than older; however, this effect is diminished in suicide completers, which have likely been exposed to extreme moods and stress (Rangaraju et al. 2016).

Because DB104 is a potent and selective inhibitor of the reuptake of the three monoamines; serotonin, norepinephrine and dopamine, which play critical roles in many other CNS disorders other than depression, the same genetic polymorphism, rs12217173, might be a potential pharmacogenetics biomarker for DB104 efficacy in treating other CNS diseases too.

A. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

B. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

The term "biomarker" or "marker" as used herein refers generally to a molecule, including a gene, protein, carbohydrate structure, or glycolipid, the expression of which in or on a mammalian tissue or cell or secreted can be detected by known methods (or methods disclosed herein) and is predictive or can be used to predict (or aid prediction) for a mammalian cell's or tissue's sensitivity to, and in some embodiments, to predict (or aid prediction) an individual's responsiveness to treatment regimens.

As used herein, a "pharmacogenomic biomarker" is an objective biomarker which correlates with a specific clinical drug response or susceptibility in a subject (see, e.g., McLeod et al., Eur. J. Cancer (1999) 35:1650-1652). It may be a biochemical biomarker, or a clinical sign or symptom. The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of DNA, RNA, or protein for specific disease markers in a subject, a drug or course of treatment may be selected that is optimized for the treatment of the specific disease likely to be present in the subject. Similarly, the presence or absence of a specific sequence mutation or polymorphism may correlate with drug response. The use of pharmacogenomic biomarkers therefore permits the application of the most appropriate treatment for each subject without having to administer the therapy.

As used herein, the term "polymorphic locus" refers to a region in a nucleic acid at which two or more alternative nucleotide sequences are observed in a significant number of nucleic acid samples from a population of individuals. A polymorphic locus may be a nucleotide sequence of two or more nucleotides, an inserted nucleotide or nucleotide sequence, a deleted nucleotide or nucleotide sequence, or a microsatellite, for example. A polymorphic locus that is two or more nucleotides in length may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. A polymorphic locus is often one nucleotide in length, which is referred to herein as a "single nucleotide polymorphism" or a "SNP." In some embodiments, the high-density genotyping may be conducted by using SNPs. In some embodiments, about 1,000-5,000,000 or more SNPs, may be used. In some embodiments, the high-density genotyping may be array-based. In some embodiments, the high-density genotyping may be conducted by using sequencing, such as high-throughput sequencing.

Where there are two, three, or four alternative nucleotide sequences at a polymorphic locus, each nucleotide sequence is referred to as a "polymorphic variant" or "nucleic acid variant." Where two polymorphic variants exist, for example, the polymorphic variant represented in a minority of samples from a population is sometimes referred to as a "minor allele" and the polymorphic variant that is more prevalently represented is sometimes referred to as a "major allele." Many organisms possess a copy of each chromosome (e.g., humans), and those individuals who possess two major alleles or two minor alleles are often referred to as being "homozygous" with respect to the polymorphism, and those individuals who possess one major allele and one minor allele are normally referred to as being "heterozygous" with respect to the polymorphism. Individuals who are homozygous with respect to one allele are sometimes predisposed to a different phenotype as compared to individuals who are heterozygous or homozygous with respect to another allele.

In genetic analysis that identifies one or more pharmacogenomic biomarkers, samples from individuals having different values in a relevant phenotype often are allelotyped and/or genotyped. The term "allelotype" as used herein refers to a process for determining the allele frequency for a polymorphic variant in pooled DNA samples from cases and controls. By pooling DNA from each group, an allele frequency for each locus in each group is calculated. These allele frequencies are then compared to one another.

A genotype or polymorphic variant may be expressed in terms of a "haplotype," which as used herein refers to a set of DNA variations, or polymorphisms, that tend to be inherited together. A haplotype can refer to a combination of alleles or to a set of SNPs found on the same chromosome. For example, two SNPs may exist within a gene where each SNP position includes a cytosine variation and an adenine variation. Certain individuals in a population may carry one allele (heterozygous) or two alleles (homozygous) having the gene with a cytosine at each SNP position. As the two cytosines corresponding to each SNP in the gene travel together on one or both alleles in these individuals, the individuals can be characterized as having a cytosine/cytosine haplotype with respect to the two SNPs in the gene.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "clinical sample" or "disease sample" and variations thereof refer to any sample obtained from a subject of interest that would be expected or is known to contain the cellular and/or molecular entity that is to be characterized.

The term "tissue or cell sample" refers to a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

"Plasma," or "blood plasma," as used herein, refers to the intravascular fluid part of extracellular fluid (all body fluid outside of cells). It is mostly water and contains dissolved proteins, glucose, clotting factors, mineral ions, hormones and carbon dioxide (plasma being the main medium for excretory product transportation). Blood plasma is prepared by spinning a tube of fresh blood containing an anticoagulant in a centrifuge until the blood cells fall to the bottom of the tube. The blood plasma is then poured or drawn off "Blood serum" is blood plasma without fibrinogen or the other clotting factors (i.e., whole blood minus both the cells and the clotting factors).

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "array" or "microarray", as used herein refers to an ordered arrangement of hybridizable array elements, such as polynucleotide probes (e.g., oligonucleotides), beads, or binding reagents (e.g., antibodies), on a substrate. The substrate can be a solid substrate, such as a glass or silica slide, a fiber optic binder, or a semi-solid substrate, such as nitrocellulose membrane. The nucleotide sequences can be DNA, RNA, or any permutations thereof.

As used herein, the term "phenotype" refers to a trait which can be compared between individuals, such as presence or absence of a condition, a visually observable difference in appearance between individuals, metabolic variations, physiological variations, variations in the function of biological molecules, and the like. A phenotype can be qualitative or quantitative. An example of a phenotype is responsiveness to a treatment, such as a drug.

"Responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5)

inhibition (i.e., reduction, slowing down or complete stopping) of disease spread; (6) relief, to some extent, of one or more symptoms associated with the disorder; (7) increase in the length of disease-free presentation following treatment; (8) decreased mortality at a given point of time following treatment; and/or (9) lack of adverse effects following treatment. Responsiveness can also be assessed using any endpoint indicating side effect and/or toxicity to the patient.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease.

The term "prediction" or "prognosis" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc.

As used herein, the term "output" refers to a value or score generated from a computer algorithm. The output may be generated based on assay results using the biomarkers disclosed herein as inputs to the computer algorithm. An "output" can be either quantitative or qualitative, and can be used for determining the likely responsiveness of a subject to a treatment in a companion diagnostic test.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

C. Biomarkers for Predicting DB104 Responsiveness

In some embodiment, the present disclosure describes novel genomic biomarkers that correlate with the activity of a triple reupdate inhibitor, such as DB104. These biomarkers can be used to identify the patients who are most likely to benefit or experience adverse effect from DB104 treatment.

Generally, an isolated SNP-containing nucleic acid molecule comprises one or more SNP positions disclosed by the present invention with flanking nucleotide sequences on either side of the SNP positions. A flanking sequence can include nucleotide residues that are naturally associated with the SNP site and/or heterologous nucleotide sequences. Preferably the flanking sequence is up to about 500, 300, 100, 60, 50, 30, 25, 20, 15, 10, 8, or 4 nucleotides (or any other length in-between) on either side of a SNP position, or as long as the full-length gene or entire protein-coding sequence (or any portion thereof such as an exon).

In one aspect, the biomarkers of the invention are those provided in Table 1 (Table 1A-1E) and others in linkage disequilibrium with them:

```
rs12217173 (SEQ ID NO: 51) Immediate Flanking
Sequence:
TTCTTTTTGTCGCGGTTTAAGCCCATTTTCTATTGTGCTAACCTCAGCAA

AAAAGGACATCAGCTAGTTACCATTCTCCTCATGATTAAAACTAATTAAG

[A/G]

CATCCTTCCATCTCTGTCATTAGAAGCACATGCAAATGGGCATGTTTCCT

TAATTTCTGATTCTAAATTGAGAAAAGTATAAAGAAGCAATTCTGGGCTT
```

In some embodiments, the invention includes individual biomarker and biomarker sets. In some embodiments, the invention also includes other biomarkers, e.g., SNPs, which have high correlation with the biomarkers, and they could also be used to predict DB104 responses by patients. For examples, those SNPs are in linkage disequilibrium with the SNPs provided in Table 1 (Table 1A-1E). Additional predicting SNPs might reside on genes related to the genes that SNPs listed in Table 1 (Table 1A-1E) are associated with. SNPs that are in linkage disequilibrium may be found in various public databases, e.g., HapMap.

In some embodiments, linkage disequilibrium (LD) refers to the co-inheritance of alleles (e.g., alternative nucleotides) at two or more different SNP sites at frequencies greater than would be expected from the separate frequencies of occurrence of each allele in a given population. The expected frequency of co-occurrence of two alleles that are inherited independently is the frequency of the first allele multiplied by the frequency of the second allele. Alleles that co-occur at expected frequencies are said to be in "linkage equilibrium". In contrast, LD refers to any non-random genetic association between allele(s) at two or more different SNP sites, which is generally due to the physical proximity of the two loci along a chromosome. See e.g., U.S. 2008/0299125.

In some embodiments, LD can occur when two or more SNPs sites are in close physical proximity to each other on a given chromosome and therefore alleles at these SNP sites will tend to remain unseparated for multiple generations with the consequence that a particular nucleotide (allele) at one SNP site will show a non-random association with a particular nucleotide (allele) at a different SNP site located nearby. Hence, genotyping one of the SNP sites will give almost the same information as genotyping the other SNP site that is in LD. See e.g., U.S. 2008/0299125.

In some embodiments, for diagnostic purposes, if a particular SNP site is found to be useful for diagnosing, then the skilled artisan would recognize that other SNP sites which are in LD with this SNP site would also be useful for diagnosing the condition. Various degrees of LD can be encountered between two or more SNPs with the result being that some SNPs are more closely associated (i.e., in stronger LD) than others. Furthermore, the physical distance over which LD extends along a chromosome differs between different regions of the genome, and therefore the degree of physical separation between two or more SNP sites necessary for LD to occur can differ between different regions of the genome. See e.g., U.S. 2008/0299125.

D. Applications of the Biomarkers

Information generated from genomic biomarkers described herein can be used to determine appropriate dosage and/or treatment regimens for an individual with CNS disorders such as depression. This knowledge, when applied to dosing or drug selection, can avoid adverse reactions or therapeutic failure and thus enhance therapeutic efficiency when administering a therapeutic composition, such as DB104.

The biomarkers disclosed herein and their associated SNPs or genes could also be used to predict patient's responses to treatment of other diseases or conditions besides major depressive disorder (MDD). These diseases include, but are not limited to, subtypes of MDD, e.g., major depression with psychotic features and depression with peri- or postpartum onset; post-traumatic stress disorder (PTSD), bipolar disorders, obsessive-compulsive disorder (OCD), eating disorders, attention-deficit hyperactivity disorder (ADHD), sleep disorders (including narcolepsy), substance use disorder, Tourette syndrome (TS), schizophrenia, epilepsy, migraine, autism spectrum disorders, Alzheimer's disease, Parkinson's disease, Huntington's disease, and other psychiatric and neurological disorders.

Pharmacogenomics involves tailoring a treatment for a subject according to the subject's genotype as a particular treatment regimen may exert a differential effect depending upon the subject's genotype. For example, based upon the outcome of a prognostic test, a clinician or physician may target pertinent information and preventative or therapeutic treatments to a subject who would be benefited by the information or treatment and avoid directing such information and treatments to a subject who would not be benefited (e.g., the treatment has no therapeutic effect and/or the subject experiences adverse side effects). Information generated from pharmacogenomic biomarkers using a method described herein can be used to determine appropriate dosage and treatment regimens for an individual. This knowledge, when applied to dosing or drug selection, can avoid adverse reactions or therapeutic failure and thus enhance therapeutic efficiency when administering a therapeutic composition. In some embodiments, the pharmacogenomic biomarker may be used to develop a companion diagnostic test.

Therefore, in a further aspect, provided herein is a companion diagnostic test using the biomarkers disclosed herein. For example, in one embodiment, a physician or clinician may consider applying knowledge obtained in biomarkers using a method described herein, when determining whether to administer a pharmaceutical composition to a subject. In another embodiment, a physician or clinician may consider applying such knowledge when determining the dosage, e.g., amount per treatment or frequency of treatments, of a treatment, administered to a patient.

The invention provides methods for assessing or aiding assessment of responsiveness of a subject to treatment. The invention also provides methods for predicting responsiveness or monitoring treatment/responsiveness to a treatment in a subject. The invention provides methods for selecting a subject for treatment and treating the subject. In some embodiments, the methods comprise assessing one or more pharmacogenomic biomarkers in a sample obtained from the subject; and predicting, assessing, or aiding assessment of responsiveness of the subject to a treatment based on the genotype of said one or more pharmacogenomic biomarkers.

The following is an example of a pharmacogenomic embodiment. A particular treatment regimen can exert a differential effect depending upon the subject's genotype. Where a candidate therapeutic exhibits a significant interaction with a major allele and a comparatively weak interaction with a minor allele (e.g., an order of magnitude or greater difference in the interaction), such a therapeutic typically would not be administered to a subject genotyped as being homozygous for the minor allele, and sometimes not administered to a subject genotyped as being heterozygous for the minor allele. In another example, where a candidate therapeutic is not significantly toxic when administered to subjects who are homozygous for a major allele but is comparatively toxic when administered to subjects heterozygous or homozygous for a minor allele, the candidate therapeutic is not typically administered to subjects who are genotyped as being heterozygous or homozygous with respect to the minor allele.

The methods described herein are applicable to pharmacogenomic methods for preventing, alleviating or treating conditions such as CNS diseases, metabolic disorders, cardiovascular diseases, cancers, etc. For example, a nucleic acid sample from an individual may be subjected to a prognostic test described herein.

In certain embodiments, a treatment regimen is specifically prescribed and/or administered to individuals who will most benefit from it based upon their likelihood of responding to a treatment regimen assessed by the methods described herein. Thus, provided are methods for identifying a subject with a high likelihood of responding to a treatment regimen and then prescribing such treatment regimen to individuals identified as having a high likelihood of responding. Thus, certain embodiments are directed to a method for treating a subject, which comprises: detecting the presence or absence of a pharmacogenomic biomarker associated with responsiveness to a treatment regimen in a nucleotide sequence set forth herein in a nucleic acid sample from a subject, and prescribing or administering the treatment regimen to a subject from whom the sample originated where the presence of a pharmacogenomic biomarker associated with responsiveness to the treatment regimen is detected in the nucleotide sequence.

The treatment sometimes is preventative (e.g., is prescribed or administered to reduce the probability that a disease condition arises or progresses), sometimes is therapeutic, and sometimes delays, alleviates or halts the progression of a disease condition. Any known preventative or therapeutic treatment for alleviating or preventing the occurrence of a disorder may be prescribed and/or administered.

Pharmacogenomics methods also may be used to analyze and predict a response to a drug. For example, if pharmacogenomics analysis indicates a likelihood that an individual will respond positively to a treatment with a particular drug, the drug may be administered to the individual. Conversely, if the analysis indicates that an individual is likely to respond negatively to treatment with a particular drug, an alternative course of treatment may be prescribed. The response to a therapeutic treatment can be predicted in a background study in which subjects in any of the following populations are genotyped: a population that responds favorably to a treatment regimen, a population that does not respond significantly to a treatment regimen, and a population that responds adversely to a treatment regiment (e.g., exhibits one or more side effects). These populations are provided as examples and other populations and subpopulations may be analyzed. Based upon the results of these analyses, a subject is genotyped to predict whether he or she will respond favorably to a treatment regimen, not respond significantly to a treatment regimen, or respond adversely to a treatment regimen.

The comparisons and/or calculations for predicting, assessing or aiding assessment can be carried out in any convenient manner appropriate to the type of measured value and/or reference value for the pharmacogenomic biomarkers at issue. The process of comparing or calculating may be manual or it may be automatic (such as by a machine including computer-based machine). As will be apparent to those of skill in the art, replicate genotyping may be taken for the pharmacogenomic biomarkers.

Also provided herein is a method of prognosticating responsiveness of a subject to a treatment using the companion diagnostic test disclosed herein. The tests described herein also are applicable to clinical drug trials. In some embodiments, the pharmacogenomic biomarkers can be used to stratify or select a subject population for a clinical trial. The pharmacogenomic biomarkers can, in some embodiments, be used to stratify individuals that may exhibit a toxic response to a treatment from those that will not. In other embodiments, the pharmacogenomic biomarkers can be used to separate those that will be non-responders from those who will be responders. The pharmacogenomic biomarkers described herein can be used in pharmacogenomic-based design and in managing the conduct of a clinical trial.

Thus, another embodiment is a method of selecting an individual for inclusion in a clinical trial of a treatment or drug comprising the steps of: (a) obtaining a nucleic acid sample from an individual; (b) determining the identity of a polymorphic variation which is associated with a positive response to the treatment or the drug, or at least one polymorphic variation which is associated with a negative response to the treatment or the drug in the nucleic acid sample, and (c) including the individual in the clinical trial if the nucleic acid sample contains said polymorphic variation associated with a positive response to the treatment or the drug or if the nucleic acid sample lacks said polymorphic variation associated with a negative response to the treatment or the drug. In addition, the methods described herein for selecting an individual for inclusion in a clinical trial of a treatment or drug encompass methods with any further limitation described in this disclosure, or those following, specified alone or in any combination. The including step (c) optionally comprises administering the drug or the treatment to the individual if the nucleic acid sample contains the polymorphic variation associated with a positive response to the treatment or the drug and the nucleic acid sample lacks said biallelic marker associated with a negative response to the treatment or the drug.

E. Additional Biomarkers or Drug Targets

Also provided is a method for identifying polymorphic variants proximal to the biomarkers disclosed herein. In some embodiments, the proximal polymorphic variant identified sometimes is a publicly disclosed polymorphic variant, which for example, sometimes is published in a publicly available database. In other embodiments, the polymorphic variant identified is not publicly disclosed and is discovered using a known method, including, but not limited to, sequencing a region surrounding the identified pharmacogenomic biomarker in a group of nucleic samples. Thus, multiple polymorphic variants proximal to a biomarker are identified using this method.

The proximal polymorphic variant often is identified in a region surrounding the biomarker. In certain embodiments, this surrounding region is about 50 kb flanking the biomarker (e.g., about 50 kb 5' of the first polymorphic variant and about 50 kb 3' of the first polymorphic variant), and the region sometimes is composed of shorter flanking sequences, such as flanking sequences of about 40 kb, about 30 kb, about 25 kb, about 20 kb, about 15 kb, about 10 kb, about 7 kb, about 5 kb, or about 2 kb 5' and 3' of the biomarker. In other embodiments, the region is composed of longer flanking sequences, such as flanking sequences of about 75 kb, about 150 kb, about 300 kb, about 600 kb, about 1,200 kb, about 2,000 kb, about 4,000 kb, about, or about 10,000 kb 5' and 3' of the biomarker (ref).

In certain embodiments, polymorphic variants are identified iteratively. For example, a first proximal polymorphic variant is identified using the methods described above and then another polymorphic variant proximal to the first proximal polymorphic variant is identified (e.g., publicly disclosed or discovered) and the presence or absence of an association of one or more other polymorphic variants proximal to the first proximal polymorphic variant is determined.

The methods described herein are useful for identifying or discovering additional polymorphic variants that may be used to further characterize a gene, region or loci associated with a condition, a disease, or a disorder. For example, allelotyping or genotyping data from the additional polymorphic variants may be used to identify a functional mutation or a region of linkage disequilibrium. In certain embodiments, polymorphic variants identified or discovered within a region comprising the biomarker are genotyped, and it can be determined whether those polymorphic variants are in linkage disequilibrium with the biomarker. The size of the region in linkage disequilibrium with the biomarker also can be assessed using these genotyping methods. Thus, provided herein are methods for determining whether a polymorphic variant is in linkage disequilibrium with a biomarker, and such information can be used in prognosis/diagnosis methods described herein.

Additionally, genes may be identified that are in proximity to the biomarkers, and their functions analyzed. Genes with functions that are directly or indirectly related to the relevant phenotype, or other genes in the same cellular pathway, may be targets for further analysis with the relevant phenotype, and new biomarkers may be identified.

Further provided herein is a method of developing novel therapeutic agents and/or identifying a novel drug target using the biomarkers disclosed herein. In some embodiments, the biomarkers and their associated SNPs or genes could gain insight of the underlying biological pathways or mechanisms underlying the studied phenotypes, such as efficacy, adverse effect, or other endpoints.

F. Reagents and Kits

The present invention contemplates the preparation of kits, chips, devices, or assays for use in accordance with the present invention. Such an assay, chip, device, or a kit may comprise a plurality of primers or probes to detect genetic signature of SNPs such the ones listed in Table1. Such methods can include instruments and instructions that a subject can use to obtain a sample, e.g., of buccal cells or blood, without the aid of a health care provider.

The invention also contemplates the development of computer algorithm which will convert the test results generated from the measurement of the genomic biomarkers into a score , which will be used to determine in whether an individual should receive the therapeutic invention, such as DB104 treatment.

Diagnostic kits based on the biomarkers described above might be developed, and they can be used to predict individual's response to the corresponding drug. Such test kits can include devices and instructions that a subject can use to obtain a sample, e.g., of buccal cells or blood, without the aid of a health care provider.

For use in the applications described or suggested above, kits or articles of manufacture are also provided by the invention. Such kits may comprise at least one reagent specific for genotyping a biomarker described herein, and may further include instructions for carrying out a method described herein.

In some embodiments, the invention provides compositions and kits comprising primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of polynucleotides in a sample and as a means for detecting cell expressing proteins encoded by the polynucleotides. As will be understood by the skilled artisan, a great many different primers and probes may be prepared based on the sequences provided herein and used effectively to amplify, clone and/or determine the presence and/or levels of genomic DNAs.

In some embodiments, the kit may comprise reagents for detecting presence of polypeptides. Such reagents may be antibodies or other binding molecules that specifically bind to a polypeptide. In some embodiments, such antibodies or binding molecules may be capable of distinguishing a structural variation to the polypeptide as a result of polymorphism, and thus may be used for genotyping. The antibodies or binding molecules may be labeled with a detectable marker, such as, for example, a radioisotope, fluorescent compound, bioluminescent compound, a chemiluminescent compound, metal chelator or enzyme. Other reagents for performing binding assays, such as ELISA, may be included in the kit.

In some embodiments, the kits comprise reagents for genotyping at least one, at least two, at least three, at least five, at least ten, or more biomarkers. In some embodiments, the kits may further comprise a surface or substrate (such as a microarray) for capture probes for detecting of amplified nucleic acids.

The kits may further comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a polynucleotide specific for a biomarker. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application and may also indicate directions for either in vivo or in vitro use, such as those described above.

The kit can further comprise a set of instructions and materials for preparing a tissue or cell sample and preparing nucleic acids (such as genomic DNA) from the sample.

The invention provides a variety of compositions suitable for use in performing methods of the invention, which may be used in kits. For example, the invention provides surfaces, such as arrays that can be used in such methods. In some embodiments, an array of the invention comprises individual or collections of nucleic acid molecules useful for detecting pharmacogenomic biomarkers of the invention. For instance, an array of the invention may comprises a series of discretely placed individual nucleic acid oligonucleotides or sets of nucleic acid oligonucleotide combinations that are hybridizable to a sample comprising target nucleic acids, whereby such hybridization is indicative of genotypes of the pharmacogenomic biomarkers of the invention.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into nucleic acid molecules that are synthesized. The synthesized product is then contacted with a solid substrate, such as a glass slide, which is coated with an aldehyde or another reactive group which will form a covalent link with the reactive group that is on the amplified product and become covalently attached to the glass slide. Other methods, such as those using amino propryl silica surface chemistry are also known in the art, as disclosed at world wide web at cmt-.corning.com and cmgm.stanford.edu/pbrown1.

Attachment of groups to oligonucleotides which could be later converted to reactive groups is also possible using methods known in the art. Any attachment to nucleotides of oligonucleotides will become part of oligonucleotide, which could then be attached to the solid surface of the microarray. Amplified nucleic acids can be further modified, such as through cleavage into fragments or by attachment of detectable labels, prior to or following attachment to the solid substrate, as required and/or permitted by the techniques used.

---

SNP Sequence ID:

--- rs12219340 SEQ ID NO: 1 chr10:62092193
AAAATAGGACACAATTTCTTTTTAGAAGCTCACCTCATATCAAGTACATATTCTAATGCAAAGTATGAA
TTTCACAAAGGGCTGAGTATGTAGGTGTTGG
C > T
GCCACTGTTCTGATGTTAGCACCCAGCACTTATTTTTCTAACTTTTAGAAAAATGTTTACTAATTTCTG
CCAGTTGCACCCCTTTGTAGTCACCTCCCAG rs4612751 SEQ ID NO: 2 chr10:62092917
TTTAATCTTTTTATTTTGATAAAGAACTATAAAATGGGACATATGGATATACATCTAAAGTCTCCAAATT
TCCATAGTGTGTTTTTTGAGCATCTTTTTA
T > G
TATTATTATACTTTAAGTTCTGAGATACATGTGCAGAATGTGCAGGTTGTTACATAGGTATACACGTG
TCATGGTGGTTTGCTGCACCCATCAACCCGTC rs10994306 SEQ ID NO: 3 chr10:62097576
GTAGGTGCTAAGGCATACCACAAATGAATAAAGCAAGATATTCCCTGACTTCACAGTTTTATAAACAT
AGGTTAACAAGTAATTCTTATTACTCACACAT
C > T
CTGGTGAGTGCTATAGTAGAAAAATATATTATTGGAGTACCATATTAGGAAAAAGCATTTTGTATATG
ACTGGCCAGTGAAGAAGCATTGAATTTATCCC rs7083556 SEQ ID NO: 4 chr10:62121387
TTGAAAATATTTCATCAATGTATTATTCCACTTGTATTTCATATAGTTCAGTCACTTTATTCAGTAAGAA
AGGAACTGGCAGGAGTTTGTAGTCAGGGAT
A > T
TCATTCATTGTAGTGGAACAAGGTATGGGGGAAGTGGAAGAGATGTAGTCCAAGAAATATTCTGAGG
ATTATTATTTACAATATATTCCTAGTTATAGTT rs12572120 SEQ ID NO: 5 chr10:62088304
TTAAATAAAAGGATTATATCTCTATGGTGGAATGTACTGCAGGCATTAAATCAATGTTTATGTACCTCT
ACACAAATAAACTAGAAAATCTAGAAGAAAT
G > T
GATAAATTCCTGGACACATACACCCTCCCAAGACTAAACCAGGAAGAAGTCCAATCCCTGAATGGAC
CAATAACAAGTTCTGAAATTGAGGCAGTAATTA rs10821741 SEQ ID NO: 6 chr10:62115503
ACCATGAAGTGCTCGCTCACCTCCACGGTCATAGTGCAATATTCCTTTGTTTGTCGATTATAAGGTG
CACTTCAAACCTTCCCCAACATCTCCCTCCAGG
C > G
TCCTTTTCTTAATGTGCCTACAATTAGTCAGTCGTATTTTGCCACCTCACAACTTTAAACAAAGTTCTA
CATTTCAGACACAAGTGGAAAAATGAGGCCA rs35050621 SEQ ID NO: 7 chr10:62098778
TGTCTCCAAATAAATAGGAGCCGTATTTGGGTCTGGAAGCCATGAAGTCTTGGGGAGAGCTTCACA
GATGTTTGGTGGGTTTCCAAAGACAATTAGCATA
- > A
TACTCCAAGAGTGGAGTGAAATAGAATGTGTGCTTGTTTCTTTTCTTTGTTAGTACCAAAATAGATTT
GTGTTTATTTGATAGAAAAAAAAAATTCTAGC
* deletion/insertion variation -continued

| SNP Sequence ID: |
| --- | rs10821738 SEQ ID NO: 8 chr10:62109449
AGAGACTCAAAATAACTCAAATTCTTTGGCTACGAATAACTCTATTTATCTGCAAAAAGCCACATGAA
CCCTAATTCTTTCTAAGCACAAAGAAACAGAG
G > A
AGAGGATATATAAATAGTAGCAATCATTGGAACAAAAGTTGAAATGAGGGTAGAAATAGAGACTCCC
ACCCTCTGTTCTCCCTTCTAATAGGCACAAATA rs10821739 SEQ ID NO: 9 chr10:62109643
ACAAATATTCATGGAAGAATAAGAAACTTCAGAGCAACATGGGTCTCTGGACAAGTCATAATTTTTAG
AAGTGAGTGGAGACTTAGAGGGAACAGTAAGA
C > T
AAGAAAATAGCAGGGAAAGACCATAAAGTAACGGACTTGTCTAGTTAATAAGCATTTTCCTGGAAAT
GAATGGAATAGGATACAATGGTGAGAATACACA rs10821740 SEQ ID NO: 10 chr10:62113686
CAATTCTCTTAGGATTCCCCAGGGAGATCCCAGCCTGTTAATTTTCCCCAGTAGTTGTCAGCAGGCA
GGGCCAGCAGAGCTACGTGCATTGTTATCAGCT
C > T
AGCCTGTGACCAGGCACGAAATGGCTGTGCTTGGCTTGCGCATCTCCATATCCACGTGCAGTCCAT
GATGTCATGGAGGCCGTGTTGCCTCCTGCACAGC rs12775352 SEQ ID NO: 11 chr10:62085590
AAGACCTAAAGCAGAAACATCATTTGACCCAGCAATCCCATTACTGGGTATATACCCAAAGGAGTAT
AAATCATCCTTTiATAAAGACACATGCACACAT
A > C
CGTTCTTTGCAGCACCAGTCACAATAACAAAGACATGGAATCAACCTAAATGCCCATCAATGATAGA
CCGAATAAAGAAAATGTGGTACATATACACCAT rs10994312 SEQ ID NO: 12 chr10:62122704
AACCAGGTGGATTCACAGAGAAAAACTCTGTCTGAGGAATTTGGGAAAGGCTTTACCCGGGGACAT
TAGAGCTGGTCCTGGAGAGTAGATAGGGTGGGCT
A > C
TCCTGGACATAGATGACTTGTTCTCTGTTCATCCATTGGATATTCCCAAGCCGTTTTCTTTTGCTACC
CTTTCCAGCAGAAATGCCAACTACTTACTTTT rs10994313 SEQ ID NO: 13 chr10:62122781
CTGGAGAGTAGATAGGGTGGGCTATCCTGGACATAGATGACTTGTTCTCTGTTCATCCATTGGATAT
TCCCAAGCCGTTTTCTTTTGCTACCCTTTCCAG
C > G
AGAAATGCCAACTACTTACTTTTCCAGTCTCCCTTGCAGCTGGGGTTGCGGCGGGCGGGCGGGGG
AGGGGGGCGGGGGGCGCAATACAACATGCAGTTCT rs12781371 SEQ ID NO: 14 chr10:62085918
AAGTGGGAGCTAAATAAAGAGAACACAIAGGCACAGAGAGGGGAACAACAGACACTGGGGCCTTTT
GGAGGGTGGAGGGTGGGAGGAGAGAGAGGATCTG
G > C
AAAAACCACCAATGGGTACTAGGTTTAATACCTGGGTGATGAAATAATCTGTATAACAAACCCCCATG
ACACAAGTTTACATATATAACACACCTGCACG rs7902423 SEQ ID NO: 15 chr10:62123689
GCATATAATGTCCTTTCTAAATCCCTTTTCTTATAGAAAAACATCGTAAGTTTTTATAAAAAGATAGGA
TTAATTTATTTTTAAGCTAACAACAAAGGTG
T > C
TACCAGCCCACTGTAGTTAAAAAAGAGGAAGGAGAAGTGTTTTTTTTTTTTTTTTTTTTTTTTTTAACTTTA
AGAGAAAACAGGCCGGGCTCAGTGGCTCAA rs7917429 SEQ ID NO: 16 chr10:62123720
TATAGAAAAACATCGTAAGTTTTTATAAAAAGATAGGATTAATTTATTTTTAAGCTAACAACAAAGGTG
TTACCAGCCCACTGTAGTTAAAAAAGAGGAA
G > A
GAGAAGTGTTTTTTTTTTTTTTTTTTTTTTTTAACTTTAAGAGAAAACAGGCCGGGCTCAGTGGCTCAA
GCCTGTAATCCCAGCACTTTCGGAGGCTGAG rs7917540 SEQ ID NO:17 chr10:62123774
CTAACAACAAAGGTGTTACCAGCCCACTGTAGTTAAAAAAGAGGAAGGAGAAGTGTTTTTTTTTTTTT
TTTTTTTTTTAACTTTAAGAGAAAACAGGCC
G > A
GGCTCAGTGGCTCAAGCCTGTAATCCCAGCACTTTCGGAGGCTGAGGCGGGCAGATCACTGAAGG
TCAGGAGTTCCTGACCAGCCTGGCCAACATGGTGA rs10994319 SEQ ID NO: 18 chr10:62130265
ATTTTTTAAAAATCGCTATGAATAGCATTGAAAAATTAATTTAAAAAGAAAAAATATATAAAAATCACTA
TTCAAATATTGCTCTCAAAGTAGAAGAATG
C > T
ATTAAAACATGACACTGTTTTGAAGGCCCTATCATGAATCCAACAAATACTTACAGCGCAGTAAATGG
GAGAACACAATTATAACATCACAGTTCTTATC -continued

---

| SNP Sequence ID: |
| --- |

--- rs1824405 SEQ ID NO:19 chr10:62130662
TCAGCATTTGTGAGCTAGCTCTGAAAACTCAAGCTAAACATCAACCTGAGATAACATTTCTTACTTTG
CAAACATACTGTTAATAGTTGAAAGTAATAGG
G > A
GAAATCGGGAGGAAAGGAGGGGGCATAACCTAAATAAGTGGAAACCAATCCCTGTGCATTCCATTC
TCAATACAAGGTATCACCACATATTGGTTACAGA rs1010556 SEQ ID NO: 20 chr10:62133503
TCACAGATGGAAGGCAAGGTCACGGAAGGCAAGCAAGGCTGAGATGGTTTTAGAGACAGGTGGCA
TGGAGGATCTCTCCCTTGCTTTACAATTTGCCCCA
C > T
CACACTCCATGAATTCTAATATGCTCTTGGAGTGAGGGATATAGCCGTCCTTGTTCTAGCACTGAAA
GTGGAATCCTGGGAAACCTTTCAGTCCTGGGCA rs10994326 SEQ ID NO: 21 chr10:62158385
ATACCCATGAAAATTTGTCCTCTGGATTTGAACATGATCACTGACATTTCAGTGATGGAAAAACGTAT
GTTGCTATGTACATTTTCTATACCATGTCCAC
A > G
CAGATAACGTTTCTTTAATTCACTCATTTAACAAATATTTATTGGGTACCTTCTTTAATGAAGCAGCAT
AATCCAAACATTATTTAAGACACCCAAACTC rs10821747 SEQ ID NO: 22 chr10:62152721
TGGTTGCAGTGAGCTGAGATCACACCACTGCACTCCAGTCTGGGTGACAGAGCAAGGCTCTGTCCC
TTGGCTCCCCACTCCCTCCCCCAAAAAAGAAAAA
A > G
AAAGCTAAGGACAAAAATTCTTAAGTGACTTCCCTTTCTCAAGAAAAAAAGAAAAAATCTGTTCTTGTT
TTATAAAAGTCCCAGGTACAAGAATTCCTAA rs12764333 SEQ ID NO: 23 chr10:62175060
GTCTGGCCTGGAGCTACTGAAAATCCTGCCTACAAGGACTTGTGGAAGGAGCATCATGCCTCCGTT
ATTCCCAGAGGCCGAGGGAGGAAAATGAGCAGAC
C > T
AGCCTGTGTTTTTGGAAGGAAACTCCTAAAAACTACAATCATTCAGAGGCAGCCTGGATCATCTGCA
AAACGTAAAAAGAACCTTTAAATTCCTCTTAAA rs1459729 SEQ ID NO: 24 chr10:62122754
CTTTACCCGGGGACATTAGAGCTGGTCCTGGAGAGTAGATAGGGTGGGCTATCCTGGACATAGATG
ACTTGTTCTCTGTTCATCCATTGGATATTCCCAA
G > A
CCGTTTTCTTTTGCTACCCTTTCCAGCAGAAATGCCAACTACTTACTTTTCCAGTCTCCCTTGCAGCT
GGGGTTGCGGCGGGCGGGCGGGGGAGGGGGGC rs10994331 SEQ ID NO: 25 chr10:62171445
CCTCTGTGCCCCTCTCACCAACCCTGTAGAAGTAGGAATAGAAATGAATTAAGCAGCACCACAGTGG
ACTAGAGAAGGGCCCAGACTCCAGGACCAGACT
G > T
CCTGGATATGAATCCCAGCATGGTCACTTACTAGGAAAATAACCTTAGATAAGTGACCCCATCTGCC
TGTGCCTCAGTTTCCACATTTCTAAAGTGTAGA rs10994332 SEQ ID NO: 26 chr10:62171600
GACCCCATCTGCCTGTGCCTCAGTTTCCACATTTCTAAAGTGTAGAAATGAGGATATAGAAGAAAGT
ACTCATGAGATTTTGAAATGAAAGAGTATTTAT
A > G
AAGTGCTTAATCCAGTAAGTACTATATAAAAATAAGGAGTCAAATTTAAAAAAATTAGAAGACAGCCA
GGGCAATTAATCCCAGCTGCATACTGCCTAGT rs7100501 SEQ ID NO: 27 chr10:62170830
CCTCTCCCATCCAATCTTTATCCCTCTCCTTCCTTTTTCTTCTCCTGGCTTTTGACCCAGCTACCAAG
GATCCACTGGGGGAACTCCAAGGAACTGGTGG
A > G
TAATGGAGCCCCAAGCTGGAAGGCGCTTGGTTTCCAAATAACTGCAGCCTCTACACCAAGCCACATT
GGACTGTGACGTGAACCAGAAACAAACTTTTAT rs3851251 SEQ ID NO: 28 chr10:62130429
AATGGGAGAACACAATTATAACATCACAGTTCTTATCACAAAGATTGCCATAGTCTAGATCTGAGAAG
GCTTTTAATTAGTATTTCTAACATTTATCATG
C > T
CCAGTGAATGACAGCTTAGACAAAAATCAGTGGCTTCAACACTTCTCAAAATTATTCAGTAATTATTC
TCCAGGTTTCTAATTCATCAGCTTGGTAGATT rs7072841 SEQ ID NO: 29 chr10:62131838
GTGAGGCATAAGGTAATGGGAAATACTACAATGGAAAACACAGACGATAGAATATTAGAGGGAAAAA
GCTTTCACATCTTTATAATTCTACACTTTACCG
C > T
TGTTTATAAATGTTGCAGTATATCCACAAATCAGTTAAATTCATATATTTCAAAGCCAACCAAGAGATA
AAACTAAAAGTTAAAGAGGAAGAAAAAAATT -continued

| SNP Sequence ID: |
| --- | rs1459728 SEQ ID NO: 30 chr10:62132129
TTACCAATTGTGGCAACAACTGTGGATGTACTACATCAATATATTATGATCTAGACAATCCACACATG
AAATAGTGTCAATTCTAGTTATCTCATGATGG
C > T
TAAGAGAGGATTTAAGGGGTATCACGATTCTCTGTCTTATGAAGACCAGCTAAAGAAACAGGGAGCG
TTTAACTTGAAGAGAAGCAGCAGCACCAACATA rs1380455 SEQ ID NO: 31 chr10:62132820
ATAAAAATAGAGGCATGATCAGTAGATTTTTTTAAAACCAGTATTTATTGTAAAGCAATTTGAAATCAT
GTTTGTCATCTCCATCATATGAATTTGAGTA
A > C
AAAGTGATCCTCTTGCACATGCAATATTTTAGTTACATAACTTTGTAGCATCCCCCATCATTTTCTAAT
AAAACAATGGTGGGCTTTCTCTGACTGGGAC rs1380454 SEQ ID NO: 32 chr10:62133051
AAGTAGTAATGTTCTTTATGTCTATTTATGTCCAATATCTCATCGGGTAGAAGGTGGCCAGGCCAGG
GGCCTCTTGTGTGGGGAGAAGATTTAAATGTCC
G > A
TCCCTTGGCTAAGGCAGTATAGGCAGGGGAAAGTCAAAGTTGGAAATAATCAAAATAAGAATGCAAA
TGAATAAGAAACAAGATCCTGGGAGTTGAAGAG rs10821744 SEQ ID NO: 33 chr10:62127894
TTTCATTGTATACTCCACGTGTTGCAATAATGAAATACAAGTAGCCCTGTATCCTAGAATTGTGTATCT
CACTGCATTGTTCAGTTTATTACAACCTTGC
C > T
TCTGAAATTTATTTATCAAGAAGAGCACATTAACTAAAAGAAGGGAAGAGAAAATCTCTAGGGGCAAT
ACATGATGCTATACACTAGTGCATGTACACAC rs4147263 SEQ ID NO: 34 chr10:62137665
TTTCTAAGCCTTGATTTCCTCATCAGCAAAATGCGAATAATGTCACCTTACTCAGAGGGTTCATTTAA
CTGTTATGTGAGACAACAATGTTTGACACCTA
C > T
CAATTATTTTTATCGTAAATTGAACCTAACTTTTGCTAGCAGGTTTCCTATCAATCCAAACTGAGGTTT
GCTAGCAAAGTCTAAAAGCATCTGTTTTTGT rs1459727 SEQ ID NO: 35 chr10:62138491
GTACATCCATATGCAAAAGAATGAAGAATGAAACTAGACTTTCCCTTCTTACCCTACATAAAAATCAG
CTGAAAAGGAATCAGAGACCCAAATATAAGAC
C > A
CCAAATGATAAAACTACTAGAAGAAAACACAGGAAATACTGTAGGACATTGGTTTGAGAAAATATTTT
ATGACTAAGTTCTCAAAAGCACAGGCAAAAGA rs1459726 SEQ ID NO: 36 chr10:62138564
AAGGAATCAGAGACCCAAATATAAGACCCCAAATGATAAAACTACTAGAAGAAAACACAGGAAATAC
TGTAGGACATTGGTTTGAGAAAATATTTTATGA
C > A
TAAGTTCTCAAAAGCACAGGCAAAAGAAGCAAAAAGAAACAAACTTGATTATATCAAACTAAAAAGCC
TCTGCACAGAAAAAAAAAATAAAAAACAATCA rs10821723 SEQ ID NO: 37 chr10:62082737
ACAGATTTCTGACCTGTAACTGGAAGAAGTTCTTCATTTACTGAGACAGGCAAGACTATGGGAAGAG
CAGGTTGGGCATGAAGATCGTGAGCTTGGTTTG
G > A
AGCTTGTTATCATTGAGATGCCCATTTGACATCTATCTTTGGATATCCCCACAAGCAGACCTTGAGAC
ACACATTTGAGTGCAAGTAATCTACCCGGGAG rs10821713 SEQ ID NO: 38 chr10:62055781
TTGTTTTGGTTGAAGTAGGTCAAGGATACCAGTCTTCAGGGTACTCTAGAAGGGTCTCAGGGACACC
CAGGGGTTCTTGATTGACCTCATGATACAAAGG
C > T
CTAACACCTCCGAAGAGAACATTTAAGCAAAAGGCAAGACTGAGCAGGAAGCAAAGTCTAAATAAAT
ATAGTGCTACTATTTTTGCAAAGTACAGATCAG rs10821757 SEQ ID NO: 39 chr10:62176620
GACAGCATAGAACATTTTTATCACCACTCAGACTTTTACTGGGCAGTGATGTTCTGTATCTTCATTCC
ACTGGTGGTTCCAGGGGGTCTCATTTGTTACA
A > G
TCCATGAAACCGTACACTTAAAGCTGAGTGTTTTAAGATATATAAATTACACCATAATAGAATTGACTA
CAAAAATGGTTTTTGAGAGAAAATTGTACCA rs10821758 SEQ ID NO: 40 chr10:62176632
CATTTTTATCACCACTCAGACTTTTACTGGGCAGTGATGTTCTGTATCTTCATTCCACTGGTGGTTCC
AGGGGGTCTCATTTGTTACAATCCATGAAACC
G > A
TACACTTAAAGCTGAGTGTTTTAAGATATATAAATTACACCATAATAGAATTGACTACAAAAATGGTTT
TTGAGAGAAAATTGTACCAAGAATAAACTGT SNP Sequence ID:

rs950826 SEQ ID NO: 41 chr10:62183837
TATATATTATTTCCTTGGGCATTCCAGATTTTGTCAAGGAATTTTACATTTTGAGAAGTTGTGCTTGAC
TGTCAGCACTTTGCTATGCTATGATAAAATC
A > G
GAGGACAACAAAAGTTTGATTTAAGGGCTTGGTTAAAAGTGTTGAATTTAAGTTACCCCTATCTGTGA
GTCACTATACTTAGGGTGACCACACATCCTGG rs10994341 SEQ ID NO: 42 chr10:62184907
ACACTATGTTCATAGGGTGCTTGTGGAAATTCAAGTAAGGTGAAATACATTTCAGGGTAGAGAGTGA
CAAAAAGGGAAGCTGGAGAGCTGGGTGGGGCAC
G > A
TGATGGAGTCTTTGTATATTCAGGTAGGAAGGCTGCATTGTTCCCGTGGGCAAGTGAGGGAGCTGC
TGAAGGGTTTTACTGCGTAAGTGACAGAGTCAGA rs3999537 SEQ ID NO: 43 chr10:62188935
AGGACCCAGGGACCCCATCTCAGGTATTTTATGACAGGCAAAAACCCAAGGGAATTCCAGAGCCTG
CTGATATGAAAGTCACATGGTTTTGAAGTTATGA
T > C
GCTGAATCTCTGTAATCCATCAGATCCAACTATTTGACAATTGTTGAGTCACTTATAAATAACACATCT
TGAGGTGCTTTGTTATCTTCTCTCAAGCAGC rs3999538 SEQ ID NO: 44 chr10:62189165
TAGGAGAAAGTAAGAAAGAAAGGAAGTAAAAGGGACTTATATAAGGAGATGTGGAATAGGAAAGAAA
GGCAAGGAGAAAAAGGGGGAAAAGAGGGTACAC
A > G
TATTCCAAGTAAAATAGGTACTCTTACCCCAAATAGAATGGATAGAATTTTCTCTAAAAAGCCTTTACA
GATTAGTAAAGATTAAGAGTTTATTTTTGTA rs10994339 SEQ ID NO: 45 chr10:62182048
CTACCATTAATTATCCTTGGCTAAGACTTAGAGCCACAGATTACTAGTTACTAAAAAGCCACAAGGAA
CAAAAATTCATTCATTCTTCCATTAACTTATT
C > A
ATCTATACAGCTGCCAACAAATACCTGCTGAGCATCTTCTATGTACAAAATTATTCTGCTTCACATGTT
ATTAGCAATGTAAATTTTAACTGACAAAGAC rs10821762 SEQ ID NO: 46 chr10:62182509
TAGCCTATTTCTTTTTTCCCTCCTAAGCTGTAATGGCATTTGCACAGCTGTTACAAGGGAAGTTTTAA
AAATGCAAATAAGAATTAGGTAGACTGCACAA
G > A
CTAATAAAGAGAGCTTTGCCAAATATTAAAAAACGTTCTCAGTCAAAATAATCATACTAATGAAATAGA
AAGCTCATGTGGGAGTGATTTTCAGTAGTTT rs10994342 SEQ ID NO: 47 chr10:62187607
ATACTGATGCCATCCAATCTTCATGCACAGAGAGTCAAAGCAATTTTCCCAAGGTCACCAGGTTAGT
TGGTGGCTTTGATGTAGAGCTAGACTAGAACCC
A > C
GATTTTCTGACAATGCACTGAACAGATGAGATTACTCAAGTATCTGAGAAGGACACATTTGAGTAAG
CAGTTAAACAATGCACAGTTACTAGGGAGCATC rs10821765 SEQ ID NO: 48 chr10:62197950
TATGTATGATGGTCATACCTAATTTTCTACTCTCCAATTCCTAAATTAGCTAGTGGTTTTAGGAACACA
CCTAGCTTAAACATAACTTTCAATACACCAG
G > T
TTGCTCTTGCCCAAAGTTTTATATATATATAAATATGTATGTATGTACATATAAATACATATATATATAT
GTATGTATGTATGTATTGAAGAGTGAGGCT rs12217983 SEQ ID NO: 49 chr10:62064858
AAATCTGATCTGCCTGTGGCAGGCACAGTGGGTGGGGGAGATAGTCAGAAAGGGAAGAATTGCCAT
GAGTTGATGCTCTGGAGAAGGTGAGGCTGGCTTA
A > T
AAAGTCTTCACTATCCCCATGCCCGGCTTCACCCAATTCAGATCAAACTCTTCCATAAACTTCCAGGA
CACACCCCAAGCTCAGCTAACTTCCCTGAAGC rs12780890 SEQ ID NO: 50 chr10:62085906
GTTCTCACTTACAAGTGGGAGCTAAATAAAGAGAACACATAGGCACAGAGAGGGGAACAACAGACA
CTGGGGCCTTTTGGAGGGTGGAGGGTGGGAGGAG
A > G
GAGAGGATCTGGAAAAACCACCAATGGGTACTAGGTTTAATACCTGGGTGATGAAATAATCTGTATA
ACAAACCCCCATGACACAAGTTTACATATATAA

REFERENCES

Lane R M. Antidepressant drug development: Focus on triple monoamine reuptake inhibition. J Psychopharmacol. 2015;29(5):526-544. doi:10.1177/ 0269881114553252 [5]

Bhagwagar Z, Torbeyns A, Hennicken D, et al. Assessment of the Efficacy and Safety of BMS-820836 in Patients With Treatment-Resistant Major Depression: Results From 2 Randomized, Double-Blind Studies. J Clin Psychopharmacol. 2015;35(4):454-459. doi :10.1097/ [10] JCP.0000000000000335

TABLE 1A

| | | | | The correlation between a pair of loci. | |
| | | Distance | D' value of linkage | | |
| Variant | Location | (bp) | equilibrium | R2 | SEQID NO: |
|---|---|---|---|---|---|
| rs12217173 | chr10: 62091912 | 0 | 1 | 1 | SEQID NO: 51 |
| rs12219340 | chr10: 62092193 | 281 | 1 | 0.996 | SEQID NO: 1 |
| rs4612751 | chr10: 62092917 | 1005 | 1 | 0.996 | SEQID NO: 2 |
| rs10994306 | chr10: 62097576 | 5664 | 0.9919 | 0.984 | SEQID NO: 3 |
| rs7083556 | chr10: 62121387 | 29475 | 0.9919 | 0.984 | SEQID NO: 4 |
| rs12572120 | chr10: 62088304 | −3608 | 1 | 0.9762 | SEQID NO: 5 |
| rs10821741 | chr10: 62115503 | 23591 | 0.9919 | 0.976 | SEQID NO: 6 |
| rs35050621 | chr10: 62098778 | 6866 | 0.9879 | 0.976 | SEQID NO: 7 |
| rs10821738 | chr10: 62109449 | 17537 | 0.9879 | 0.976 | SEQID NO: 8 |
| rs10821739 | chr10: 62109643 | 17731 | 0.9879 | 0.976 | SEQID NO: 9 |
| rs10821740 | chr10: 62113686 | 21774 | 0.9879 | 0.976 | SEQID NO: 10 |
| rs12775352 | chr10: 62085590 | −6322 | 0.9959 | 0.9682 | SEQID NO: 11 |
| rs10994312 | chr10: 62122704 | 30792 | 0.9874 | 0.9028 | SEQID NO: 12 |
| rs10994313 | chr10: 62122781 | 30869 | 0.9874 | 0.9028 | SEQID NO: 13 |
| rs12781371 | chr10: 62085918 | −5994 | 0.9711 | 0.9021 | SEQID NO: 14 |
| rs7902423 | chr10: 62123689 | 31777 | 0.9831 | 0.8877 | SEQID NO: 15 |
| rs7917429 | chr10: 62123720 | 31808 | 0.9831 | 0.8877 | SEQID NO: 16 |
| rs7917540 | chr10: 62123774 | 31862 | 0.9831 | 0.8877 | SEQID NO: 17 |
| rs10994319 | chr10: 62130265 | 38353 | 0.983 | 0.8804 | SEQID NO: 18 |
| rs1824405 | chr10: 62130662 | 38750 | 0.983 | 0.8804 | SEQID NO: 19 |
| rs1010556 | chr10: 62133503 | 41591 | 0.983 | 0.8804 | SEQID NO: 20 |
| rs10994326 | chr10: 62158385 | 66473 | 0.9829 | 0.8731 | SEQID NO: 21 |
| rs10821747 | chr10: 62152721 | 60809 | 0.9788 | 0.8728 | SEQID NO: 22 |
| rs12764333 | chr10: 62175060 | 83148 | 0.9786 | 0.8619 | SEQID NO: 23 |
| rs1459729 | chr10: 62122754 | 30842 | 0.9386 | 0.8565 | SEQID NO: 24 |
| rs10994331 | chr10: 62171445 | 79533 | 0.9785 | 0.8547 | SEQID NO: 25 |
| rs10994332 | chr10: 62171600 | 79688 | 0.9785 | 0.8547 | SEQID NO: 26 |
| rs7100501 | chr10: 62170830 | 78918 | 0.9659 | 0.8431 | SEQID NO: 27 |
| rs3851251 | chr10: 62130429 | 38517 | 0.934 | 0.8344 | SEQID NO: 28 |
| rs7072841 | chr10: 62131838 | 39926 | 0.934 | 0.8344 | SEQID NO: 29 |
| rs1459728 | chr10: 62132129 | 40217 | 0.934 | 0.8344 | SEQID NO:: 30 |
| rs1380455 | chr10: 62132820 | 40908 | 0.934 | 0.8344 | SEQID NO: 31 |
| rs1380454 | chr10: 62133051 | 41139 | 0.934 | 0.8344 | SEQID NO: 32 |
| rs10821744 | chr10: 62127894 | 35982 | 0.9338 | 0.8308 | SEQID NO: 33 |
| rs4147263 | chr10: 62137665 | 45753 | 0.9335 | 0.8235 | SEQID NO: 34 |
| rs1459727 | chr10: 62138491 | 46579 | 0.9295 | 0.8198 | SEQID NO: 35 |
| rs1459726 | chr10: 62138564 | 46652 | 0.9295 | 0.8198 | SEQID NO: 36 |

TABLE 1B

| | | | | The correlation between a | |
| | | | D' value of | pair of loci. | |
| | | Distance | linkage | R2 | |
| Variant | Location | (bp) | equilibrium | | SEQID NO: |
|---|---|---|---|---|---|

Variants linked to rs12217173: AFR, African

| rs12217173 | chr10: 62091912 | 0 | 1 | 1 | SEQID NO: 51 |
| rs12219340 | chr10: 62092193 | 281 | 1 | 1 | SEQID NO: 1 |
| rs4612751 | chr10: 62092917 | 1005 | 1 | 1 | SEQID NO: 2 |
| rs12572120 | chr10: 62088304 | −3608 | 0.9659 | 0.9109 | SEQID NO: 5 |
| rs10821723 | chr10: 62082737 | −9175 | 0.9353 | 0.8452 | SEQID NO: 37 |
| rs10994306 | chr10: 62097576 | 5664 | 0.9213 | 0.8323 | SEQID NO: 3 |

TABLE 1C

Variants linked to rs12217173: AMR, Ad Mixed American

| | | | | The correlation between a | |
| | | | D' value of | pair of loci. | |
| | | Distance | linkage | R2 | |
| Variant | Location | (bp) | equilibrium | | SEQID NO: |
|---|---|---|---|---|---|
| rs12217173 | chr10: 62091912 | 0 | 1 | 1 | SEQID NO: 51 |
| rs4612751 | chr10: 62092917 | 1005 | 1 | 1 | SEQID NO: 2 |
| rs12219340 | chr10: 62092193 | 281 | 1 | 0.9929 | SEQID NO: 1 |
| rs12572120 | chr10: 62088304 | −3608 | 1 | 0.9859 | SEQID NO: 5 |
| rs10994306 | chr10: 62097576 | 5664 | 0.9928 | 0.9646 | SEQID NO: 3 |
| rs10821738 | chr10: 62109449 | 17537 | 0.9927 | 0.9576 | SEQID NO: 8 |
| rs10821739 | chr10: 62109643 | 17731 | 0.9927 | 0.9576 | SEQID NO: 9 |
| rs10821740 | chr10: 62113686 | 21774 | 0.9927 | 0.9576 | SEQID NO: 10 |
| rs10821741 | chr10: 62115503 | 23591 | 0.9927 | 0.9576 | SEQID NO: 6 |
| rs35050621 | chr10: 62098778 | 6866 | 0.9927 | 0.9506 | SEQID NO: 7 |
| rs10994312 | chr10: 62122704 | 30792 | 0.9926 | 0.9299 | SEQID NO: 12 |
| rs10994313 | chr10: 62122781 | 30869 | 0.9926 | 0.9299 | SEQID NO: 13 |
| rs7917540 | chr10: 62123774 | 31862 | 0.9925 | 0.923 | SEQID NO: 17 |
| rs12775352 | chr10: 62085590 | −6322 | 0.9855 | 0.918 | SEQID NO: 11 |
| rs7902423 | chr10: 62123689 | 31777 | 0.9925 | 0.9161 | SEQID NO: 15 |
| rs7917429 | chr10: 62123720 | 31808 | 0.9925 | 0.9161 | SEQID NO: 16 |
| rs10821747 | chr10: 62152721 | 60809 | 0.9925 | 0.9161 | SEQID NO: 22 |
| rs10994326 | chr10: 62158385 | 66473 | 0.9925 | 0.9161 | SEQID NO: 21 |
| rs10994319 | chr10: 62130265 | 38353 | 0.9924 | 0.9093 | SEQID NO: 18 |
| rs1824405 | chr10: 62130662 | 38750 | 0.9924 | 0.9093 | SEQID NO: 19 |
| rs1010556 | chr10: 62133503 | 41591 | 0.9924 | 0.9093 | SEQID NO: 20 |
| rs7100501 | chr10: 62170830 | 78918 | 0.9924 | 0.9093 | SEQID NO: 27 |
| rs10994331 | chr10: 62171445 | 79533 | 0.9924 | 0.9093 | SEQID NO: 25 |
| rs10994332 | chr10: 62171600 | 79688 | 0.9924 | 0.9093 | SEQID NO: 26 |
| rs10821744 | chr10: 62127894 | 35982 | 0.985 | 0.9023 | SEQID NO: 33 |
| rs3851251 | chr10: 62130429 | 38517 | 0.985 | 0.9023 | SEQID NO: 28 |
| rs7072841 | chr10: 62131838 | 39926 | 0.985 | 0.9023 | SEQID NO: 29 |
| rs1459728 | chr10: 62132129 | 40217 | 0.985 | 0.9023 | SEQID NO: 30 |
| rs1380455 | chr10: 62132820 | 40908 | 0.985 | 0.9023 | SEQID NO: 31 |
| rs1380454 | chr10: 62133051 | 41139 | 0.985 | 0.9023 | SEQID NO: 32 |
| rs1459729 | chr10: 62122754 | 30842 | 0.9636 | 0.9022 | SEQID NO: 24 |
| rs12764333 | chr10: 62175060 | 83148 | 0.9561 | 0.8818 | SEQID NO: 23 |
| rs4147263 | chr10: 62137665 | 45753 | 0.963 | 0.8817 | SEQID NO: 34 |
| rs1459727 | chr10: 62138491 | 46579 | 0.963 | 0.8817 | SEQID NO: 35 |
| rs1459726 | chr10: 62138564 | 46652 | 0.963 | 0.8817 | SEQID NO: 36 |
| rs7083556 | chr10: 62121387 | 29475 | 0.9636 | 0.8655 | SEQID NO: 4 |
| rs12781371 | chr10: 62085918 | −5994 | 0.9283 | 0.8556 | SEQID NO: 14 |
| rs10821723 | chr10: 62082737 | −9175 | 0.9691 | 0.8416 | SEQID NO: 37 |
| rs10821713 | chr10: 62055781 | −36131 | 0.9616 | 0.8348 | SEQID NO: 38 |
| rs10821757 | chr10: 62176620 | 84708 | 0.9686 | 0.8219 | SEQID NO: 39 |
| rs10821758 | chr10: 62176632 | 84720 | 0.9534 | 0.8084 | SEQID NO: 40 |
| rs950826 | chr10: 62183837 | 91925 | 0.9534 | 0.8084 | SEQID NO: 41 |
| rs10994341 | chr10: 62184907 | 92995 | 0.9534 | 0.8084 | SEQID NO: 42 |
| rs3999537 | chr10: 62188935 | 97023 | 0.9534 | 0.8084 | SEQID NO: 43 |
| rs3999538 | chr10: 62189165 | 97253 | 0.9534 | 0.8084 | SEQID NO: 44 |
| rs10994339 | chr10: 62182048 | 90136 | 0.9531 | 0.8019 | SEQID NO: 45 |
| rs10821762 | chr10: 62182509 | 90597 | 0.9459 | 0.8018 | SEQID NO: 46 |
| rs10994342 | chr10: 62187607 | 95695 | 0.9459 | 0.8018 | SEQID NO: 47 |
| rs10821765 | chr10: 62197950 | 106038 | 0.9459 | 0.8018 | SEQID NO: 48 |

TABLE 1D

| | | | | The correlation between a | |
|---|---|---|---|---|---|
| | | Distance | D' value of linkage | pair of loci. | |
| Variant | Location | (bp) | equilibrium | R2 | SEQID NO: |
| rs12217173 | chr10: 62091912 | 0 | 1 | 1 | |
| rs12219340 | chr10: 62092193 | 281 | 1 | 1 | SEQID NO: 1 |
| rs4612751 | chr10: 62092917 | 1005 | 1 | 1 | SEQID NO: 2 |
| rs10994306 | chr10: 62097576 | 5664 | 0.9797 | 0.956 | SEQID NO: 3 |
| rs7083556 | chr10: 62121387 | 29475 | 0.9797 | 0.956 | SEQID NO: 4 |
| rs12572120 | chr10: 62088304 | −3608 | 0.9958 | 0.926 | SEQID NO: 5 |
| rs10821741 | chr10: 62115503 | 23591 | 0.9797 | 0.956 | SEQID NO: 6 |
| rs35050621 | chr10: 62098778 | 6866 | 0.9797 | 0.956 | SEQID NO: 7 |
| rs10821738 | chr10: 62109449 | 17537 | 0.9837 | 0.9599 | SEQID NO: 8 |
| rs10821739 | chr10: 62109643 | 17731 | 0.9837 | 0.9599 | SEQID NO: 9 |
| rs10821740 | chr10: 62113686 | 21774 | 0.9797 | 0.956 | SEQID NO: 10 |
| rs12775352 | chr10: 62085590 | −6322 | 0.9545 | 0.8681 | SEQID NO: 11 |
| rs10994312 | chr10: 62122704 | 30792 | 0.9754 | 0.9324 | SEQID NO: 12 |
| rs10994313 | chr10: 62122781 | 30869 | 0.9754 | 0.9324 | SEQID NO: 13 |
| rs12781371 | chr10: 62085918 | −5994 | 0.9545 | 0.8681 | SEQID NO: 14 |
| rs1459729 | chr10: 62122754 | 30842 | 0.9714 | 0.9285 | SEQID NO: 24 |
| rs10821713 | chr10: 62055781 | −36131 | 0.9336 | 0.8238 | SEQID NO: 38 |
| rs12217983 | chr10: 62064858 | −27054 | 0.9495 | 0.8413 | SEQID NO: 49 |
| rs12780890 | chr10: 62085906 | −6006 | 0.9534 | 0.8187 | SEQID NO: 50 |

TABLE 1E

Variants linked to rs12217173: EAS, South Asian

| | | | | The correlation between a | |
|---|---|---|---|---|---|
| | | Distance | D' value of linkage | pair of loci. | |
| Variant | Location | (bp) | equilibrium | R2 | SEQID NO: |
| rs12217173 | chr10: 62091912 | 0 | 1 | 1 | SEQID NO: 51 |
| rs12219340 | chr10: 62092193 | 281 | 1 | 1 | SEQID NO: 1 |
| rs4612751 | chr10: 62092917 | 1005 | 1 | 1 | SEQID NO: 2 |
| rs10994306 | chr10: 62097576 | 5664 | 0.9959 | 0.9837 | SEQID NO: 3 |
| rs7083556 | chr10: 62121387 | 29475 | 0.9918 | 0.9756 | SEQID NO: 4 |
| rs12572120 | chr10: 62088304 | −3608 | 0.9959 | 0.9756 | SEQID NO: 5 |
| rs10821741 | chr10: 62115503 | 23591 | 0.9959 | 0.9797 | SEQID NO: 6 |
| rs35050621 | chr10: 62098778 | 6866 | 0.9877 | 0.9756 | SEQID NO: 7 |
| rs10821738 | chr10: 62109449 | 17537 | 0.9959 | 0.9837 | SEQID NO: 8 |
| rs10821739 | chr10: 62109643 | 17731 | 0.9959 | 0.9837 | SEQID NO: 9 |
| rs10821740 | chr10: 62113686 | 21774 | 0.9959 | 0.9797 | SEQID NO: 10 |
| rs12775352 | chr10: 62085590 | −6322 | 0.9875 | 0.9437 | SEQID NO: 11 |
| rs10994312 | chr10: 62122704 | 30792 | 0.9629 | 0.9158 | SEQID NO: 12 |
| rs10994313 | chr10: 62122781 | 30869 | 0.9629 | 0.9158 | SEQID NO: 13 |
| rs12781371 | chr10: 62085918 | −5994 | 0.9711 | 0.9277 | SEQID NO: 14 |
| rs7902423 | chr10: 62123689 | 31777 | 0.9546 | 0.9002 | SEQID NO: 15 |
| rs7917429 | chr10: 62123720 | 31808 | 0.9546 | 0.9002 | SEQID NO: 16 |
| rs7917540 | chr10: 62123774 | 31862 | 0.9547 | 0.904 | SEQID NO: 17 |
| rs10994319 | chr10: 62130265 | 38353 | 0.9138 | 0.8315 | SEQID NO: 18 |
| rs1824405 | chr10: 62130662 | 38750 | 0.9138 | 0.8315 | SEQID NO: 19 |
| rs1010556 | chr10: 62133503 | 41591 | 0.9179 | 0.839 | SEQID NO: 20 |
| rs10994326 | chr10: 62158385 | 66473 | 0.9217 | 0.8391 | SEQID NO: 21 |
| rs10821747 | chr10: 62152721 | 60809 | 0.9215 | 0.8354 | SEQID NO: 22 |
| rs12764333 | chr10: 62175060 | 83148 | 0.9086 | 0.8022 | SEQID NO: 23 |
| rs1459729 | chr10: 62122754 | 30842 | 0.9621 | 0.8777 | SEQID NO: 24 |
| rs10994331 | chr10: 62171445 | 79533 | 0.9134 | 0.8241 | SEQID NO: 25 |
| rs10994332 | chr10: 62171600 | 79688 | 0.9134 | 0.8241 | SEQID NO: 26 |
| rs7100501 | chr10: 62170830 | 78918 | 0.9136 | 0.8278 | SEQID NO: 27 |
| rs10821723 | chr10: 62082737 | −9175 | 0.9494 | 0.8545 | SEQID NO: 37 |

The invention claimed is:

1. A method of identifying and treating a subject that has a CNS disease or disorder, comprising:

assaying a biological sample from the subject;

detecting the presence of the GG genotype of SNP rs12217173 in the sample;

identifying the subject as likely to be responsive to treatment with liafensine; and, administering, to the identified subject, an effective amount of liafensine;

wherein the CNS disease or disorder is selected from the group consisting of a major depressive disorder (MDD), treatment-resistant depression (TRD), major depression with psychotic feature(s), depression with peri- or postpartum onset, a post-traumatic stress disorder (PTSD), a bipolar disorder, an obsessive-compulsive disorder (OCD), an eating disorder, attention-deficit hyperactivity disorder (ADHD), a sleep disorder, a substance use disorder, Tourette syndrome (TS), schizophrenia, epilepsy, migraine, and an autism spectrum disorder.

2. The method of claim 1, wherein the CNS disease or disorder is major depressive disorder (MDD).

3. The method of claim 1, wherein the CNS disease or disorder is treatment-resistant depression (TRD).

4. The method of claim 1, wherein the biological sample is assayed by polymerase chain reaction (PCR) performed using a reagent, comprising:

i) one or more primers that allow for amplification of a specific part of or all of the SNP locus or SNPs loci being assayed; and, ii) one or more probes that selectively or specifically hybridize to a specific part of or all of the SNP locus or SNPs loci being assayed.

5. The method of claim 4, wherein the CNS disease or disorder is major depressive disorder (MDD).

6. The method of claim 4, wherein the CNS disease or disorder is treatment-resistant depression (TRD).

7. The method of claim 4, wherein wherein the reagent, comprises:

i) a plurality of primers that allow for amplification of a specific part of or all of the SNP locus or SNPs loci being assayed; and, ii) a plurality of probes that selectively or specifically hybridize to a specific part of or all of the SNP locus or SNPs loci being assayed.

8. The method of claim 7, wherein the CNS disease or disorder is major depressive disorder (MDD).

9. The method of claim 7, wherein the CNS disease or disorder is treatment-resistant depression (TRD).

10. The method of claim 1, further comprising:

prior to the assaying step, obtaining a biological sample from the subject; and, optionally isolating genomic DNA from the biological sample.

11. The method of claim 2, further comprising:

prior to the assaying step, obtaining a biological sample from the subject; and, optionally isolating genomic DNA from the biological sample.

12. The method of claim 3, further comprising:

prior to the assaying step, obtaining a biological sample from the subject; and, optionally isolating genomic DNA from the biological sample.

13. The method of claim 4, wherein each SNP assayed comprises 4, 8, 10, 15, 20, 25, 30, 50, 60, 100, 300, or 500 nucleotides on either side of the SNP position.

14. The method of claim 7, wherein each SNP assayed comprises 4, 8, 10, 15, 20, 25, 30, 50, 60, 100, 300, or 500 nucleotides on either side of the SNP position.

* * * * *

SEQUENCE LISTING

<160> NUMBER OF SEQ ID NOS: 51

<210> SEQ ID NO 1
<211> LENGTH: 201
<212> TYPE: DNA
<213> ORGANISM: Homo sapiens

<400> SEQUENCE: 1
aaaataggac acaatttctt tttagaagct cacctcatat caagtacata ttctaatgca        60
aagtatgaat ttcacaaagg gctgagtatg taggtgttgg ygccactgtt ctgatgttag       120
cacccagcac ttatttttct aacttttaga aaaatgttta ctaatttctg ccagttgcac       180
ccctttgtag tcacctccca g                                                  201

<210> SEQ ID NO 2
<211> LENGTH: 201
<212> TYPE: DNA
<213> ORGANISM: Homo sapiens

<400> SEQUENCE: 2
tttaatcttt ttattttgat aaagaactat aaaatgggac atatggatat acatctaaag        60
tctccaaatt tccatagtgt gttttttgag catctttta ktattattat actttaagtt        120
ctgagataca tgtgcagaat gtgcaggttg ttacataggt atacacgtgt catggtggtt       180
tgctgcaccc atcaacccgt c                                                  201

<210> SEQ ID NO 3
<211> LENGTH: 201
<212> TYPE: DNA
<213> ORGANISM: Homo sapiens

<400> SEQUENCE: 3
gtaggtgcta aggcatacca caaatgaata aagcaagata ttccctgact tcacagtttt        60
ataaacatag gttaacaagt aattcttatt actcacacat yctggtgagt gctatagtag       120
aaaaatatat tattggagta ccatattagg aaaaagcatt ttgtatatga ctggccagtg       180
aagaagcatt gaatttatcc c                                                  201

<210> SEQ ID NO 4
<211> LENGTH: 201
<212> TYPE: DNA
<213> ORGANISM: Homo sapiens

<400> SEQUENCE: 4
ttgaaaatat ttcatcaatg tattattcca cttgtatttc atatagttca gtcactttat        60
tcagtaagaa aggaactggc aggagtttgt agtcagggat wtcattcatt gtagtggaac       120
aaggtatggg ggaagtggaa gagatgtagt ccaagaaata ttctgaggat tattatttac       180
aatatattcc tagttatagt t                                                  201

<210> SEQ ID NO 5
<211> LENGTH: 201
<212> TYPE: DNA
<213> ORGANISM: Homo sapiens

<400> SEQUENCE: 5
ttaaataaaa ggattatatc tctatggtgg aatgtactgc aggcattaaa tcaatgttta        60
tgtacctcta cacaaataaa ctagaaaatc tagaagaaat kgataaattc ctggacacat       120
acaccctccc aagactaaac caggaagaag tccaatccct gaatggacca ataacaagtt       180

-continued

```
ctgaaattga ggcagtaatt a                                                201

<210> SEQ ID NO 6
<211> LENGTH: 201
<212> TYPE: DNA
<213> ORGANISM: Homo sapiens

<400> SEQUENCE: 6
accatgaagt gctcgctcac ctccacggtc atagtgcaat attcctttgt ttgtcgatta        60
taaggtgcac ttcaaacctt ccccaacatc tccctccagg stccttttct taatgtgcct       120
acaattagtc agtcgtattt tgccacctca caactttaaa caaagttcta catttcagac       180
acaagtggaa aaatgaggcc a                                                201

<210> SEQ ID NO 7
<211> LENGTH: 201
<212> TYPE: DNA
<213> ORGANISM: Homo sapiens
<220> FEATURE:
<221> NAME/KEY: variation
<222> LOCATION: (101)..(101)
<223> OTHER INFORMATION: N can be absent
<220> FEATURE:
<221> NAME/KEY: misc_feature
<222> LOCATION: (101)..(101)
<223> OTHER INFORMATION: n is a, c, g, or t

<400> SEQUENCE: 7
tgtctccaaa taaataggag ccgtatttgg gtctggaagc catgaagtct tggggagagc        60
ttcacagatg tttggtgggt ttccaaagac aattagcata ntactccaag agtggagtga       120
aatagaatgt gtgcttgttt cttttctttg ttagtaccaa aatagatttg tgtttatttg       180
atagaaaaaa aaaattctag c                                                201

<210> SEQ ID NO 8
<211> LENGTH: 201
<212> TYPE: DNA
<213> ORGANISM: Homo sapiens

<400> SEQUENCE: 8
agagactcaa aataactcaa attctttggc tacgaataac tctatttatc tgcaaaaagc        60
cacatgaacc ctaattcttt ctaagcacaa agaaacagag ragaggatat ataaatagta       120
gcaatcattg gaacaaaagt tgaaatgagg gtagaaatag agactcccac cctctgttct       180
cccttctaat aggcacaaat a                                                201

<210> SEQ ID NO 9
<211> LENGTH: 201
<212> TYPE: DNA
<213> ORGANISM: Homo sapiens

<400> SEQUENCE: 9
acaaatattc atggaagaat aagaaacttc agagcaacat gggtctctgg acaagtcata        60
atttttagaa gtgagtggag acttagaggg aacagtaaga yaagaaaata gcagggaaag       120
accataaagt aacggacttg tctagttaat aagcattttc ctggaaatga atggaatagg       180
atacaatggt gagaatacac a                                                201

<210> SEQ ID NO 10
<211> LENGTH: 201
<212> TYPE: DNA
```

<213> ORGANISM: Homo sapiens

<400> SEQUENCE: 10
caattctctt aggattcccc agggagatcc cagcctgtta attttcccca gtagttgtca      60
gcaggcaggg ccagcagagc tacgtgcatt gttatcagct yagcctgtga ccaggcacga     120
aatggctgtg cttggcttgc gcatctccat atccacgtgc agtccatgat gtcatggagg     180
ccgtgttgcc tcctgcacag c                                               201

<210> SEQ ID NO 11
<211> LENGTH: 201
<212> TYPE: DNA
<213> ORGANISM: Homo sapiens

<400> SEQUENCE: 11
aagacctaaa gcagaaacat catttgaccc agcaatccca ttactgggta tatacccaaa      60
ggagtataaa tcatcctttt ataaagacac atgcacacat mcgttctttg cagcaccagt     120
cacaataaca aagacatgga atcaacctaa atgcccatca atgatagacc gaataaagaa     180
aatgtggtac atatacacca t                                               201

<210> SEQ ID NO 12
<211> LENGTH: 201
<212> TYPE: DNA
<213> ORGANISM: Homo sapiens

<400> SEQUENCE: 12
aaccaggtgg attcacagag aaaaactctg tctgaggaat ttgggaaagg ctttacccgg      60
ggacattaga gctggtcctg gagagtagat agggtgggct mtcctggaca tagatgactt     120
gttctctgtt catccattgg atattcccaa gccgttttct tttgctaccc tttccagcag     180
aaatgccaac tacttacttt t                                               201

<210> SEQ ID NO 13
<211> LENGTH: 201
<212> TYPE: DNA
<213> ORGANISM: Homo sapiens

<400> SEQUENCE: 13
ctggagagta gatagggtgg gctatcctgg acatagatga cttgttctct gttcatccat      60
tggatattcc caagccgttt tcttttgcta ccctttccag sagaaatgcc aactacttac     120
ttttccagtc tcccttgcag ctggggttgc ggcgggcggg cgggggaggg gggcgggggg     180
cgcaatacaa catgcagttc t                                               201

<210> SEQ ID NO 14
<211> LENGTH: 201
<212> TYPE: DNA
<213> ORGANISM: Homo sapiens

<400> SEQUENCE: 14
aagtgggagc taaataaaga gaacacatag gcacagagag gggaacaaca gacactgggg      60
ccttttggag ggtggagggt gggaggagag sgaggatctg saaaaaccac caatgggtac     120
taggtttaat acctgggtga tgaaataatc tgtataacaa acccccatga cacaagttta     180
catatataac acacctgcac g                                               201

<210> SEQ ID NO 15
<211> LENGTH: 201

```
<212> TYPE: DNA
<213> ORGANISM: Homo sapiens

<400> SEQUENCE: 15
gcatataatg tcctttctaa atcccttttc ttatagaaaa acatcgtaag tttttataaa      60
aagataggat taatttattt ttaagctaac aacaaaggtg ytaccagccc actgtagtta     120
aaaaagagga aggagaagtg tttttttttt tttttttttt ttttaacttt aagagaaaac     180
aggccgggct cagtggctca a                                               201

<210> SEQ ID NO 16
<211> LENGTH: 201
<212> TYPE: DNA
<213> ORGANISM: Homo sapiens

<400> SEQUENCE: 16
tatagaaaaa catcgtaagt ttttataaaa agataggatt aatttatttt taagctaaca      60
acaaaggtgt taccagccca ctgtagttaa aaaagaggaa rgagaagtgt tttttttttt     120
tttttttttt tttaacttta agagaaaaca ggccgggctc agtggctcaa gcctgtaatc     180
ccagcacttt cggaggctga g                                               201

<210> SEQ ID NO 17
<211> LENGTH: 201
<212> TYPE: DNA
<213> ORGANISM: Homo sapiens

<400> SEQUENCE: 17
ctaacaacaa aggtgttacc agcccactgt agttaaaaaa gaggaaggag aagtgttttt      60
tttttttttt tttttttta actttaagag aaaacaggcc rggctcagtg gctcaagcct     120
gtaatcccag cactttcgga ggctgaggcg ggcagatcac tgaaggtcag gagttcctga     180
ccagcctggc caacatggtg a                                               201

<210> SEQ ID NO 18
<211> LENGTH: 201
<212> TYPE: DNA
<213> ORGANISM: Homo sapiens

<400> SEQUENCE: 18 atttttaaa aatcgctatg aatagcattg aaaaattaat ttaaaaagaa aaaatatata      60
aaaatcacta ttcaaatatt gctctcaaag tagaagaatg yattaaaaca tgacactgtt     120
ttgaaggccc tatcatgaat ccaacaaata cttacagcgc agtaaatggg agaacacaat     180
tataacatca cagttcttat c                                               201

<210> SEQ ID NO 19
<211> LENGTH: 201
<212> TYPE: DNA
<213> ORGANISM: Homo sapiens

<400> SEQUENCE: 19
tcagcatttg tgagctagct ctgaaaactc aagctaaaca tcaacctgag ataacatttc      60
ttactttgca aacatactgt taatagttga aagtaatagg rgaaatcggg aggaaaggag     120
ggggcataac ctaaataagt ggaaaccaat ccctgtgcat tccattctca atacaaggta     180
tcaccacata ttggttacag a                                               201

<210> SEQ ID NO 20
```

-continued

```
<211> LENGTH: 201
<212> TYPE: DNA
<213> ORGANISM: Homo sapiens

<400> SEQUENCE: 20
tcacagatgg aaggcaaggt cacggaaggc aagcaaggct gagatggttt tagagacagg      60
tggcatggag gatctctccc ttgctttaca atttgcccca ycacactcca tgaattctaa     120
tatgctcttg gagtgaggga tatagccgtc cttgttctag cactgaaagt ggaatcctgg     180
gaaacctttc agtcctgggc a                                               201

<210> SEQ ID NO 21
<211> LENGTH: 201
<212> TYPE: DNA
<213> ORGANISM: Homo sapiens

<400> SEQUENCE: 21
atacccatga aaatttgtcc tctggatttg aacatgatca ctgacatttc agtgatggaa      60
aaacgtatgt tgctatgtac attttctata ccatgtccac rcagataacg tttctttaat     120
tcactcattt aacaaatatt tattgggtac cttctttaat gaagcagcat aatccaaaca     180
ttatttaaga cacccaaact c                                               201

<210> SEQ ID NO 22
<211> LENGTH: 201
<212> TYPE: DNA
<213> ORGANISM: Homo sapiens

<400> SEQUENCE: 22
tggttgcagt gagctgagat cacaccactg cactccagtc tgggtgacag agcaaggctc      60
tgtcccttgg ctccccactc cctcccccaa aaaagaaaaa raaagctaag gacaaaaatt     120
cttaagtgac ttccctttct caagaaaaaa agaaaaaatc tgttcttgtt ttataaaagt     180
cccaggtaca agaattccta a                                               201

<210> SEQ ID NO 23
<211> LENGTH: 201
<212> TYPE: DNA
<213> ORGANISM: Homo sapiens

<400> SEQUENCE: 23
gtctggcctg gagctactga aaatcctgcc tacaaggact tgtggaagga gcatcatgcc      60
tccgttattc ccagaggccg agggaggaaa atgagcagac yagcctgtgt ttttggaagg     120
aaactcctaa aaactacaat cattcagagg cagcctggat catctgcaaa acgtaaaaag     180
aacctttaaa ttcctcttaa a                                               201

<210> SEQ ID NO 24
<211> LENGTH: 201
<212> TYPE: DNA
<213> ORGANISM: Homo sapiens

<400> SEQUENCE: 24
ctttacccgg ggacattaga gctggtcctg gagagtagat agggtgggct atcctggaca      60
tagatgactt gttctctgtt catccattgg atattcccaa rccgttttct tttgctaccc     120
tttccagcag aaatgccaac tacttacttt tccagtctcc cttgcagctg gggttgcggc     180
gggcgggcgg gggagggggg c                                               201
```

```
<210> SEQ ID NO 25
<211> LENGTH: 201
<212> TYPE: DNA
<213> ORGANISM: Homo sapiens

<400> SEQUENCE: 25
cctctgtgcc cctctcacca accctgtaga agtaggaata gaaatgaatt aagcagcacc      60
acagtggact agagaagggc ccagactcca ggaccagact kcctggatat gaatcccagc     120
atggtcactt actaggaaaa taaccttaga taagtgaccc catctgcctg tgcctcagtt     180
tccacatttc taaagtgtag a                                              201

<210> SEQ ID NO 26
<211> LENGTH: 201
<212> TYPE: DNA
<213> ORGANISM: Homo sapiens

<400> SEQUENCE: 26
gaccccatct gcctgtgcct cagtttccac atttctaaag tgtagaaatg aggatataga      60
agaaagtact catgagattt tgaaatgaaa gagtatttat raagtgctta atccagtaag     120
tactatataa aaataaggag tcaaatttaa aaaaattaga agacagccag ggcaattaat     180
cccagctgca tactgcctag t                                              201

<210> SEQ ID NO 27
<211> LENGTH: 201
<212> TYPE: DNA
<213> ORGANISM: Homo sapiens

<400> SEQUENCE: 27
cctctcccat ccaatcttta tccctctcct tcctttttct tctcctggct tttgacccag      60
ctaccaagga tccactgggg gaactccaag gaactggtgg rtaatggagc cccaagctgg     120
aaggcgcttg gtttccaaat aactgcagcc tctacaccaa gccacattgg actgtgacgt     180
gaaccagaaa caaactttta t                                              201

<210> SEQ ID NO 28
<211> LENGTH: 201
<212> TYPE: DNA
<213> ORGANISM: Homo sapiens

<400> SEQUENCE: 28
aatgggagaa cacaattata acatcacagt tcttatcaca aagattgcca tagtctagat      60
ctgagaaggc ttttaattag tatttctaac atttatcatg yccagtgaat gacagcttag     120
acaaaaatca gtggcttcaa cacttctcaa aattattcag taattattct ccaggtttct     180
aattcatcag cttggtagat t                                              201

<210> SEQ ID NO 29
<211> LENGTH: 201
<212> TYPE: DNA
<213> ORGANISM: Homo sapiens

<400> SEQUENCE: 29
gtgaggcata aggtaatggg aaatactaca atggaaaaca cagacgatag aatattagag      60
ggaaaaagct ttcacatctt tataattcta cactttaccg ytgtttataa atgttgcagt     120
atatccacaa atcagttaaa ttcatatatt tcaaagccaa ccaagagata aaactaaaag     180
ttaaagagga agaaaaaaat t                                              201
```

```
<210> SEQ ID NO 30
<211> LENGTH: 201
<212> TYPE: DNA
<213> ORGANISM: Homo sapiens

<400> SEQUENCE: 30
ttaccaattg tggcaacaac tgtggatgta ctacatcaat atattatgat ctagacaatc        60
cacacatgaa atagtgtcaa ttctagttat ctcatgatgg ytaagagagg atttaagggg       120
tatcacgatt ctctgtctta tgaagaccag ctaaagaaac agggagcgtt taacttgaag       180
agaagcagca gcaccaacat a                                                  201

<210> SEQ ID NO 31
<211> LENGTH: 201
<212> TYPE: DNA
<213> ORGANISM: Homo sapiens

<400> SEQUENCE: 31
ataaaaatag aggcatgatc agtagatttt tttaaaacca gtatttattg taaagcaatt        60
tgaaatcatg tttgtcatct ccatcatatg aatttgagta maaagtgatc ctcttgcaca       120
tgcaatattt tagttacata actttgtagc atcccccatc attttctaat aaaacaatgg       180
tgggctttct ctgactggga c                                                  201

<210> SEQ ID NO 32
<211> LENGTH: 201
<212> TYPE: DNA
<213> ORGANISM: Homo sapiens

<400> SEQUENCE: 32
aagtagtaat gttctttatg tctatttatg tccaatatct catcgggtag aaggtggcca        60
ggccaggggc ctcttgtgtg gggagaagat ttaaatgtcc rtcccttggc taaggcagta       120
taggcagggg aaagtcaaag ttggaaataa tcaaaataag aatgcaaatg aataagaaac       180
aagatcctgg gagttgaaga g                                                  201

<210> SEQ ID NO 33
<211> LENGTH: 201
<212> TYPE: DNA
<213> ORGANISM: Homo sapiens

<400> SEQUENCE: 33
tttcattgta tactccacgt gttgcaataa tgaaatacaa gtagccctgt atcctagaat        60
tgtgtatctc actgcattgt tcagtttatt acaaccttgc ytctgaaatt tatttatcaa       120
gaagagcaca ttaactaaaa gaagggaaga gaaaatctct aggggcaata catgatgcta       180
tacactagtg catgtacaca c                                                  201

<210> SEQ ID NO 34
<211> LENGTH: 201
<212> TYPE: DNA
<213> ORGANISM: Homo sapiens

<400> SEQUENCE: 34
tttctaagcc ttgatttcct catcagcaaa atgcgaataa tgtcacctta ctcagagggt        60
tcatttaact gttatgtgag acaacaatgt ttgacaccta ycaattattt ttatcgtaaa       120
ttgaacctaa cttttgctag caggtttcct atcaatccaa actgaggttt gctagcaaag       180
tctaaaagca tctgtttttg t                                                  201
```

```
<210> SEQ ID NO 35
<211> LENGTH: 201
<212> TYPE: DNA
<213> ORGANISM: Homo sapiens

<400> SEQUENCE: 35
gtacatccat atgcaaaaga atgaagaatg aaactagact ttcccttctt accctacata      60
aaaatcagct gaaaaggaat cagagaccca aatataagac mccaaatgat aaaactacta     120
gaagaaaaca caggaaatac tgtaggacat tggtttgaga aaatatttta tgactaagtt     180
ctcaaaagca caggcaaaag a                                                201

<210> SEQ ID NO 36
<211> LENGTH: 201
<212> TYPE: DNA
<213> ORGANISM: Homo sapiens

<400> SEQUENCE: 36
aaggaatcag agacccaaat ataagacccc aaatgataaa actactagaa gaaaacacag      60
gaaatactgt aggacattgg tttgagaaaa tattttatga mtaagttctc aaaagcacag     120
gcaaaagaag caaaaagaaa caaacttgat tatatcaaac taaaaagcct ctgcacagaa     180
aaaaaaaata aaaaacaatc a                                                201

<210> SEQ ID NO 37
<211> LENGTH: 201
<212> TYPE: DNA
<213> ORGANISM: Homo sapiens

<400> SEQUENCE: 37
acagatttct gacctgtaac tggaagaagt tcttcattta ctgagacagg caagactatg      60
ggaagagcag gttgggcatg aagatcgtga gcttggtttg ragcttgtta tcattgagat     120
gcccatttga catctatctt tggatatccc cacaagcaga ccttgagaca cacatttgag     180
tgcaagtaat ctacccggga g                                                201

<210> SEQ ID NO 38
<211> LENGTH: 201
<212> TYPE: DNA
<213> ORGANISM: Homo sapiens

<400> SEQUENCE: 38
ttgttttggt tgaagtaggt caaggatacc agtcttcagg gtactctaga agggtctcag      60
ggacacccag gggttcttga ttgacctcat gatacaaagg yctaacacct ccgaagagaa     120
catttaagca aaaggcaaga ctgagcagga agcaaagtct aaataaatat agtgctacta     180
tttttgcaaa gtacagatca g                                                201

<210> SEQ ID NO 39
<211> LENGTH: 201
<212> TYPE: DNA
<213> ORGANISM: Homo sapiens

<400> SEQUENCE: 39
gacagcatag aacattttta tcaccactca gactttact gggcagtgat gttctgtatc       60
ttcattccac tggtggttcc aggggggtctc atttgttaca rtccatgaaa ccgtacactt     120
aaagctgagt gttttaagat atataaatta caccataata gaattgacta caaaaatggt     180
```

```
ttttgagaga aaattgtacc a                                                201
```

```
<210> SEQ ID NO 40
<211> LENGTH: 201
<212> TYPE: DNA
<213> ORGANISM: Homo sapiens

<400> SEQUENCE: 40
catttttatc accactcaga cttttactgg gcagtgatgt tctgtatctt cattccactg       60
gtggttccag ggggtctcat ttgttacaat ccatgaaacc rtacacttaa agctgagtgt      120
tttaagatat ataaattaca ccataataga attgactaca aaaatggttt ttgagagaaa      180
attgtaccaa gaataaactg t                                               201
```

```
<210> SEQ ID NO 41
<211> LENGTH: 201
<212> TYPE: DNA
<213> ORGANISM: Homo sapiens

<400> SEQUENCE: 41
tatatattat ttccttgggc attccagatt ttgtcaagga attttacatt ttgagaagtt       60
gtgcttgact gtcagcactt tgctatgcta tgataaaatc rgaggacaac aaaagtttga      120
tttaagggct tggttaaaag tgttgaattt aagttacccc tatctgtgag tcactatact      180
tagggtgacc acacatcctg g                                               201
```

```
<210> SEQ ID NO 42
<211> LENGTH: 201
<212> TYPE: DNA
<213> ORGANISM: Homo sapiens

<400> SEQUENCE: 42
acactatgtt catagggtgc ttgtggaaat tcaagtaagg tgaaatacat ttcagggtag       60
agagtgacaa aaagggaagc tggagagctg ggtggggcac rtgatggagt ctttgtatat      120
tcaggtagga aggctgcatt gttcccgtgg gcaagtgagg gagctgctga agggttttac      180
tgcgtaagtg acagagtcag a                                               201
```

```
<210> SEQ ID NO 43
<211> LENGTH: 201
<212> TYPE: DNA
<213> ORGANISM: Homo sapiens

<400> SEQUENCE: 43
aggacccagg gaccccatct caggtatttt atgacaggca aaaacccaag ggaattccag       60
agcctgctga tatgaaagtc acatggtttt gaagttatga ygctgaatct ctgtaatcca      120
tcagatccaa ctatttgaca attgttgagt cacttataaa taacacatct tgaggtgctt      180
tgttatcttc tctcaagcag c                                               201
```

```
<210> SEQ ID NO 44
<211> LENGTH: 201
<212> TYPE: DNA
<213> ORGANISM: Homo sapiens

<400> SEQUENCE: 44
taggagaaag taagaaagaa aggaagtaaa agggacttat ataaggagat gtggaatagg       60
aaagaaaggc aaggagaaaa aggggggaaaa gagggtacac rtattccaag taaaataggt      120
actcttaccc caaatagaat ggatagaatt ttctctaaaa agcctttaca gattagtaaa      180
```

```
gattaagagt ttatttttgt a                                                   201

<210> SEQ ID NO 45
<211> LENGTH: 201
<212> TYPE: DNA
<213> ORGANISM: Homo sapiens

<400> SEQUENCE: 45
ctaccattaa ttatccttgg ctaagactta gagccacaga ttactagtta ctaaaaagcc         60
acaaggaaca aaaattcatt cattcttcca ttaacttatt matctataca gctgccaaca        120
aatacctgct gagcatcttc tatgtacaaa attattctgc ttcacatgtt attagcaatg        180
taaattttaa ctgacaaaga c                                                   201

<210> SEQ ID NO 46
<211> LENGTH: 201
<212> TYPE: DNA
<213> ORGANISM: Homo sapiens

<400> SEQUENCE: 46
tagcctattt ctttttttccc tcctaagctg taatggcatt tgcacagctg ttacaaggga        60
agttttaaaa atgcaaataa gaattaggta gactgcacaa rctaataaag agagctttgc        120
caaatattaa aaaacgttct cagtcaaaat aatcatacta atgaaataga aagctcatgt        180
gggagtgatt ttcagtagtt t                                                   201

<210> SEQ ID NO 47
<211> LENGTH: 201
<212> TYPE: DNA
<213> ORGANISM: Homo sapiens

<400> SEQUENCE: 47
atactgatgc catccaatct tcatgcacag agagtcaaag caattttccc aaggtcacca        60
ggttagttgg tggctttgat gtagagctag actagaaccc mgattttctg acaatgcact        120
gaacagatga gattactcaa gtatctgaga aggacacatt tgagtaagca gttaaacaat        180
gcacagttac tagggagcat c                                                   201

<210> SEQ ID NO 48
<211> LENGTH: 201
<212> TYPE: DNA
<213> ORGANISM: Homo sapiens

<400> SEQUENCE: 48
tatgtatgat ggtcatacct aattttctac tctccaattc ctaaattagc tagtggtttt        60
aggaacacac ctagcttaaa cataactttc aatacaccag kttgctcttg cccaaagttt        120
tatatatata taaatatgta tgtatgtaca tataaataca tatatatata tgtatgtatg        180
tatgtattga agagtgaggc t                                                   201

<210> SEQ ID NO 49
<211> LENGTH: 201
<212> TYPE: DNA
<213> ORGANISM: Homo sapiens

<400> SEQUENCE: 49
aaatctgatc tgcctgtggc aggcacagtg ggtgggggag atagtcagaa agggaagaat        60
tgccatgagt tgatgctctg gagaaggtga ggctggctta waaagtcttc actatcccca        120
```

-continued

```
tgcccggctt cacccaattc agatcaaact cttccataaa cttccaggac acaccccaag      180
ctcagctaac ttccctgaag c                                                201

<210> SEQ ID NO 50
<211> LENGTH: 201
<212> TYPE: DNA
<213> ORGANISM: Homo sapiens

<400> SEQUENCE: 50
gttctcactt acaagtggga gctaaataaa gagaacacat aggcacagag aggggaacaa       60
cagacactgg ggccttttgg agggtggagg gtgggaggag rgagaggatc tggaaaaacc      120
accaatgggt actaggttta atacctgggt gatgaaataa tctgtataac aaaccccat       180 gacacaagtt tacatatata a                                                201

<210> SEQ ID NO 51
<211> LENGTH: 201
<212> TYPE: DNA
<213> ORGANISM: Homo sapiens

<400> SEQUENCE: 51 ttcttttgt cgcggtttaa gcccattttc tattgtgcta acctcagcaa aaaaggacat       60
cagctagtta ccattctcct catgattaaa actaattaag rcatccttcc atctctgtca      120
ttagaagcac atgcaaatgg gcatgtttcc ttaatttctg attctaaatt gagaaaagta      180
taaagaagca attctgggct t                                                201
```